US011485792B2

(12) United States Patent
Jones et al.

(10) Patent No.: US 11,485,792 B2
(45) Date of Patent: Nov. 1, 2022

(54) ANTIBODIES, USES THEREOF AND CONJUGATES THEREOF

(71) Applicant: Polytherics Limited, Cambridge (GB)

(72) Inventors: Timothy David Jones, Cambridge (GB); Robert George Edward Holgate, Hertfordshire (GB); Francis Joseph Carr, Aberdeen (GB)

(73) Assignee: Polytherics Limited

( * ) Notice: Subject to any disclaimer, the term of this patent is extended or adjusted under 35 U.S.C. 154(b) by 882 days.

(21) Appl. No.: 16/303,596

(22) PCT Filed: Jun. 6, 2017

(86) PCT No.: PCT/GB2017/051638
§ 371 (c)(1),
(2) Date: Nov. 20, 2018

(87) PCT Pub. No.: WO2017/212250
PCT Pub. Date: Dec. 14, 2017

(65) Prior Publication Data
US 2019/0144562 A1 May 16, 2019

(30) Foreign Application Priority Data

Jun. 6, 2016 (GB) .................................... 1609866
May 19, 2017 (GB) .................................... 1708105

(51) Int. Cl.
| A61K 47/68 | (2017.01) |
| C07K 16/30 | (2006.01) |
| A61K 31/537 | (2006.01) |
| A61K 38/08 | (2019.01) |
| A61K 49/00 | (2006.01) |
| A61K 51/10 | (2006.01) |
| C07K 16/46 | (2006.01) |
| G01N 33/574 | (2006.01) |
| A61K 39/00 | (2006.01) |

(52) U.S. Cl.
CPC ........ *C07K 16/3069* (2013.01); *A61K 31/537* (2013.01); *A61K 38/08* (2013.01); *A61K 47/6803* (2017.08); *A61K 47/6869* (2017.08); *A61K 47/6889* (2017.08); *A61K 49/0002* (2013.01); *A61K 51/1072* (2013.01); *C07K 16/468* (2013.01); *G01N 33/57434* (2013.01); *A61K 2039/505* (2013.01); *C07K 2317/24* (2013.01); *C07K 2317/31* (2013.01); *C07K 2317/73* (2013.01)

(58) Field of Classification Search
None
See application file for complete search history.

(56) References Cited

U.S. PATENT DOCUMENTS

| 8,470,330 B2 | 6/2013 | Maddon et al. |
| 2011/0311550 A1 | 12/2011 | Law et al. |

FOREIGN PATENT DOCUMENTS

| WO | 199803873 | | 1/1998 |
| WO | 199803973 | | 1/1998 |
| WO | 2003034903 | | 5/2003 |
| WO | 2004098535 | | 11/2004 |
| WO | 2005054273 | | 6/2005 |
| WO | 2011069019 | * | 6/2011 |
| WO | 2014064423 | * | 5/2014 |
| WO | 2015177360 | | 11/2015 |
| WO | 2016033547 | | 3/2016 |
| WO | 2016063006 | | 4/2016 |

OTHER PUBLICATIONS

Tagawa, et al., (2010) "Anti-prostate-Specific membrane antigen-based radioimmunotherapy for prostate cancer", Cancer., 116(S4):1075-1083.
Madema, et al. (2015) "Recent Advances in the Development of New Auristatins: Structural Modifications and Application in Antibody Drug Conjugates", Molecular Pharmaceutics, 12:1798-1812.

* cited by examiner

*Primary Examiner* — Karl J Puttlitz
(74) *Attorney, Agent, or Firm* — Shweta Chandra; Bozicevic, Field & Francis LLP

(57) ABSTRACT

An antibody or antigen-binding portion thereof which binds to PSMA and comprises a heavy chain variable domain comprising the sequence given in SEQ ID NO:33, wherein SEQ ID NO:33 is: EVQLVQSGX$^9$E X$^{11}$KKPGASVKV SCKX$^{24}$SGYTFT EYTIHWVX$^{38}$QA X$^{41}$ GKGLEWIGN INPNX$^{55}$GGTTY NOKFEDRX$^{68}$TX$^{70}$ TVDKSTSTAY MELSSLRSED TAVYYCAAGW NFDYWGOGTT VTVSS wherein: X$^9$ is A or P X$^{11}$ is V or L X$^{24}$ is A or T X$^{38}$ is R or K X$^{41}$ is P or H X$^{55}$ is N or Q X$^{68}$ is V or A; and X$^{70}$ is I or L whereby the heavy chain variable domain comprises up to 3 amino acid sequence modification(s) between positions 1-30, 36-49, 67-98 and 105-115 of SEQ ID NO: 33. The invention also provides compounds that include the antibody or antigen-binding portion thereof, such as conjugates, and their use in the treatment or diagnosis of diseases, in particular cancers, particularly prostate cancer.

31 Claims, 26 Drawing Sheets
Specification includes a Sequence Listing.

J591 Humanised VH Variant 1 DNA>Seq ID 1
GAGGTCCAGCTGGTGCAGTCTGGACCTGAGCTGAAGAAGCCTGGGGCCTCAGTG
AAGGTCTCCTGCAAGACTTCTGGATACACATTCACTGAATACACCATCCACTGGG
TGAAGCAGGCCCATGGAAAGGGCCTTGAGTGGATTGGAAACATTAATCCTAACA
ATGGTGGTACTACCTACAACCAGAAGTTCGAGGACAGAGCCACATTGACTGTAG
ACAAGTCCACCAGCACAGCCTACATGGAGCTCAGCAGCCTGAGATCTGAGGATA
CTGCAGTCTATTACTGTGCAGCTGGTTGGAACTTTGACTACTGGGGCCAAGGCAC
CACGGTCACCGTCTCCTCA J591 Humanised VH Variant 2 DNA>Seq ID 2
GAGGTCCAGCTGGTGCAGTCTGGAGCTGAGGTGAAGAAGCCTGGGGCCTCAGTG
AAGGTCTCCTGCAAGACTTCTGGATACACATTCACTGAATACACCATCCACTGGG
TGAAGCAGGCCCCTGGAAAGGGCCTTGAGTGGATTGGAAACATTAATCCTAACA
ATGGTGGTACTACCTACAACCAGAAGTTCGAGGACAGAGCCACAATCACTGTAG
ACAAGTCCACCAGCACAGCCTACATGGAGCTCAGCAGCCTGAGATCTGAGGATA
CTGCAGTCTATTACTGTGCAGCTGGTTGGAACTTTGACTACTGGGGCCAAGGCAC
CACGGTCACCGTCTCCTCA

FIG. 15

J591 Humanised VH Variant 3 DNA>Seq ID 3

GAGGTCCAGCTGGTGCAGTCTGGAGCTGAGGTGAAGAAGCCTGGGGCCTCAGTG
AAGGTCTCCTGCAAGACTTCTGGATACACATTCACTGAATACACCATCCACTGGG
TGAGGCAGGCCCCTGGAAAGGGCCTTGAGTGGATTGGAAACATTAATCCTAACA
ATGGTGGTACTACCTACAACCAGAAGTTCGAGGACAGAGCCACAATCACTGTAG
ACAAGTCCACCAGCACAGCCTACATGGAGCTCAGCAGCCTGAGATCTGAGGATA
CTGCAGTCTATTACTGTGCAGCTGGTTGGAACTTTGACTACTGGGGCCAAGGCAC
CACGGTCACCGTCTCCTCA

J591 Humanised VH Variant 4 DNA>Seq ID 4

GAGGTCCAGCTGGTGCAGTCTGGAGCTGAGGTGAAGAAGCCTGGGGCCTCAGTG
AAGGTCTCCTGCAAGGCTTCTGGATACACATTCACTGAATACACCATCCACTGGG
TGAGGCAGGCCCCTGGAAAGGGCCTTGAGTGGATTGGAAACATTAATCCTAACA
ATGGTGGTACTACCTACAACCAGAAGTTCGAGGACAGAGTCACAATCACTGTAG
ACAAGTCCACCAGCACAGCCTACATGGAGCTCAGCAGCCTGAGATCTGAGGATA
CTGCAGTCTATTACTGTGCAGCTGGTTGGAACTTTGACTACTGGGGCCAAGGCAC
CACGGTCACCGTCTCCTCA

FIG. 15 Cont'd

J591 Humanised VH Variant 5 DNA>Seq ID 5
GAGGTCCAGCTGGTGCAGTCTGGAGCTGAGGTGAAGAAGCCTGGGGCCTCAGTG
AAGGTCTCCTGCAAGGCTTCTGGATACACATTCACTGAATACACCATCCACTGGG
TGAGGCAGGCCCCTGGAAAGGGCCTTGAGTGGATTGGAAACATTAATCCTAACC
AGGGTGGTACTACCTACAACCAGAAGTTCGAGGACAGAGTCACAATCACTGTAG
ACAAGTCCACCAGCACAGCCTACATGGAGCTCAGCAGCCTGAGATCTGAGGATA
CTGCAGTCTATTACTGTGCAGCTGGTTGGAACTTTGACTACTGGGGCCAAGGCAC
CACGGTCACCGTCTCCTCA J591 Humanised VK Variant 1 DNA>Seq ID 6
GACATTGTGATGACCCAGTCTCCAGCTTCCTGTCCGCATCAGTAGGAGACAGGG
TCACCATCACTTGCAAGGCCAGTCAGGATGTGGGTACTGCTGTAGACTGGTATCA
ACAGAAACCAGGGCAAGCTCCTAAACTACTGATTTACTGGGCATCCACCCGGCA
CACTGGAGTCCCTGATCGCTTCACAGGCAGTGGATCTGGGACAGATTTCACTCTC
ACCATCAGCAGACTGCAGTCTGAAGACTTTGCAGATTATTTCTGTCAGCAATATA
ACAGCTATCCTCTCACGTTCGGCCAGGGGACCATGGTGGATATCAAA J591 Humanised VK Variant 2 DNA>Seq ID 7
GACATTGTGATGACCCAGTCTCCCAGCACCCTGTCCGCATCAGTAGGAGACAGG
GTCACCATCACTTGCAAGGCCAGTCAGGATGTGGGTACTGCTGTAGACTGGTATC
AACAGAAACCAGGGCAAGCTCCTAAACTACTGATTTACTGGGCATCCACCCGGC
ACACTGGAGTCCCTGATCGCTTCACAGGCAGTGGATCTGGGACAGATTTCACTCT
CACCATCAGCAGACTGCAGTCTGAAGACTTTGCAGATTATTTCTGTCAGCAATAT
AACAGCTATCCTCTCACGTTCGGCCAGGGGACCAAGGTGGATATCAAA J591 Humanised VK Variant 3 DNA>Seq ID 8
GACATTGTGATGACCCAGTCTCCCAGCACCCTGTCCGCATCAGTAGGAGACAGG
GTCACCATCACTTGCAAGGCCAGTCAGGATGTGGGTACTGCTGTAGACTGGTATC
AACAGAAACCAGGGCAAGCTCCTAAACTACTGATTTACTGGGCATCCACCCGGC
ACACTGGAGTCCCTGATCGCTTCAGCGGCAGTGGATCTGGGACAGATTTCACTCT
CACCATCAGCAGACTGCAGCCTGAAGACTTTGCAGATTATTACTGTCAGCAATAT
AACAGCTATCCTCTCACGTTCGGCCAGGGGACCAAGGTGGATATCAAA

FIG. 16

J591 Humanised VK Variant 4 DNA>Seq ID 9

GACATTCAGATGACCCAGTCTCCCAGCACCCTGTCCGCATCAGTAGGAGACAGG
GTCACCATCACTTGCAAGGCCAGTCAGGATGTGGGTACTGCTGTAGACTGGTATC
AACAGAAACCAGGGCAAGCTCCTAAACTACTGATTTACTGGGCATCCACCCGGC
ACACTGGAGTCCCTGATCGCTTCAGCGGCAGTGGATCTGGGACAGATTTCACTCT
CACCATCAGCAGACTGCAGCCTGAAGACTTTGCAGTTTATTACTGTCAGCAATAT
AACAGCTATCCTCTCACGTTCGGCCAGGGGACCAAGGTGGATATCAAA

J591 Humanised VH Variant 1 amino acid>Seq ID 10

EVQLVQSGPELKKPGASVKVSCKTSGYTFTEYTIHWVKQAHGKGLEWIGNINPNNG
GTTYNQKFEDRATLTVDKSTSTAYMELSSLRSEDTAVYYCAAGWNFDYWGQGTTV
TVSS

J591 Humanised VH Variant 2 amino acid>Seq ID 11

EVQLVQSGAEVKKPGASVKVSCKTSGYTFTEYTIHWVKQAPGKGLEWIGNINPNNG
GTTYNQKFEDRATITVDKSTSTAYMELSSLRSEDTAVYYCAAGWNFDYWGQGTTV
TVSS

J591 Humanised VH Variant 3 amino acid>Seq ID 12

EVQLVQSGAEVKKPGASVKVSCKTSGYTFTEYTIHWVRQAPGKGLEWIGNINPNNG
GTTYNQKFEDRATITVDKSTSTAYMELSSLRSEDTAVYYCAAGWNFDYWGQGTTV
TVSS

FIG. 17

J591 Humanised VH Variant 4 amino acid>Seq ID 13

EVQLVQSGAEVKKPGASVKVSCKASGYTFTEYTIHWVRQAPGKGLEWIGNINPNNG
GTTYNQKFEDRVTITVDKSTSTAYMELSSLRSEDTAVYYCAAGWNFDYWGQGTTV
TVSS

J591 Humanised VH Variant 5 amino acid>Seq ID 14

EVQLVQSGAEVKKPGASVKVSCKASGYTFTEYTIHWVRQAPGKGLEWIGNINPNQG
GTTYNQKFEDRVTITVDKSTSTAYMELSSLRSEDTAVYYCAAGWNFDYWGQGTTV
TVSS

J591 Humanised VK Variant 1 amino acid>Seq ID 15

DIVMTQSPSFLSASVGDRVTITCKASQDVGTAVDWYQQKPGQAPKLLIYWASTRHT
GVPDRFTGSGSGTDFTLTISRLQSEDFADYFCQQYNSYPLTFGQGTMVDIK

J591 Humanised VK Variant 2 amino acid>Seq ID 16

DIVMTQSPSTLSASVGDRVTITCKASQDVGTAVDWYQQKPGQAPKLLIYWASTRHT
GVPDRFTGSGSGTDFTLTISRLQSEDFADYFCQQYNSYPLTFGQGTKVDIK

*FIG. 17* Cont'd

J591 Humanised VK Variant 3 amino acid>Seq ID 17

DIVMTQSPSTLSASVGDRVTITCKASQDVGTAVDWYQQKPGQAPKLLIYWASTRHT
GVPDRFSGSGSGTDFTLTISRLQPEDFADYYCQQYNSYPLTFGQGTKVDIK

J591 Humanised VK Variant 4 amino acid>Seq ID 18

DIQMTQSPSTLSASVGDRVTITCKASQDVGTAVDWYQQKPGQAPKLLIYWASTRHT
GVPDRFSGSGSGTDFTLTISRLQPEDFAVYYCQQYNSYPLTFGQGTKVDIK

Murine J591 VH DNA>Seq ID 19

GAGGTCCAGCTGCAACAGTCTGGACCTGAGCTGAAGAAGCCTGGGACTTCAGTG
AGGATATCCTGCAAGACTTCTGGATACACATTCACTGAATACACCATCCACTGGG
TGAAGCAGAGCCATGGAAAGAGCCTTGAGTGGATTGGAAACATTAATCCTAACA
ATGGTGGTACTACCTACAACCAGAAGTTCGAGGACAAGGCCACATTGACTGTAG
ACAAGTCCTCCAGCACAGCCTACATGGAGCTCCGCAGCCTGACATCTGAGGATTC
TGCAGTCTATTACTGTGCAGCTGGTTGGAACTTTGACTACTGGGGCCAAGGCACC
ACGCTCACCGTCTCCTCA

Murine J591 VK DNA>Seq ID 20

GACATTGTGATGACCCAGTCTCACAAATTCATGTCCACATCAGTAGGAGACAGG
GTCAGCATCATCTGCAAGGCCAGTCAGGATGTGGGTACTGCTGTAGACTGGTATC
AACAGAAACCAGGGCAATCTCCTAAACTACTGATTTACTGGGCATCCACCCGGC
ACACTGGAGTCCCTGATCGCTTCACAGGCAGTGGATCTGGGACAGATTTCACTCT
CACCATCACCAATGTGCAGTCTGAAGACCTGGCAGATTATTTCTGTCAGCAATAT
AACAGCTATCCTCTCACGTTCGGCGCCGGGACCATGCTGGATCTCAAA

FIG. 18

Deimmunised J591 VH DNA>Seq ID 21

GAGGTCCAACTGGTACAGTCTGGACCTGAAGTGAAGAAGCCTGGGGCTACAGTG
AAGATATCCTGCAAGACTTCTGGATACACATTCACTGAATATACCATACACTGGG
TGAAGCAGGCCCCTGGAAAGGGCCTTGAGTGGATTGGAAACATCAATCCTAACA
ATGGTGGTACCACCTACAATCAGAAGTTCGAGGACAAGGCCACACTAACTGTAG
ACAAGTCCACCGATACAGCCTACATGGAGCTCAGCAGCCTAAGATCTGAGGATA
CTGCAGTCTATTATTGTGCAGCTGGTTGGAACTTTGACTACTGGGGCCAAGGGAC
CCTGCTCACCGTCTCCTCA

Deimmunised J591VK DNA>Seq ID 22

GACATCCAGATGACCCAGTCTCCCTCATCCCTGTCCACATCAGTAGGAGACAGGG
TCACCCTCACCTGTAAGGCCAGTCAAGATGTGGGTACTGCTGTAGACTGGTATCA
ACAGAAACCAGGACCATCTCCTAAACTACTGATTTATTGGGCATCCACTCGGCAC
ACTGGAATCCCTAGTCGCTTCTCAGGCAGTGGATCTGGGACAGACTTCACTCTCA
CCATTTCTAGTCTTCAGCCTGAAGACTTTGCAGATTATTACTGTCAGCAATATAAC
AGCTATCCTCTCACGTTCGGTCCTGGGACCAAGGTGGACATCAAA

*FIG. 18 Cont'd*

Murine J591 VH Amino Acid>Seq ID 23
EVQLQQSGPELKKPGTSVRISCKTSGYTFTEYTIHWVKQSHGKSLEWIGNINPNNGGT
TYNQKFEDKATLTVDKSSSTAYMELRSLTSEDSAVYYCAAGWNFDYWGQGTTLTV
SS Murine J591 VK Amino Acid>Seq ID 24
DIVMTQSHKFMSTSVGDRVSIICKASQDVGTAVDWYQQKPGQSPKLLIYWASTRHT
GVPDRFTGSGSGTDFTLTITNVQSEDLADYFCQQYNSYPLTFGAGTMLDLK Deimmunised J591 VH Amino Acid>Seq ID 25
EVQLVQSGPEVKKPGATVKISCKTSGYTFTEYTIHWVKQAPGKGLEWIGNINPNNGG
TTYNQKFEDKATLTVDKSTDTAYMELSSLRSEDTAVYYCAAGWNFDYWGQGTLLT
VSS Deimmunised J591 VK Amino Acid>Seq ID 26
DIQMTQSPSSLSTSVGDRVTLTCKASQDVGTAVDWYQQKPGPSPKLLIYWASTRHT
GIPSRFSGSGSGTDFTLTISSLQPEDFADYYCQQYNSYPLTFGPGTKVDIK Deimmunised J415 VH DNA>Seq ID 27
GAAGTGAAACTTGAGGAGTCTGGAGGAGGCTTGGTGCAACCTGGAGGGTCCATG
AAAATCTCCTGTGTTGCCTCTGGATTCACTTTCAGTAATTACTGGATGAACTGGGT
CCGCCAGTCTCCAGAGAAGGGGCTTGAGTGGGTTGCTGAAATTAGATCGCAATCT
AATAATTTTGCAACACATTATGCGGAGTCTGTGAAGGGAGGGTCATCATCTCAA
GAGATGATTCCAAGAGTAGTGTCTACCTGCAAATGAACAGTTTGAGAGCTGAAG
ACACTGCCGTTTATTACTGTACCAGGCGATGGAATAATTTCTGGGGCCAAGGCAC
CACTGTCACAGTCTCCTCA

FIG. 19

Deimmunised J415 VK DNA>Seq ID 28

AACATTGTAATGACCCAATTTCCCAAATCCATGTCCGCCTCAGCAGGAGAGAGG
ATGACCTTGACCTGCAAGGCCAGTGAGAATGTGGGTACTTATGTGTCCTGGTATC
AACAGAAACCAACACAGTCTCCTAAGATGTTGATATACGGGGCATCCAACCGGT
TCACTGGGGTCCCAGATCGCTTCTCCGGCAGTGGATCTGGAACAGATTTCATTCT
GACCATCAGCAGTGTGCAGGCAGAAGACCTTGTAGATTATTGTGGACAGAG
TTACACCTTTCCGTACACGTTCGGAGGGGGGACCAAGCTGGAAATGAAG

Deimmunised J415 VH Amino Acid>Seq ID 29

EVKLEESGGGLVQPGGSMKISCVASGFTFSNYWMNWVRQSPEKGLEWVAEIRSQSN
NFATHYAESVKGRVIISRDDSKSSVYLQMNSLRAEDTAVYYCTRRWNNFWGQGTTV
TVSS

Deimmunised J415 VK Amino Acid>Seq ID 30

NIVMTQFPKSMSASAGERMTLTCKASENVGTYVSWYQQKPTQSPKMLIYGASNRFT
GVPDRFSGSGSGTDFILTISSVQAEDLVDYYCGQSYTFPYTFGGGTKLEMK

*FIG. 19* Cont'd

PSMA Antigen DNA>Seq ID 31

ATGTGGAACCTGCTGCACGAGACAGACAGCGCCGTGGCCACCGCCAGACGGCCT
AGATGGCTGTGTGCCGGCGCTCTGGTGCTGGCTGGCGGCTTCTTCCTGCTGGGCT
TCCTGTTCGGCTGGTTCATCAAGAGCAGCAACGAGGCCACCAACATCACCCCCA
AGCACAACATGAAGGCCTTTCTGGACGAGCTGAAGGCCGAGAATATCAAGAAGT
TCCTGTACAACTTCACCCAGATCCCCCACCTGGCCGGCACCGAGCAGAACTTCCA
GCTCGCCAAGCAGATCCAGAGCCAGTGGAAGAGTTCGGCCTGGACAGCGTGGA
ACTGGCCCACTACGACGTGCTGCTGAGCTACCCCAACAAGACCCACCCCAACTA
CATCAGCATCATCAACGAGGACGGCAACGAGATTTTCAACACCAGCCTGTTCGA
GCCCCCTCCACCCGGCTACGAGAACGTGTCCGACATCGTGCCCCCATTCAGCGCC
TTCAGTCCACAAGGCATGCCCGAGGGCGACCTGGTGTACGTGAACTACGCCCGG
ACCGAGGACTTCTTCAAGCTGGAACGGGACATGAAGATCAACTGCTCCGGCAAG
ATCGTGATCGCCAGATACGGCAAGGTGTTCCGGGGCAACAAAGTGAAGAACGCC
CAGCTCGCTGGGGCCAAGGGCGTGATCCTGTACAGCGACCCCGCCGACTACTTC
GCCCCTGGCGTGAAGTCCTACCCCGACGGCTGGAATCTGCCTGGCGGCGGAGTG
CAGCGGGGCAACATCCTGAACCTGAACGGCGCTGGCGACCCCCTGACACCTGGC
TACCCCGCCAACGAGTACGCCTACAGACGGGGAATCGCCGAGGCCGTGGGCCTG
CCTAGCATCCCTGTGCACCCCATCGGCTACTACGACGCCCAGAAACTGCTGGAAA
AGATGGGCGGCAGCGCCCCTCCCGACAGCTCTTGGAGAGGCAGCCTGAAGGTGC
CCTACAACGTGGGCCCTGGCTTCACCGGCAACTTCAGCACCCAGAAAGTGAAGA
TGCACATCCACAGCACCAACGAAGTGACCCGGATCTACAACGTGATCGGCACCC
TGAGAGGCGCCGTGGAACCCGACAGATACGTGATCCTGGGCGGCCACCGGGATA
GCTGGGTGTTCGGCGGCATCGACCCTCAGTCTGGCGCCGCTGTGGTGCACGAGAT
CGTGCGGAGCTTTGGCACCCTGAAGAAGAGGGCTGGCGGCCCAGACGGACCAT
CCTGTTCGCCTCTTGGGACGCCGAGGAATTCGGCCTGCTGGGCAGCACCGAGTGG
GCCGAGGAAAACAGCAGACTGCTCCAGGAACGGGGCGTCGCCTACATCAACGCC
GACAGCAGCATCGAGGGCAACTACACCCTGCGGGTGGACTGCACCCCCCTGATG
TACAGCCTGGTGCACAACCTGACCAAAGAGCTGAAGTCCCCCGACGAGGGCTTC
GAGGGCAAGAGCCTGTACGAGAGCTGGACCAAGAAGTCCCCCAGCCCCGAGTTC
AGCGGCATGCCCAGAATCAGCAAGCTGGGCAGCGGCAACGACTTCGAGGTGTTC
TTCCAGCGGCTGGGAATCGCCAGCGGCAGAGCCCGGTACACCAAGAACTGGGAG
ACAAACAAGTTCTCCGGCTACCCCCTGTACCACAGCGTGTACGAGACATACGAG

FIG. 20

CTGGTGGAAAAGTTCTACGACCCCATGTTCAAGTACCACCTGACCGTGGCCCAAG
TGCGCGGAGGCATGGTGTTCGAGCTGGCCAACAGCATCGTGCTGCCCTTCGACTG
CCGGGACTACGCCGTGGTGCTGCGGAAGTACGCCGACAAAATCTACAGCATCAG
CATGAAGCACCCCAGGAAATGAAGACCTACAGCGTGTCCTTCGACAGCCTGTT
CAGCGCCGTGAAGAATTTCACCGAGATCGCCAGCAAGTTCAGCGAGCGGCTCCA

PSMA Antigen DNA>Seq ID 31 - continued
GGACTTCGACAAGAGCAACCCCATCGTGCTGAGAATGATGAACGACCAGCTCAT
GTTCCTGGAACGGGCCTTCATCGACCCCCTGGGCCTGCCCGACCGGCCCTTCTAC
AGACACGTGATCTATGCCCCCAGCAGCCACAACAAATACGCCGGCGAGAGCTTC
CCCGGAATCTACGATGCCCTGTTCGACATCGAGAGCAAGGTGGACCCCAGCAAG
GCCTGGGGCGAAGTGAAGCGGCAAATCTACGTGGCCGCCTTCACAGTGCAAGCC
GCTGCCGAGACACTGAGCGAAGTGGCCTAG PSMA Antigen Amino Acid>Seq ID 32
MWNLLHETDSAVATARRPRWLCAGALVLAGGFFLLGFLFGWFIKSSNEATNITPKH
NMKAFLDELKAENIKKFLYNFTQIPHLAGTEQNFQLAKQIQSQWKEFGLDSVELAHY
DVLLSYPNKTHPNYISIINEDGNEIFNTSLFEPPPPGYENVSDIVPPFSAFSPQGMPEGD
LVYVNYARTEDFFKLERDMKINCSGKIVIARYGKVFRGNKVKNAQLAGAKGVILYS
DPADYFAPGVKSYPDGWNLPGGGVQRGNILNLNGAGDPLTPGYPANEYAYRRGIAE
AVGLPSIPVHPIGYYDAQKLLEKMGGSAPPDSSWRGSLKVPYNVGPGFTGNFSTQKV
KMHIHSTNEVTRIYNVIGTLRGAVEPDRYVILGGHRDSWVFGGIDPQSGAAVVHEIV
RSFGTLKKEGWRPRRTILFASWDAEEFGLLGSTEWAEENSRLLQERGVAYINADSSIE
GNYTLRVDCTPLMYSLVHNLTKELKSPDEGFEGKSLYESWTKKSPSPEFSGMPRISK
LGSGNDFEVFFQRLGIASGRARYTKNWETNKFSGYPLYHSVYETYELVEKFYDPMF
KYHLTVAQVRGGMVFELANSIVLPFDCRDYAVVLRKYADKIYSISMKHPQEMKTYS
VSFDSLFSAVKNFTEIASKFSERLQDFDKSNPIVLRMMNDQLMFLERAFIDPLGLPDR
PFYRHVIYAPSSHNKYAGESFPGIYDALFDIESKVDPSKAWGEVKRQIYVAAFTVQA
AAETLSEVA.

*FIG. 20 Cont'd*

AB-P1 VH Amino Acid>Seq ID 35

MELGLRWGFL VALLRGVQCQ VQLVESGGGV VQPGRSLRLS CAASGFAFSR
YGMHWVRQAP GKGLEWVAVI WYDGSNKYYA DSVKGRFTIS RDNSKNTQYL
QMNSLRAEDT AVYYCARGGD FLYYYYGMD VWGQGTTVTV SS

This is the sequence presented as SEQ ID NO 15 in US 8,470,332 B

AB-P1 VK Amino Acid>Seq ID 36

MRVPAQLLGL LLLWLPDTRC DIQMTQSPSS LSASVGDRVT ITCRASQGIS
NYLAWYQQKT GKVPKFLIYE ASTLQSGVPS RFSGGGSGTD FTLTISSLQP
EDVATYYCQN YNSAPFTFGP GTKVDIK

This is the sequence presented as SEQ ID NO 17 in US 8,470,332 B

AB-P2 VH Amino Acid>Seq ID 37

MELGLRWVLL VALLRGVQCQ VQLVESGGGV VQPGRSLRLS CAASGFTFSN
YVMHWVRQAP GKGLEWVAII WYDGSNKYYA DSVKGRFTIS RDNSKNTLYL
QMNSLRAEDT AVYYCAGGYN WNYEYHYYGM DVWGQGTTVT VSS

This is the sequence presented as SEQ ID NO 19 in US 8,470,332 B

AB-P2 VK Amino Acid>Seq ID 38

MRVPAQLLGL LLLCFPGARC DIQMTQSPSS LSASVGDRVT ITCRASQGIT
NYLAWFQQKP GKAPKSLIYA ASSLQSGVPS KFSGSGSGTD FSLTISSLQP
EDFATYYCQQ YNSYPITFGQ GTRLEIK

This is the sequence presented as SEQ ID NO 21 in US 8,470,332 B

*FIG. 21*

```
            10         20         30         40         50         60
            |          |          |          |          |          |
Seq ID 23   EVQLQQSGPELKKPGTSVRISCKTSGYTFTEYTIHWKQSHGKSLEWGNINPNNGGTTY
Seq ID 25   EVQLVQSGPEVKKPGATVKISCKTSGYTFTEYTIHWKQAPGKGLEWGNINPNNGGTTY
Seq ID 10   EVQLVQSGPELKKPGASVKVSCKTSGYTFTEYTIHWKQAHGKGLEWGNINPNNGGTTY
Seq ID 11   EVQLVQSGAEVKKPGASVKVSCKTSGYTFTEYTIHWKQAPGKGLEWGNINPNNGGTTY
Seq ID 12   EVQLVQSGAEVKKPGASVKVSCKTSGYTFTEYTIHWRQAPGKGLEWGNINPNNGGTTY
Seq ID 13   EVQLVQSGAEVKKPGASVKVSCKASGYTFTEYTIHWRQAPGKGLEWGNINPNNGGTTY
Seq ID 14   EVQLVQSGAEVKKPGASVKVSCKASGYTFTEYTIHWRQAPGKGLEWGNINPNQGGTTY 70         80         90        100        110
            |          |          |          |          |
Seq ID 23   NQKFEDKATLTVDKSSSTAYMELRSLTSEDSAVYYCAAGWNFDYWGQGTTLTVSS
Seq ID 25   NQKFEDKATLTVDKSTDTAYMELSSLRSEDTAVYYCAAGWNFDYWGQGTLLTVSS
Seq ID 10   NQKFEDRATLTVDKSTSTAYMELSSLRSEDTAVYYCAAGWNFDYWGQGTTVTVSS
Seq ID 11   NQKFEDRATITVDKSTSTAYMELSSLRSEDTAVYYCAAGWNFDYWGQGTTVTVSS
Seq ID 12   NQKFEDRATITVDKSTSTAYMELSSLRSEDTAVYYCAAGWNFDYWGQGTTVTVSS
Seq ID 13   NQKFEDRVTITVDKSTSTAYMELSSLRSEDTAVYYCAAGWNFDYWGQGTTVTVSS
Seq ID 14   NQKFEDRVTITVDKSTSTAYMELSSLRSEDTAVYYCAAGWNFDYWGQGTTVTVSS 10         20         30         40         50         60
            |          |          |          |          |          |
Seq ID 24   DIVMTQSHKFMSTSVGDRVSIICKASQDVGTAVDWYQQKPGQSPKLLIYWASTRHTGVPD
Seq ID 26   DIQMTQSPSSLSTSVGDRVTLTCKASQDVGTAVDWYQQKPGPSPKLLIYWASTRHTGIPS
Seq ID 15   DIVMTQSPSFLSASVGDRVTITCKASQDVGTAVDWYQQKPGQAPKLLIYWASTRHTGVPD
Seq ID 16   DIVMTQSPSTLSASVGDRVTITCKASQDVGTAVDWYQQKPGQAPKLLIYWASTRHTGVPD
Seq ID 17   DIVMTQSPSTLSASVGDRVTITCKASQDVGTAVDWYQQKPGQAPKLLIYWASTRHTGVPD
Seq ID 18   DIQMTQSPSTLSASVGDRVTITCKASQDVGTAVDWYQQKPGQAPKLLIYWASTRHTGVPD 70         80         90        100
            |          |          |          |
Seq ID 24   RFTGSGSGTDFTLTITNVQSEDLADYFCQQYNSYPLTFGAGTMLDLK
Seq ID 26   RFSGSGSGTDFTLTISSLQPEDFADYYCQQYNSYPLTFGPGTKVDIK
Seq ID 15   RFTGSGSGTDFTLTISRLQSEDFADYFCQQYNSYPLTFGQGTMVDIK
Seq ID 16   RFTGSGSGTDFTLTISRLQSEDFADYFCQQYNSYPLTFGQGTKVDIK
Seq ID 17   RFSGSGSGTDFTLTISRLQPEDFADYYCQQYNSYPLTFGQGTKVDIK
Seq ID 18   RFSGSGSGTDFTLTISRLQPEDFAVYYCQQYNSYPLTFGQGTKVDIK
```

*FIG. 22*

ANTIBODIES, USES THEREOF AND CONJUGATES THEREOF

The present invention relates to novel humanised antibodies that bind to PSMA, uses of the antibodies and compounds that include the antibodies, for example conjugates of the antibodies, for example antibody-drug conjugates. The antibodies and conjugates of the invention find use in the treatment or diagnosis of diseases, in particular cancers, particularly prostate cancer.

BACKGROUND TO THE INVENTION

The specificity of antibodies for specific antigens on the surface of target cells and molecules has led to their extensive use as carriers of a variety of diagnostic and therapeutic agents. For example, antibodies conjugated to labels and reporter groups such as fluorophores, radioisotopes and enzymes find use in labelling and imaging applications, while conjugation to cytotoxic agents and chemotherapy drugs allows targeted delivery of such agents to specific tissues or structures, for example particular cell types or growth factors, minimising the impact on normal, healthy tissue and significantly reducing the side effects associated with chemotherapy treatments. Antibody-drug conjugates have extensive potential therapeutic applications in several disease areas.

Prostate cancer, also known as carcinoma of the prostate, is the development of cancer in the prostate, a gland in the male reproductive system. Globally it is the second most common type of cancer and the fifth leading cause of cancer-related death in men. First line therapy for advanced prostate cancer is androgen deprivation. Following progression, chemotherapy offers benefit, but responses are transient and there is no therapy that has been shown to improve survival beyond initial chemotherapy. Metastatic prostate cancer is poorly responsive to conventional chemotherapy. There thus remains a need for improved therapies.

Prostate Specific Membrane Antigen (PSMA) expression is highly associated with prostate cancer and with other solid tumours. PSMA is present on the cell surface of some normal prostatic epithelial cells, normal renal proximal tubular cells, proximal small bowel and some astrocytes (found in the brain). PSMA is highly upregulated/overexpressed on prostate cancer (PCa) cells. Expression levels of PSMA increase along with prostate cancer progression and high PSMA levels in early stage prostate cancer predict an increased likelihood of recurrence. A significant proportion of solid tumours express PSMA in their tumor neo-vasculature whereas normal vascular endothelium is PSMA-negative. It has been observed that PSMA increases available folates by hydrolyzing glutamated folates. It has been postulated that PSMA stimulates the development of prostate cancer by increasing folate levels for the cancer cells to use to survive and grow.

Anti-PSMA antibodies have previously been generated (see for example WO98/03973) and modified antibodies with reduced immunogenicity in humans have been prepared (see for example WO2004/098535). An example of a de-immunised IgG monoclonal antibody that binds PSMA is J591. The amino acid sequence of the variable domain heavy chain of the murine J591 antibody is given herein as SEQ ID NO:23, and the corresponding light chain is given herein as SEQ ID NO:24. The amino acid sequence of the variable domain heavy chain of the de-immunised antibody J591 is given herein as SEQ ID NO: 25, and the corresponding light chain is given herein as SEQ ID NO:26. De-immunised J591 has been used in radiolabelled form in the clinic and it has been shown to be well-tolerated and non-immunogenic (see Tagawa et al., *Cancer*, 2010, 116(4), 1075-1083).

Further examples of antibodies that bind PSMA are disclosed in WO03/034903 and its family members, including U.S. Pat. No. 8,470,330B. For example, antibody "AB-PG1-XG1-006" has heavy and light chain sequences SEQ ID NO 15 and SEQ ID NO 17 in those publications (given herein as SEQ ID NO's 35 and 36), and antibody "AB-PG1-XG1-026" has heavy and light chain sequences SEQ ID NO 19 and SEQ ID NO 21 in those publications (given herein as SEQ ID NO's 37 and 38).

In addition to having good target binding affinity, low off-target binding and low immunogenicity, an antibody that is to be a candidate as a drug (whether on its own or conjugated to another active component) should have good stability. That is to say it should have a low propensity to denature or aggregate, or disassociate into component fragments. Given this set of demanding properties, there remains a need for the development of further beneficial anti-PSMA antibodies.

SUMMARY OF THE INVENTION

The present invention relates to novel humanised antibodies which bind to PSMA. The invention provides an antibody or antigen-binding portion of an antibody which binds to PSMA and comprises a heavy chain variable domain comprising the sequence given in SEQ ID NO:33, wherein

```
SEQ ID NO: 33 is:
EVQLVQSGX⁹E X¹¹KKPGASVKV SCKX²⁴SGYTFT EYTIHWVX³⁸QA

X⁴¹GKGLEWIGN INPNX⁵⁵GGTTY NQKFEDRX⁶⁸TX⁷⁰

TVDKSTSTAY MELSSLRSED T AVYYCAAGW NFDYWGQGTT

VTVSS
``` wherein:
$X^9$ is A or P
$X^{11}$ is V or L
$X^{24}$ is A or T
$X^{38}$ is R or K
$X^{41}$ is P or H
$X^{55}$ is N or Q
$X^{68}$ is V or A; and
$X^{70}$ is I or L whereby the heavy chain variable domain comprises up to 3 amino acid sequence modification(s) between positions 1-30, 36-49, 67-98 and 105-115 of SEQ ID NO: 33.

In preferred embodiments, the antibody or antigen-binding portion thereof of the invention also comprises a light chain variable domain comprising the sequence given in SEQ ID NO:34, wherein

```
SEQ ID NO: 34 is:
DIX³MTQSPSX¹⁰ LSASVGDRVT ITCKASQDVG TAVDWYQQKP

GQAPKLLIYW ASTRHTGVPD RFX⁶³GSGSGTD FTLTISRLQX⁸⁰

EDFAX⁸⁵YX⁸⁷CQQ YNSYPLTFGQ GTX¹⁰³VDIK
``` wherein
$X^3$ is Q or V
$X^{10}$ is T or F
$X^{63}$ is S or T $X^{50}$ is P or S $X^{85}$ is V or D $X^{87}$ is Y or F; and $X^{103}$ is K or M whereby the light chain variable domain comprises up to 3 amino acid sequence modification(s) between positions 1-23, 35-49, 57-88 and 98-107 of SEQ ID NO: 34. The antibodies and antigen-binding portions of the invention have strong binding to PSMA, low immunogenicity and good stability. Antibodies with good stability are advantageous as they have less propensity to denature or aggregate, or disassociate into component fragments. As a result, they may reside within the circulation in a native conformation for longer. Reduced fragmentation is an advantage as a fragmented antibody (or antibody-drug conjugate) loses its ability to bind to the target antigen. Cytotoxic drugs tend to be hydrophobic, and they thus show a tendency for aggregation in solution. A reduced tendency to aggregate is also an advantage for an antibody-drug conjugate. Aggregates can prompt an immune response, that is to say they can be immunogenic. An antibody-drug conjugate comprising an antibody or antigen-binding portion of the invention has good stability and a reduced tendency to aggregate in solution.

The antibodies and antigen-binding portions of the invention display good high selectivity, potency and/or activity. Antibodies displaying high selectivity, potency and activity are especially preferred.

The antibodies and antigen-binding portions of the invention also display good efficiency of expression. The efficiency of expression of the antibody is an important factor in production of an antibody or antibody-drug conjugate. For example, obtaining stable, high-yield expression of an antibody is important for production for diagnostic or therapeutic use, in which large quantities of an antibody are required even to conduct a clinical trial. The expression level of the light or heavy chains and their ease of manipulation throughout expression and purification may thus influence the choice of antibody selected for production. Antibodies that express well with high solubility and low propensity to aggregate are preferred.

BRIEF DESCRIPTION OF THE FIGURES

FIGS. 15 to 21 show the nucleic acid and amino acid sequences of heavy and light chain antibody fragments of the invention and the prior art, and the nucleic acid and amino acid sequences of PSMA antigen.

FIG. 22 shows an alignment of heavy and light chain sequences of the invention with prior art sequences.

DETAILED DESCRIPTION

Figure 1A:
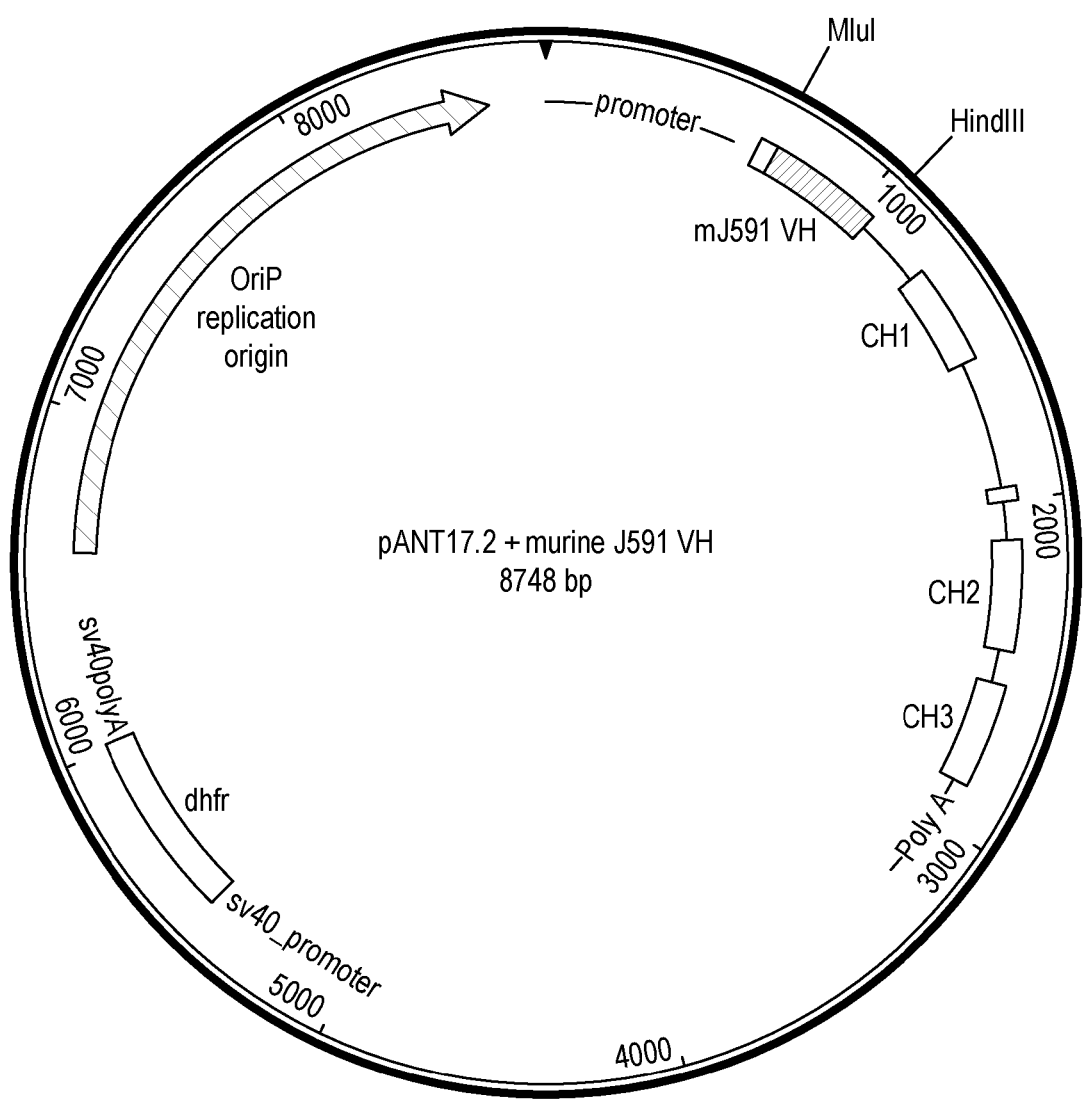
FIG. 1 shows the structure of the pANT expression vectors for (a) heavy and light chain antibody domains, and (b) Human PSMA Antigen.
Figure 1A:
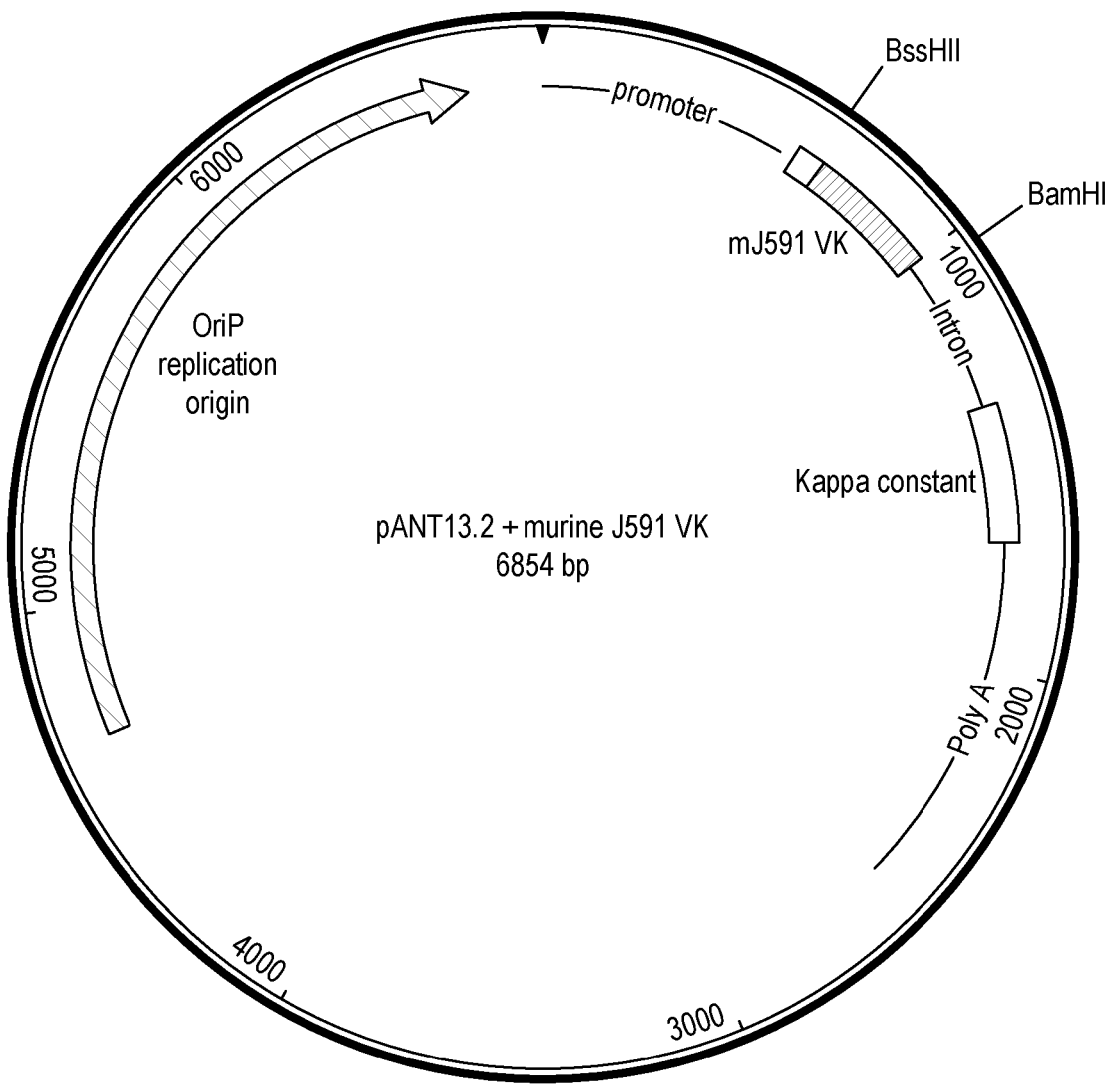

The CDR regions are underlined in the Sequences SEQ ID NO: 33 and 34 above. The present invention encompasses antibodies and antigen-binding portions thereof having up to 3 amino acid sequence modification(s) outside the CDR regions as defined above, in one or both of the heavy chain and light chain variable domains. For example, such a modification may improve the binding affinity and/or other biological properties of an antibody. Amino acid sequence modification(s) can be prepared by introducing appropriate nucleotide changes into an antibody nucleic acid, or by peptide synthesis. Such modification(s) include, for example, deletions from, and/or insertions into and/or substitutions of, residues within the amino acid sequences of an antibody. Any combination of deletion, insertion, and substitution can be made to arrive at the final construct, provided that the final construct possesses the desired characteristics. Substitutions may be conservative or non-conservative substitutions. The amino acid changes also may alter post-translational processes of an antibody, such as changing the number or position of glycosylation sites.

For example, when the amino acid sequence modification is a substitution, it is preferably a conservative substitution, i.e., an amino acid substitution that does not substantially reduce specific binding (e.g., as measured by the $K_D$) of the antibody or antigen-binding portion thereof to an antigen (e.g., substitutions that increase binding, that do not significantly alter binding, or that reduce binding by no more than about 40%, typically no more than about 30%, more typically no more than about 20%, even more typically no more than about 10%, or most typically no more than about 5%, as determined by standard binding assays such as, e.g., ELISA).

For example, 0, 1 or 2 residues outside the CDR regions in the heavy chain, and 0, 1 or 2 residues outside the CDR regions in the light chain can be replaced by another amino acid.

For example, 0 or 1 residues outside the CDR regions in the heavy chain can be replaced by another amino acid. For example, 0 or 1 residues outside the CDR regions in the light chain can be replaced by another amino acid. Preferably, no residues in the Sequences SEQ ID NO: 33 and 34 are varied to amino acids other than the ones specifically recited. For example, SEQ ID NO:33 can be the sequence of SEQ ID:10, SEQ ID: 11, SEQ ID:12, SEQ ID:13 or SEQ ID:14. For example, SEQ ID NO:34 can be the sequence of SEQ ID:15, SEQ ID:16, SEQ ID:17 or SEQ ID:18.

In SEQ ID NO:33, it is preferred that:

$X^9$ is A, $X^{11}$ is V, $X^{24}$ is A or T, $X^{38}$ is R or K, $X^{41}$ is P, $X^{55}$ is N or Q, $X^{68}$ is V or A and $X^{70}$ is I. For example, SEQ ID NO:33 can be the sequence of SEQ ID: 11, SEQ ID: 12, SEQ ID:13 or SEQ ID:14.

In SEQ ID NO:33, it is further preferred that:

$X^9$ is A, $X^{11}$ is V, $X^{24}$ is A, $X^{38}$ is R, $X^{41}$ is P, $X^{55}$ is N or Q, $X^{68}$ is V and $X^{70}$ is I. For example, SEQ ID NO:33 can be the sequence of SEQ ID:13 or SEQ ID:14.

In particular, it is especially preferred that:

$X^9$ is A, $X^{11}$ is V, $X^{24}$ is A, $X^{38}$ is R, $X^{41}$ is P, $X^{55}$ is N, $X^{68}$ is V and $X^{70}$ is I. For example, SEQ ID NO:33 can be the sequence of SEQ ID:13.

In SEQ ID NO:34, it is preferred that:

$X^3$ is Q or V, $X^{10}$ is T, $X^{63}$ is S or T, $X^{80}$ is P or S, $X^{85}$ is V or D, $X^{87}$ is Y or F and $X^{103}$ is K. For example, SEQ ID NO:43 can be the sequence of SEQ ID:16, SEQ ID:17 or SEQ ID:18.

In SEQ ID NO:34, it is further preferred that:

$X^3$ is Q or V, $X^{10}$ is T, $X^{63}$ is S, $X^{80}$ is P, $X^{85}$ is V or D, $X^{87}$ is Y and $X^{103}$ is K. For example, SEQ ID NO:34 can be the sequence of SEQ ID:17 or SEQ ID:18.

In SEQ ID NO:34, it is especially preferred that:

$X^3$ is Q, $X^{10}$ is T, $X^{63}$ is S, $X^{80}$ is P, $X^{85}$ is V, $X^{87}$ is Y and $X^{103}$ is K. For example, SEQ ID NO:34 can be the sequence of SEQ ID:18.

In a preferred embodiment, the antibody of the present invention comprises a variable domain heavy chain of SEQ ID NO: 13 and a variable domain light chain of SEQ ID NO: 17 (referred to as 'VH4/VK3'); or a variable domain heavy chain of SEQ ID NO:14 and a variable domain light chain of SEQ ID NO: 17 (referred to as 'VH5/VK3'); or a variable domain heavy chain of SEQ ID NO:13 and a variable domain light chain of SEQ ID NO:18 (referred to as 'VH4/VK4'); or a variable domain heavy chain of SEQ ID NO: 14 and a variable domain light chain of SEQ ID NO: 18 (referred to as 'VH5/VK4').

The antibodies of the invention are humanised antibodies that bind to PSMA (for example human PSMA) with an equilibrium dissociation constant (Kd) of $10^{-8}$M or lower, for example 10-9M or lower, for example $750 \times 10^{-12}$M or lower, for example $500 \times 10^{-12}$M or lower. For example, antibodies of the invention specifically bind to a human prostate cancer cell.

The antibodies of the invention have improved stability compared with certain prior humanised (or de-immunised) anti-PSMA antibodies. The antibodies of the invention thus have less propensity to denature or aggregate, or disassociate into component fragments. It is hypothesised that, as a result, they remain in the circulation in a native conformation for longer. A reduced tendency to aggregate is a particular advantage for an antibody-drug conjugate and for reagents that produce these conjugates; cytotoxic drugs tend to be hydrophobic and thus conjugation reagents and anti-body-drug conjugates with cytotoxic drugs have a propensity to aggregate in solution, which significantly reduces their effectiveness. A fragmented antibody (including as part of an antibody-drug conjugate) loses its ability to bind to the target antigen. An antibody with a reduced susceptibility to fragmentation is thus also advantageous.

An antibody of the invention may have a heavy chain of isotype IgG1, IgG2, IgG3 or IgG4, IgM, IgA1, IgA2, IgAsec, IgD or IgE. IgG1, IgG2, IgG3 and IgG4 are especially preferred. Alternatively, it may have an altered IgG constant region, for example to increase or decrease binding to Fc receptors or to increase or decrease binding to complement, for example, the IgG constant region may be IgG4k or IgG1k. An antibody of the invention may have an antibody light chain that is a kappa light chain.

A compound of the invention may be full-length antibody (e.g., an IgG4 or IgG1 antibody). Alternatively, it can include only an antigen-binding portion. For example, a compound of the invention may be a Fab, F(ab'), F(ab')$_2$, a Fd chain, Fv fragment or a single chain Fv (scFv), a disulfide-linked Fv (sdFv), a fragment comprising only a $V_H$ domain, including nanobodies or fragments from camels, llamas or the like. The invention also provides bispecific and multispecific antibodies (two or more different antibody molecules joined together to give two or more different specificities) including at least one antibody or antigen-binding portion thereof as described hereinabove. The antigen-binding portion may for example be a minibody composed of different permutations of scFv fragments or diabodies and Fc fragments or $C_H$ domains such as scFv-Fc, scFv-Fc-scFv, (Fab'ScFv)$_2$, scDiabody-Fc, scDiabody-$C_H$3, scFv-$C_H$3, scFv-$C_H$2-$C_H$3 fusion proteins and so forth. An antibody fragment can be produced by enzymatic cleavage, synthetic or recombinant techniques.

An antibody or antigen-binding portion thereof of the invention may be produced by a mammalian cell line, especially CHO or NS0 cells. For example, an antibody of the invention may be a monoclonal antibody.

The antibodies or antigen-binding portions thereof of the invention find use as diagnostic or therapeutic agents in vivo and in vitro.

In another aspect, the invention provides nucleic acid molecules encoding the humanised antibodies or antigen-binding portions thereof, of the invention. Accordingly, recombinant expression vectors that include the antibody-encoding nucleic acids of the invention, and host cells transfected with such vectors, are also encompassed by the invention, as are methods of making the antibodies of the invention by culturing these host cells. For example, the antibodies or antigen-binding portions thereof of the invention can be encoded by human IgG heavy chain and human kappa light chain nucleic acids with sequences as set forth in SEQ ID NO:1 to SEQ ID NO:5 (heavy chain) or SEQ ID NO: 6 to SEQ ID NO: 9 (light chain), or variants thereof.

For example, a variant nucleic acid may be determined to be within the scope of the invention where this includes sequences containing or substantially identical to SEQ ID NO: 1 to SEQ ID NO:9 for example as determined by its ability to hybridise under stringent conditions to a nucleic acid of the present invention, for example a nucleic acid of SEQ ID NO:1 to SEQ ID NO:9. The term "hybridise" refers to the binding, duplexing, or hybridising of a molecule to a particular nucleotide sequence under stringent hybridisation conditions when that sequence is present in a complex mixture (e.g. total cellular or library DNA or RNA), wherein the particular nucleotide sequence is detected at least at about 10 times background. Stringent hybridisation conditions will be selected, for example, to be 5-10° C. lower than the thermal melting point (Tm) for the specific sequence at a defined ionic strength and pH. For example, stringent hybridisation conditions can be:

50% deionized formamide

2× Saline Sodium Citrate (SSC)*

50 mM Na$_2$HPO$_4$/NaH$_2$PO$_4$ buffer; pH 7.0

1 mM EDTA target DNA/RNA (1 mg/ml each)

probe (approx. 20-200 ng/ml) Temperature: 37 to 42° C.; Hybridization time: 5 minutes-16 hours SSC: 1×SSC=150 mM NaCl, 15 mM sodium citrate; pH 7.0.

Conjugates

The invention further provides an antibody or antigen-binding portion thereof, for example Fab, according to the invention, conjugated via a linker to a payload which may be another functional molecule, for example a therapeutic, diagnostic or labelling agent, and/or a polymer. A single molecule of another functional molecule may be present, or two or more molecules may be present. It is often preferred that antibody drug conjugates should contain multiple copies of the drug. The functional molecule may for example be another peptide or protein, e.g. a Fab' fragment. The inclusion of one or more drug molecules, for example a cytotoxic agent or a toxin, is preferred. Auristatins and maytansinoids are typical cytotoxic drugs. Labelling agents (which should be understood to include imaging agents) may for example include a radionuclide, a fluorescent agent (for example an amine derivatised fluorescent probe such as 5-dimethylaminonaphthalene-1-(N-(2-aminoethyl))sulfonamide-dansyl ethylenediamine, Oregon Green® 488 cadaverine (catalogue number 0-10465, Molecular Probes), dansyl cadaverine, N-(2-aminoethyl)-4-amino-3,6-disulfo-1,8-naphthalimide, dipotassium salt (lucifer yellow ethylenediamine), or rhodamine B ethylenediamine (catalogue number L 2424, Molecular Probes), or a thiol derivatised fluorescent probe for example BODIPY® FL L-cystine (catalogue number B-20340, Molecular Probes). The labelling agent may also be a dye, a contrast agent, a bioluminescent agent, an enzyme, an enhancing agent, or a nanoparticle. Biotin may also be used.

In some embodiments, an antibody or antigen-binding portion thereof is conjugated to a therapeutic agent. A "therapeutic agent" as used herein is an atom, molecule, or compound that is useful in the treatment of a disease or condition mediated by PSMA or characterised by increased expression of PSMA. Examples of therapeutic agents include, but are not limited to, drugs, chemotherapeutic agents, therapeutic antibodies and antibody fragments, toxins, radioisotopes, enzymes (for example, enzymes to cleave prodrugs to a cytotoxic agent at the site of the antigen binding construct binding), nucleases, hormones, immunomodulators, antisense oligonucleotides, chelators, boron compounds, photoactive agents and dyes, and nanoparticles.

In some embodiments, a therapeutic approach includes radioimmunotherapy by attaching an appropriate radiolabel such as, Iodine-131, a beta-emitter, such as, Yttrium-90, Lutetium-177, Copper-67, Astatine-211, Lead-212/Bismuth-212, Actinium-225/Bismuth-213, and Thorium, which can deliver cell damage and death to a target tissue.

In some embodiments, nanoparticles are used in therapeutic applications as drug carriers that, when conjugated to an antibody or antigen-binding portion thereof, deliver chemotherapeutic agents, hormonal therapeutic agents, radiotherapeutic agents, toxins, or any other cytotoxic or anticancer agent known in the art to cancerous cells that overexpress PSMA. Any of the antibodies or antigen-binding portions thereof described herein may be further conjugated with one or more additional therapeutic agents, detectable markers, nanoparticles, carriers or a combination thereof. For example, an antibody or antigen-binding portion thereof may be radiolabeled with Iodine-131 and conjugated to a lipid carrier, such that the anti-PSMA-lipid conjugate forms a micelle. The micelle can incorporate one or more therapeutic or detectable markers. Alternatively, in addition to the carrier, the antigen binding construct may be radiolabeled with Iodine-131 I (for example, at a tyrosine residue) and conjugated to a drug (for example, at the epsilon amino group of a lysine residue), and the carrier may incorporate an additional therapeutic or detectable marker.

In some embodiments, antigen-binding portions of the invention are conjugated to a therapeutic agent. While these antigen-binding portions can have a shorter circulation half-life compared to a full-length antibody, in some embodiments, these formats can exhibit improved tumor penetration based on their smaller size and be therapeutically effective when appropriately armed with a cytotoxic drug or radioisotope. In some embodiments, an antibody drug-conjugate approach can be employed. In some embodiments, treatment with these fragments armed with a cytotoxic drug or radionuclide result in less nonspecific toxicity as they will be cleared from the body more rapidly.

In some embodiments, an antibody or antigen-binding portion thereof is conjugated to a detectable marker. As used herein, a "detectable marker" includes an atom, molecule, or compound that is useful in diagnosing, detecting or visualizing a location and/or quantity of a PSMA antigen in a cell, tissue, organ or the like. Detectable markers that can be used in accordance with the embodiments herein include, but are not limited to, radioactive substances (for example, radioisotopes, radionuclides, radiolabels or radiotracers), dyes, contrast agents, fluorescent compounds or molecules, bioluminescent compounds or molecules, enzymes and enhancing agents (for example, paramagnetic ions). In addition, some nanoparticles, for example quantum dots and metal nanoparticles are known in the art to be suitable for use as a detection agent. In some embodiments, the detectable marker is IndoCyanine Green (ICG), Zirconium-89, IR800, and/or another near infrared dye.

Exemplary radioactive substances that can be used as detectable markers in accordance with the embodiments herein include, but are not limited to, $^{18}$F, $^{18}$F-FAC, $^{32}$P, $^{33}$P, $^{45}$Ti, $^{47}$Sc, $^{52}$Fe, $^{59}$Fe, $^{62}$CU, $^{64}$Cu, $^{67}$CU, $^{67}$Ga, $^{68}$Ga, $^{75}$Sc, $^{7}$As, $^{86}$Y, $^{90}$Y, $^{89}$Sr, $^{89}$Zr, $^{94}$Tc, $^{94}$Tc, $^{99}$mTc, 99Mo, $^{105}$Pd, $^{101}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, 166Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Exemplary paramagnetic ions substances that can be used as detectable markers include, but are not limited to ions of transition and lanthanide metals (for example metals having atomic numbers of 6-9, 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Exemplary contrast agents that can be used as detectable markers in accordance with the embodiments of the disclosure include, but are not limited to, barium, diatrizoate, ethiodised oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, thallous chloride, or combinations thereof.

Bioluminescent and fluorescent compounds or molecules and dyes that can be used as detectable markers in accordance with the embodiments of the disclosure include, but are not limited to, fluorescein, fluorescein isothiocyanate (FITC), OREGON GREEN™, rhodamine, Texas red, tetrarhodimine isothiocynate (TRITC), Cy3, Cy5, and the like, fluorescent markers (for example, green fluorescent protein (GFP), phycoerythrin, and the like), autoquenched fluorescent compounds that are activated by tumour-associated proteases, enzymes (for example, luciferase, horseradish peroxidase, alkaline phosphatase, and the like), nanoparticles, biotin, digoxigenin or combination thereof.

Enzymes that can be used as detectable markers in accordance with the embodiments of the disclosure include, but are not limited to, horseradish peroxidase, alkaline phosphatase, acid phoshatase, glucose oxidase, β-galactosidase, β-glucoronidase or β-lactamase. Such enzymes may be used in combination with a chromogen, a fluorogenic compound or a luminogenic compound to generate a detectable signal.

Suitable linkers for attaching the payload to the antibody or antigen-binding portion thereof are those described in the section on Conjugating Reagents below. The linker is advantageously degradable, as described below. In some preferred embodiments, the linker includes a polymer, as described below.

Preferred conjugates according to the invention are those in which the bonding of the payload to the antibody or antigen-binding portion thereof is via a bonding portion which has the general formula:

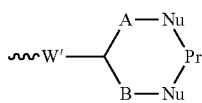
(I)

in which Pr represents said antibody or antigen-binding portion thereof, each Nu represents a nucleophile present in or attached to the antibody or antigen-binding portion thereof, each of A and B independently represents a $C_{1-4}$ alkylene or alkenylene chain, and W' represents an electron withdrawing group or a group obtained by reduction of an electron withdrawing group.

An electron withdrawing group W' may for example be a keto group —CO—, an ester group —O—CO— or a sulfone group —$SO_2$—. Preferably W' represents one of these groups or a group obtainable by reduction of one of these groups as described below. Preferably W' represents a keto group or a group obtainable by reduction of a keto group, especially a CH.OH group.

Preferably the grouping has the formula:

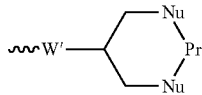
(Ia)

especially

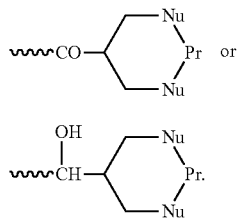
(Ib)

(Ic)

Nucleophilic groups in the antibody or antigen-binding portion thereof are for example provided by cysteine, lysine or histidine residues, and Nu may for example be a sulfur atom or an amine group. In one preferred embodiment of the invention, each Nu represents a sulfur atom present in a cysteine residue present in the antibody or antigen-binding portion thereof. The antibody according to the invention will generally contain four interchain disulphide bonds. Each of these may be reduced to provide free thiol groups which act as nucleophiles. If each of these disulphide bonds is bridged as shown in the formulae I above, a conjugate with a drug-antibody ratio (DAR) of 4 will be produced. In another embodiment, each Nu represents an imidazole group present in a histidine residue present in a polyhistidine tag attached to said antibody or antigen-binding portion thereof.

The conjugate of the invention may, for example, be of the general formula:

(III)

in which D represents the payload;
q represents an integer from 1 to 10;
$Lk^1$ represents a linker;
r represents an integer from 1 to 10;
$P^1$ represents a bond or a c-valent group —$P^2$—NH— where c is from 2 to 11 and $P^2$ is a group containing at least one ethylene unit —$CH_2$—$CH_2$— or ethylene glycol unit —O—$CH_2$—$CH_2$—;
e represents an integer from 1 to 10;
$Lk^2$ represents a bond or a d-valent linker where d is from 2 to 11 and which consists of from
1 to 9 aspartate and/or glutamate residues;
$Lk^3$ represents a linker of the general formula:

—CO-Ph-Y—Z—  (AII)

in which Ph is an optionally substituted phenyl group; Y represents a CO group or a CH.OH group; and Z represents a group of formula:

(AIII)

(AIV)

in which each of A and B represents a $C_{1-4}$ alkylene or alkenylene group;
Ab represents the antibody or antigen-binding portion thereof according to the invention, being bonded to $Lk^3$ via two sulfur atoms derived from a disulfide bond in the antibody or antigen-binding portion thereof; and e represents an integer from 1 to s where s is the number of disulfide bonds present in the antibody or antigen-binding portion thereof prior to conjugating to $Lk^3$.

The meanings of q, r, e, c and d determine the total number of D groups present. This number may for example be up to 20, for example up to 15, for example up to 10, for example 1, 2, 3 or 4.

Conjugating Reagents

Conjugates according to the invention may be prepared by reacting a conjugating reagent with an antibody or an antigen-binding portion thereof according to the invention. The conjugation may for example be carried out by chemical coupling, genetic fusion, non-covalent association or otherwise, but is preferably carried out by chemical coupling. Typically, the conjugating reagent will comprise a functional group capable of covalently reacting with at least one electrophile or, especially, nucleophile present in the antibody or an antigen-binding portion thereof, which functional group is attached to a payload via a linker. Many conjugating reagents which can be used to conjugate a payload to an antibody or an antigen-binding portion thereof are known, and any of these may be used to prepare a conjugate according to the invention.

For example, the reagent may contain a maleimide group, a click-chemistry group, for example an azide or alkyne group, an amine group, a carboxyl group, or an active ester group. Other possible approaches include the use of antibodies that have been recombinantly engineered with an amino acid specifically for conjugation such as engineered cysteines or non-natural amino acids, and enzymatic conjugation through a specific enzymatic reaction such as with transglutaminase. The reaction site on the antibody or an antigen-binding portion thereof may be either nucleophilic or electrophilic in nature. Common protein conjugation sites are at lysine or cysteine amino acid residues or carbohydrate moieties. Alternatively, conjugation may occur at a polyhistidine tag which has been attached to the antibody or an antigen-binding portion thereof.

A conjugating reagent is advantageously capable of reacting with a nucleophile in the antibody or an antigen-binding portion thereof and hence becoming chemically bonded thereto. As such the conjugating reagent typically includes at least one leaving group which is lost on reaction with a nucleophile. The conjugating reagent may, for example, include two or more leaving groups. Preferably the conjugating reagent is capable of reacting with two nucleophiles. Advantageously, the conjugating reagent comprises at least two leaving groups. If two or more leaving groups are present, these may be the same or different. Alternatively, a conjugating reagent may contain a single group which is chemically equivalent to two leaving groups and which single group is capable of reacting with two nucleophiles.

One group of reagents is based on the bis-halo- or bis-thio-maleimides and derivatives thereof as described in Smith et al., *J. Am. Chem. Soc.*, 2010, 132, 1960-1965, and Schumacher et al., *Bioconj. Chem.*, 2011, 22, 132-136. These reagents contain the functional grouping:

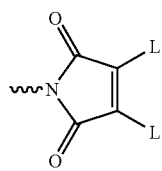

in which each L is a leaving group. The nitrogen atom of the maleimide ring may carry the payload, directly or indirectly.

Similarly, maleimides containing a single leaving group L:

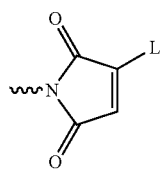

may be used. Again, the nitrogen atom of the maleimide ring carries the payload, directly or indirectly.

Also, maleimides lacking a leaving group:

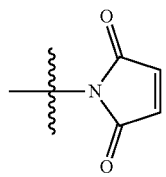 [SMILES: *N1C(=O)C=CC1=O]

may be used. Again, the nitrogen atom of the maleimide ring carries the payload, directly or indirectly.

In a preferred embodiment, a conjugating reagent contains the functional grouping:

(CI)

in which W represents an electron-withdrawing group, for example a keto group, an ester group —O—CO—, a sulfone group —SO$_2$—, or a cyano group; A represents a C$_{1-5}$ alkylene or alkenylene chain; B represents a bond or a C$_{1-4}$ alkylene or alkenylene chain; and either each L independently represents a leaving group, or both Ls together represent a leaving group. Reagents of this type are described in *Bioconj. Chem* 1990(1), 36-50, *Bioconj. Chem* 1990(1), 51-59, and *J. Am. Chem. Soc.* 110, 5211-5212. When reagents containing such groups react with the antibody or an antigen-binding portion thereof, a first leaving group L is lost to form in situ a conjugating reagent containing a functional grouping of formula:

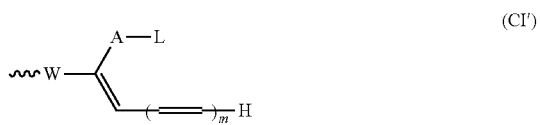

(CI')

in which m is 0 to 4, which reacts with a first nucleophile. The second leaving group L is then lost, and reaction with a second nucleophile occurs. As an alternative to using a reagent containing the functional grouping CI as starting material, reagents containing the functional grouping CI' may be used as starting material.

Preferably W represents a keto group. Preferably A represents —CH$_2$— and B represents a bond.

Particularly preferred functional groupings of formula CI and CI' have the formulae:

(CIa)

or

(CIa')

For example, the group may be of the formula:

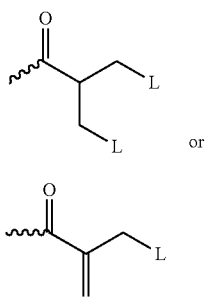

Another group of conjugating reagents contains the functional grouping:

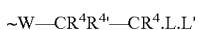 (CII)

in which W has the meaning and the preferred meanings given above, and either
- each $R^4$ represents a hydrogen atom or a $C_{1-4}$alkyl group, $R^{4'}$ represents a hydrogen atom, and either each L independently represents a leaving group, or both Ls together represent a leaving group; or
- each $R^4$ represents a hydrogen atom or a $C_{1-4}$alkyl group, L represents a leaving group, and $R^{4'}$ and L' together represent a bond.

Another group of conjugating reagents includes the functional grouping:

 (CIII) or

 (CIII')

in which W has the meaning and preferred meanings given above and p represents 0 or an integer of from 1 to 4, preferably 0. An especially preferred reagent of this type includes the functional grouping:

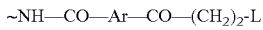 (CIIIa) or

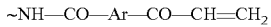 (CIIIa')

in which Ar represents an optionally substituted aryl, especially phenyl, group.

A leaving group L may for example be —SP, —OP, —$SO_2$P, —$OSO_2$P, —N+$PR^2R^3$, halogen, —OØ, in which P represents a hydrogen atom, an alkyl (preferably $C_{1-6}$alkyl), aryl (preferably phenyl), or alkyl-aryl (preferably $C_{1-6}$alkyl-phenyl) group, or is a group which includes a portion —$(CH_2CH_2O)_n$— in which n is a number of two or more, especially 6 or more, and each of $R^2$ and $R^3$ independently represents a hydrogen atom, a $C_{1-4}$alkyl group, or a group P, and Ø represents a substituted aryl, especially phenyl, group, containing at least one substituent, for example —CN, —$CF_3$, —$NO_2$, —$CO_2R'$, —COH, —$CH_2OH$, —COR', —OR', —OCOR', —$OCO_2R'$, —SR', —SOR', —$SO_2R'$, —NHCOR', —NR'COR', —$NHCO_2R'$, —$NR'CO_2R'$, —NO, —NHOH, —NROH, —CH=N—NR'COR', —$N^+R'_3$, halogen, especially chlorine or, especially, fluorine, —C≡CR' and —CH=CR'$_2$, in which each R' represents a hydrogen atom or an alkyl (preferably $C_{1-6}$alkyl), aryl (preferably phenyl), or alkyl-aryl (preferably $C_{1-6}$alkyl-phenyl) group. The presence of electron withdrawing substituents is preferred.

Conjugating reagents in which P represents a group which includes a portion —$(CH_2CH_2O)_n$— in which n is a number of two or more are the subject of our copending application GB 1418186.1, from which PCT/GB2015/052952, now published as WO2016/059377, claims priority. This application discloses the following:

"The leaving group may for example include —$(CH_2CH_2O)_n$—$R^1$ where $R^1$ is a capping group. A very wide range of capping groups may be used. $R^1$ may for example be a hydrogen atom, an alkyl group, especially a $C_{1-4}$alkyl group, particularly a methyl group, or an optionally substituted aryl group, for example an optionally substituted phenyl group, for example a tolyl group. Alternatively, the capping group may include a functional group such as a carboxyl group or an amine group. Such capping groups may for example have the formula —$CH_2CH_2CO_2H$ or —$CH_2CH_2NH_2$, and may be prepared by functionalising the terminal unit of a —$(CH_2CH_2O)_n$— chain. Alternatively, rather than being terminated by a capping group, the —$(CH_2CH_2O)_n$— group may have two points of attachment within the conjugating reagent such that chemically the equivalent of two leaving groups are present, capable of binding to two nucleophiles.

The —$(CH_2CH_2O)_n$— portion of the leaving group is based on PEG, polyethylene glycol. The PEG may be straight-chain or branched, and it may be derivatised or functionalised in any way. n is a number of 2 or more, for example 2, 3, 4, 5, 6, 7, 8, 9 or 10. For example, n may be from 5 to 9. Alternatively, n may be a number of 10 or more. There is no particular upper limit for n. n may for example be 150 or less, for example 120 or less, for example 100 or less. For example n may be from 2 to 150, for example from 7 to 150, for example from 7 to 120. The PEG portion —$(CH_2CH_2O)_n$— of a leaving group may for example have a molecular weight of from 1 to 5 kDa; it may for example be 1 kDa, 2 kDa, 3 kDa, 4 kDa or 5 kDa. A leaving group may if desired contain two or more portions —$(CH_2CH_2O)_n$— separated by one or more spacers.

A leaving group in a reagent according to the invention is suitably of the formula —SP, —OP, —$SO_2$P, —$OSO_2$P, —$N+PR^2R^3$, in which P is a group which includes a portion —$(CH_2CH_2O)_n$— and each of $R^2$ and $R^3$ independently represents a hydrogen atom, a $C_{1-4}$alkyl group, or a group P. Preferably each of $R^2$ and $R^3$ represents a $C_{1-4}$alkyl group, especially a methyl group, or, especially, a hydrogen atom. Alternatively, the conjugating reagent may include a group of formula —S—P—S—; —O—P—O—; —$SO_2$—P—$SO_2$—; —$OSO_2$—P—$OSO_2$—; and —$N^+R^2R^3$—P—$N^+R^2R^3$—. Specific groups of this type include —S—$(CH_2CH_2O)_n$—S—, —O—$(CH_2CH_2O)_n$—O—; —$SO_2$—$(CH_2CH_2O)_n$—$SO_2$—; —$OSO_2$—$(CH_2CH_2O)_n$—$OSO_2$—; or —$N^+R^2R^3$—$(CH_2CH_2O)_n$—$N^+R^2R^3$—. They can also include groups of the type:

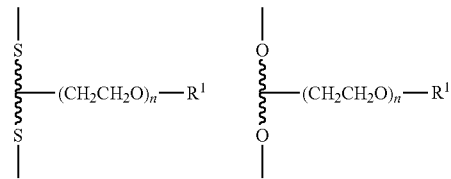

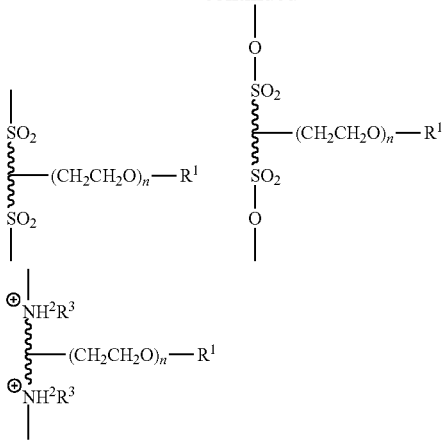

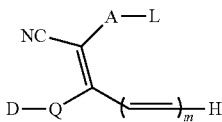
(CId')

in which D represents a payload and Q represents a linking group.

Preferred conjugating reagents include the following:

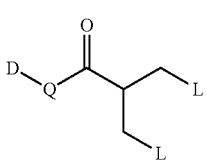
(CIe)

or

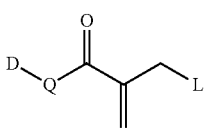
(CIe')

or

D—Q—NH—CO—Ar—CO—(CH$_2$)$_2$—L  or   (CIIIb)

D—Q—NH—CO—Ar—CO—CH═CH$_2$.   (CIIIb')

in which D represents the payload and Q represents a linking group.

The conjugating reagent may, for example, be of the general formula:

$$((D_q\text{-Lk}^1)_r\text{—P})_z\text{-Lk}^2\text{-Lk}^3\text{-(L)}_2 \quad (II)$$

in which D represents the payload;
q represents an integer from 1 to 10;
Lk$^1$ represents a linker;
r represents an integer from 1 to 10;
P$^1$ represents a bond or a c-valent group —P$^2$—NH— where c is from 2 to 11 and P$^2$ is a group containing at least one ethylene unit —CH$_2$—CH$_2$— or ethylene glycol unit —O—CH$_2$—CH$_2$—;
z represents an integer from 1 to 10;
Lk$^2$ represents a bond or a d-valent linker where d is from 2 to 11 and which consists of from
1 to 9 aspartate and/or glutamate residues;
Lk$^3$ represents a linker of the general formula:

—CO-Ph-Y—Z—   (EII)

in which Ph is an optionally substituted phenyl group; Y represents a CO group or a CH(OH) group; and Z represents a group of formula:

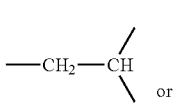
(EIII)

or

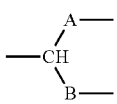
(EIV)

where the —(CH$_2$CH$_2$O)$_n$— group is carried by any suitable linking group, for example an alkyl group. These divalent groups are chemically equivalent to two leaving groups capable of reacting with two nucleophiles."

An especially preferred leaving group L present in a conjugating reagent is —SP or —SO$_2$P, especially —SO$_2$P. Within this group, one preferred embodiment is where P represents a phenyl or, especially, a tosyl group. Another preferred embodiment is where P represents a group which includes a portion —(CH$_2$CH$_2$O)$_n$—, especially one in which n has one of the values mentioned above, especially 7. An especially preferred leaving group L is —SO$_2$—(CH$_2$CH$_2$O)$_n$—H/Me, especially —SO$_2$—(CH$_2$CH$_2$O)$_7$—H/Me. Throughout this Specification, any reference to a leaving group L should be understood to include a specific reference to these preferred groups, especially —SO$_2$—(CH$_2$CH$_2$O)$_n$—H/Me, and more especially —SO$_2$—(CH$_2$CH$_2$O)$_7$—H/Me.

Conjugating reagents may contain more than one functional group. For example, a reagent may contain a functional grouping of type C above at one end of the molecule, and one or more additional functional groupings, either capable of conjugating with the antibody or an antigen-binding portion thereof or any other molecule, elsewhere in the molecule. Such structures are described in for example Belcheva et al, *J. Biomater. Sci Polymer Edn.* 9(3), 207-226 and are useful in the synthesis of conjugates containing multiple proteins.

Conjugating reagents containing the unit of formula CI/CI' may have the formula (CIc) or (CIc') or, where W represents a cyano group, (CId) or (CId'):

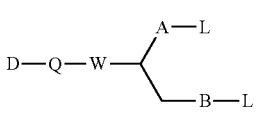
(CIc)

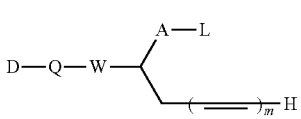
(CIc')

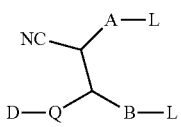
(CId)

in which each of A and B represents a $C_{1-4}$alkylene or alkenylene group; and in which L is a leaving group, for example one of those described below.

Any suitable linking group Q or $Lk^1$ may be used. In one embodiment, Q or $Lk^1$ may for example be a direct bond, an alkylene group (preferably a $C_{1-10}$ alkylene group), or an optionally-substituted aryl or heteroaryl group, any of which may be terminated or interrupted by one or more oxygen atoms, sulfur atoms, —NR" groups (in which R" represents a hydrogen atom or an alkyl (preferably $C_{1-6}$alkyl), aryl (preferably phenyl), or alkyl-aryl (preferably $C_{1-6}$alkyl-phenyl) group), keto groups, —OCO— groups, —COO— groups, —O—CO—O, —O—CO—NR"—, —NR"COO—, —CONR"— and/or —NR"CO— groups. Such aryl and heteroaryl groups Q form one preferred embodiment of the invention. Suitable aryl groups include phenyl and naphthyl groups, while suitable heteroaryl groups include pyridine, pyrrole, furan, pyran, imidazole, pyrazole, oxazole, pyridazine, pyrimidine and purine. Especially suitable linking groups Q or $Lk^1$ are heteroaryl or, especially, aryl groups, especially phenyl groups. These may have a linking group to the therapeutic agent D, for example a group which is, or contains, an —NR"—CO— or —CO—NR"— group, for example an —NH—CO— or —CO—NH— group.

Substituents which may be present on an optionally substituted aryl, especially phenyl, or heteroaryl group include for example one or more of the same or different substituents selected from alkyl (preferably $C_{1-4}$alkyl, especially methyl, optionally substituted by OH or $CO_2H$), —CN, —$NO_2$, —$CF_3$, NR"$_2$, —$CO_2$R", —COH, —$CH_2$OH, —COR", —OR", —OCOR", —$OCO_2$R", —SR", —SOR", —$SO_2$R", —NR"COR", —NR".$CO_2$R", —NO, —NHOH, —NR".OH, —CH═N—NR".CO R", —$N^+$R"$_3$, halogen, for example fluorine or chlorine, —C═CR" and —CH═CR"$_2$, in which each R" independently represents a hydrogen atom or an alkyl (preferably $C_{1-6}$alkyl), aryl (preferably phenyl), or alkyl-aryl (preferably $C_{1-6}$alkyl-phenyl) group. The presence of electron withdrawing substituents is especially preferred. Preferred substituents include for example —CN, —$CF_3$, —$NO_2$, —OR", —OCOR", —SR", —NR"COR", —NHOH and —NR"$CO_2$R".

In another embodiment, a linker Q or $Lk^1$, or any other linker in a conjugate according to the invention, may contain a degradable group, i.e. it may contain a group which breaks under physiological conditions, separating the payload from the antibody or an antigen-binding portion thereof to which it is bonded. Alternatively, it may be a linker that is not cleavable under physiological conditions.

Suitable degradable linkers are discussed in more detail below.

The meanings of q, r, z, c and d determine the total number of D groups present. This number may for example be up to 20, for example up to 15, for example up to 10, for example 1, 2, 3 or 4.

Linkers

Conjugates of the invention and conjugating reagents suitable for preparing them contain a linker linking the antibody or antigen-binding portion thereof to the payload. This linker may be non-degradable or degradable under physiological conditions. Conjugates advantageously comprise a degradable linker which contains a group which breaks under physiological conditions, separating the payload from the antibody or antigen-binding portion thereof to which it is, or will ultimately be, bonded. Where a linker breaks under physiological conditions, it is preferably cleavable under intracellular conditions. Where the target is intracellular, preferably the linker is substantially insensitive to extracellular conditions (i.e. so that delivery to the intracellular target of a sufficient dose of the therapeutic agent is not prohibited). Suitable degradable linkers are discussed in more detail below.

Where a linker, for example Q or $Lk^1$, contains a degradable group, this is generally sensitive to hydrolytic conditions, for example it may be a group which degrades at certain pH values (e.g. acidic conditions). Hydrolytic/acidic conditions may for example be found in endosomes or lysosomes. Examples of groups susceptible to hydrolysis under acidic conditions include hydrazones, semicarbazones, thiosemicarbazones, cis-aconitic amides, orthoesters and ketals. Examples of groups susceptible to hydrolytic conditions include:

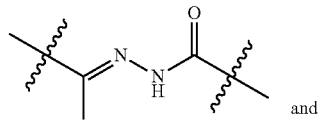 and

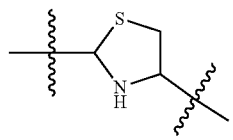

In a preferred embodiment, a linker, for example Q or $Lk^1$, is or includes (EV)

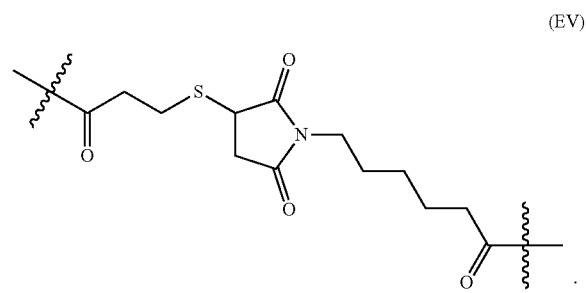 [SMILES: *C(=O)CCCCCN1C(=O)CC(SCCC(*)=O)C1=O]

For example, a linker, for example Q or $Lk^1$ may be:

(EVa)

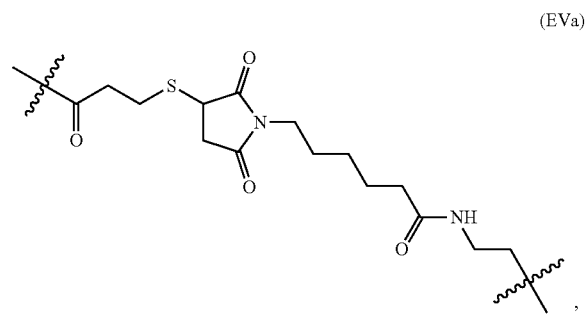 [SMILES: *CCNC(=O)CCCCCN1C(=O)CC(SCCC(*)=O)C1=O]

in which case it is preferably bonded to D and $P^1$ groups as shown:

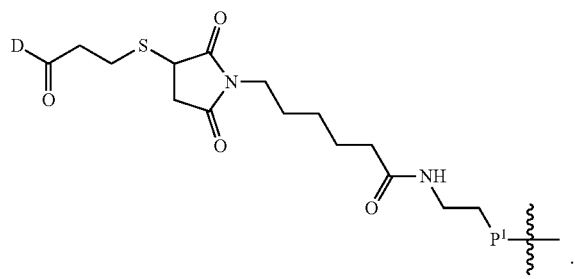

A linker may also be susceptible to degradation under reducing conditions. For example, it may contain a disulfide group that is cleavable on exposure to biological reducing agents, such as thiols. Examples of disulfide groups include:

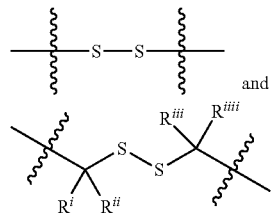

in which $R^i$, $R^{ii}$, $R^{iii}$ and $R^{iiii}$ are each independently hydrogen or $C_{1-4}$alkyl. In a preferred embodiment a linker, for example Q or $Lk^1$, is or includes

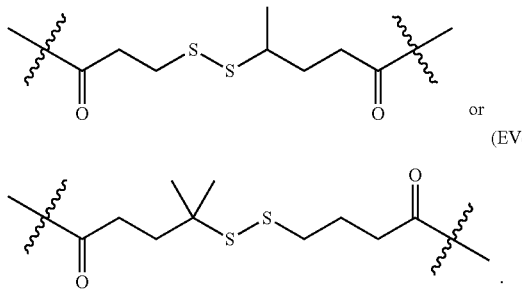

For example, it may be

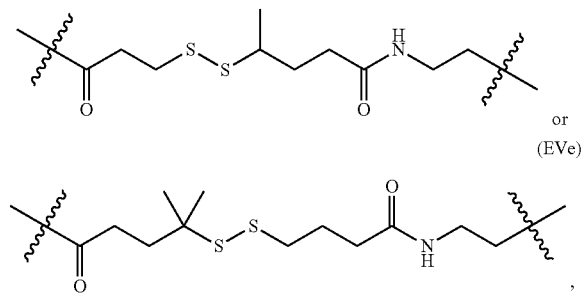

in which case the linker is preferably bonded to D and $P^1$ groups as shown:

A linker, for example Q or $Lk^1$, may also contain a group which is susceptible to enzymatic degradation, for example it may be susceptible to cleavage by a protease (e.g. a lysosomal or endosomal protease) or peptidase. For example, it may contain a peptidyl group comprising at least one, for example at least two, or at least three amino acid residues (e.g. Phe-Leu, Gly-Phe-Leu-Gly, Val-Ala, Val-Cit, Phe-Lys). For example, it may be an amino acid chain having from 1 to 5, for example 2 to 4, amino acids.

Another example of a group susceptible to enzymatic degradation is:

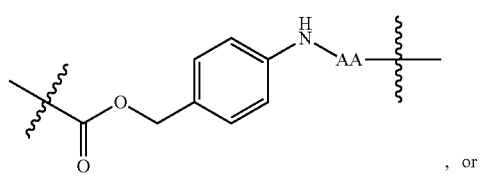

wherein AA represents an amino acid sequence, especially one containing 1 or two amino acid residues, especially a protease-specific amino acid sequence of two residues, such as Val-Cit.

In a preferred embodiment, the linker, for example Q or $Lk^1$, is or includes:

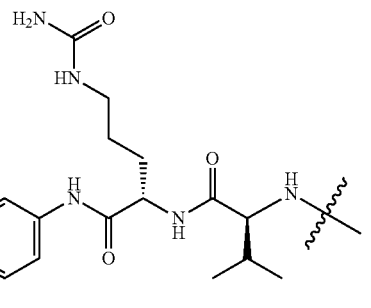

For example, it may be

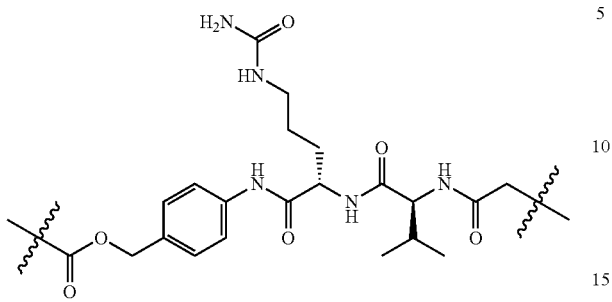

(EVg)

in which case it is preferably bonded to the payload D and P¹ groups as shown below

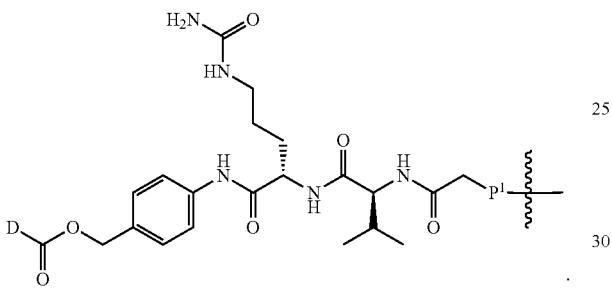

In one embodiment, a linker, for example Q or Lk¹, carries a single payload (i.e. q=1 in conjugating reagents of the formula (II)). The specific linkers (EVa), (EVd) and (EVe) shown above are of this type. In another embodiment, the linker carries multiple payloads (i.e. q>1, for example 2, 3 or 4, in conjugating reagents of the formula (II)) and the linker is used as a means of incorporating more than one copy of the therapeutic agent into a conjugate of the invention. In one embodiment, this may be achieved by the use of a branching linker Lk¹ and/or Lk², which may for example incorporate an aspartate or glutamate or similar residue. This introduces a branching element of formula:

(EVI)

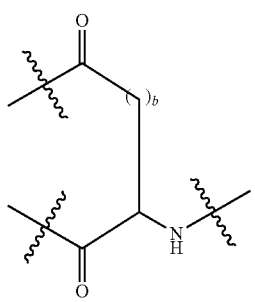

where b is 1, 2 or 3, b=1 being aspartate and b=2 being glutamate, and b=3 representing one preferred embodiment. Each of the acyl moieties in the formula EVI may be coupled to a payload via a suitable linker Lk¹ᵃ, where Lk¹ᵃ is any suitable linker, for example a degradable linker incorporating one of the linkages mentioned above. In particular embodiments, Lk¹ᵃ represents the group (EVa), (EVd) or (EVe) shown above. The amino group of the aspartate or glutamate or similar residue may be bonded to P¹ by any suitable means, for example the linkage may be via an amide bond, e.g. the branching group above may be connected to P¹ via a —CO—CH₂— group, thus:

(EVIa)

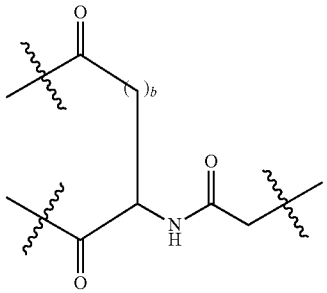

If desired, the aspartate or glutamate or similar residue may be coupled to further aspartate and/or glutamate and/or similar residues, for example:

(ECIIa)

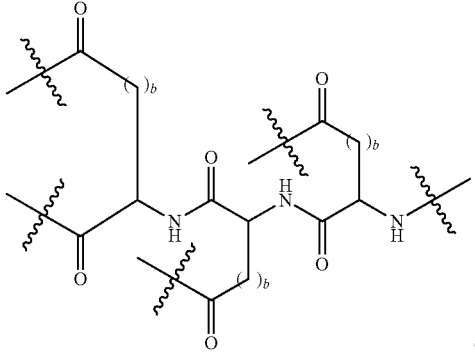

or (EVIIb)

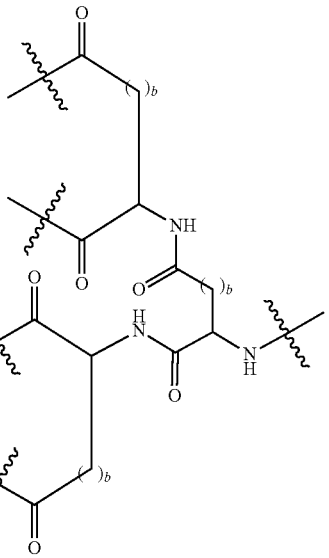

and so on, giving the potential to incorporate many units of the therapeutic agent. As above, each payload unit may be attached to an aspartate/glutamate or similar residue via any suitable linker Lk¹ᵃ.

In a similar way, the amino acids lysine, serine, threonine, cysteine, arginine or tyrosine or similar residues may be introduced to form a branching group, thus:

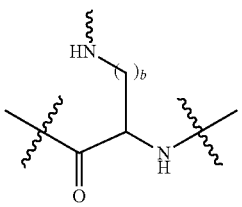

in which b is 4 for lysine, and

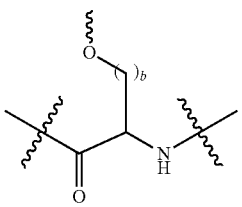

in which b is 1 for serine.

Polymers

The conjugates of the present invention may contain an oligomer or polymer (jointly referred to herein as "polymer" for convenience), together with the antibody or antigen-binding portion thereof according to the invention. For example, the antibody or antigen-binding portion thereof may be conjugated to a polymer via a linker. Alternatively, the linker may itself include a polymer, and this may be conjugated to the antibody or antigen-binding portion thereof. A polymer is especially a water soluble, synthetic polymer, particularly polyalkylene glycol. A polymer may for example be a polyalkylene glycol, a polyvinylpyrrolidone, a polyacrylate, for example polyacryloyl morpholine, a polymethacrylate, a polyoxazoline, a polyvinylalcohol, a polyacrylamide or polymethacrylamide, for example polycarboxymethacrylamide, or a HPMA copolymer. Additionally, the polymer may be a polymer that is susceptible to enzymatic or hydrolytic degradation. Such polymers, for example, include polyesters, polyacetals, poly(ortho esters), polycarbonates, poly(imino carbonates), and polyamides, such as poly(amino acids). A polymer may be a homopolymer, random copolymer or a structurally defined copolymer such as a block copolymer, for example it may be a block copolymer derived from two or more alkylene oxides, or from poly(alkylene oxide) and either a polyester, polyacetal, poly(ortho ester), or a poly(amino acid). Polyfunctional polymers that may be used include copolymers of divinylether-maleic anhydride and styrene-maleic anhydride.

Naturally occurring polymers may also be used, for example polysaccharides such as chitin, dextran, dextrin, chitosan, starch, cellulose, glycogen, poly(sialylic acid), hyaluronic acid and derivatives thereof. Polymers such as polyglutamic acid may also be used, as may hybrid polymers derived from natural monomers such as saccharides or amino acids and synthetic monomers such as ethylene oxide or methacrylic acid.

If the polymer is a polyalkylene glycol, this is preferably one containing $C_2$ and/or $C_3$ units, and is especially a polyethylene glycol. A polymer, particularly a polyalkylene glycol, may contain a single linear chain, or it may have branched morphology composed of many chains either small or large. The so-called Pluronics are an important class of PEG block copolymers. These are derived from ethylene oxide and propylene oxide blocks. Substituted, or capped, polyalkylene glycols, for example methoxypolyethylene glycol, may be used.

The polymer may, for example, be a comb polymer produced by the method described in WO 2004/113394, the contents of which are incorporated herein by reference. For example, the polymer may be a comb polymer having a general formula:

where:
F, where present, is obtainable by addition polymerisation of one or more olefinically unsaturated monomers which are not as defined in G;
G is obtainable by addition polymerisation of a plurality of monomers which are linear, branched, or star-shaped, substituted or non-substituted, and have an olefinically unsaturated moiety;
H, where present, is obtainable by addition polymerisation of one or more olefinically-unsaturated monomers which are not as defined in G;
f and h are an integer between 0 and 500;
g is an integer of 0 to 1000;
wherein at least one of F and G is present.

A polymer may optionally be derivatised or functionalised in any desired way. Reactive groups may be linked at the polymer terminus or end group, or along the polymer chain through pendent linkers; in such case, the polymer is for example a polyacrylamide, polymethacrylamide, polyacrylate, polymethacrylate, or a maleic anhydride copolymer. If desired, the polymer may be coupled to a solid support using conventional methods.

The optimum molecular weight of the polymer will of course depend upon the intended application. Long-chain polymers may be used, for example the number average molecular weight may be up to around 75,000, for example up to 50,000, 40,000 or 30,000 g/mole. For example, the number average molecular weight may be in the range of from 500 g/mole to around 75,000 g/mole. However, very small oligomers, consisting of discrete PEG chains with, for example, as few as 2 repeat units, for example from 2 to 50 repeat units, are useful for some applications, and are present in one preferred embodiment of the invention. For example, the polymer may contain from 2 to 48, for example from 2 to 36, for example from 2 to 24, units may be used. Straight chain or branched PEGs with 12, 20, 24, 36, 40 or 48 repeat units may for example be used. When the conjugate is intended to leave the circulation and penetrate tissue, for example for use in the treatment of inflammation caused by malignancy, infection or autoimmune disease, or by trauma, it may be advantageous to use a lower molecular weight polymer in the range up to 30,000 g/mole. For applications where the conjugate is intended to remain in circulation it may be advantageous to use a higher molecular weight polymer, for example in the range of 20,000-75,000 g/mole.

Preferably the polymer is a synthetic polymer, and preferably it is a water-soluble polymer. The use of a water-soluble polyethylene glycol is particularly preferred for many applications.

Our copending application GB 1418986.4 from which PCT/GB2015/052953 claims priority, published as WO2016/063006, relates to the use of PEG-containing linkers of a particular structure, and these may be used in the present invention. That application discloses the following:

"The invention provides a conjugate of a protein or peptide with a therapeutic, diagnostic or labelling agent, said conjugate containing a protein or peptide bonding portion and a polyethylene glycol portion; in which said protein or peptide bonding portion has the general formula:

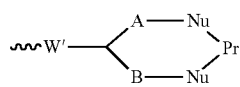

(I)

in which Pr represents said protein or peptide, each Nu represents a nucleophile present in or attached to the protein or peptide, each of A and B independently represents a $C_{1-4}$ alkylene or alkenylene chain, and W' represents an electron withdrawing group or a group obtained by reduction of an electron withdrawing group; and in which said polyethylene glycol portion is or includes a pendant polyethylene glycol chain which has a terminal end group of formula —$CH_2CH_2OR$ in which R represents a hydrogen atom, an alkyl group, for example a $C_{1-4}$ alkyl group, especially a methyl group, or an optionally substituted aryl group, especially a phenyl group, especially an unsubstituted phenyl group.

The invention also provides a conjugating reagent capable of reacting with a protein or peptide, and including a therapeutic, diagnostic or labelling agent and a polyethylene glycol portion; said conjugating reagent including a group of the formula:

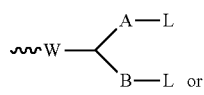

(II)

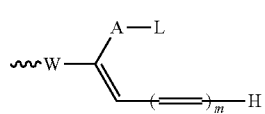

(II')

in which W represents an electron withdrawing group, A and B have the meanings given above, m is 0 to 4, and each L independently represents a leaving group; and in which said polyethylene glycol portion is or includes a pendant polyethylene glycol chain which has a terminal end group of formula —$CH_2CH_2OR$ in which R represents a hydrogen atom, an alkyl group, for example a $C_{1-4}$ alkyl group, especially a methyl group, or an optionally substituted aryl group, especially a phenyl group, especially an unsubstituted phenyl group.

The invention also provides a process for the preparation of a conjugate according to the invention, which comprises reacting a protein or peptide with a conjugating reagent according to the invention.

The conjugate of the invention may be represented schematically by the formula:

(III)

in which D represents the therapeutic, diagnostic or labelling agent, F' represents the group of formula I, and PEG represents the pendant polyethylene glycol chain having a terminal end group of formula —$CH_2CH_2OR$.

The reagent of the invention may be represented schematically by the formula:

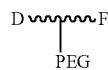

(IV)

in which D represents the therapeutic, diagnostic or labelling agent, F represents the group of formula II or II', and PEG represents the pendant polyethylene glycol chain having a terminal end group of formula —$CH_2CH_2OR$. The functional grouping F is capable of reacting with two nucleophiles present in a protein or peptide as explained below.

A polyethylene glycol (PEG) portion of the conjugates and reagents of the invention is or includes a pendant PEG chain which has a terminal end group of formula —$CH_2CH_2OR$ in which R represents a hydrogen atom, an alkyl group, for example a $C_{1-4}$ alkyl group, especially a methyl group, or an optionally substituted aryl group, especially a phenyl group, especially an unsubstituted phenyl group. Preferably R is a methyl group or a hydrogen atom.

The overall size of the PEG portion will of course depend on the intended application. For some applications, high molecular weight PEGs may be used, for example the number average molecular weight may be up to around 75,000, for example up to 50,000, 40,000 or 30,000 g/mole. For example, the number average molecular weight may be in the range of from 500 g/mole to around 75,000. However, smaller PEG portions may be preferred for some applications.

In one preferred embodiment, all of the PEG in the PEG portion is present in the pendant PEG chain. In another embodiment, PEG may also be present in the backbone of the molecule, and this is discussed in more detail below.

As with the PEG portion, the size of the pendant PEG chain will depend on the intended application. For some applications, high molecular weight pendant PEG chains may be used, for example the number average molecular weight may be up to around 75,000, for example up to 50,000, 40,000 or 30,000 g/mole. For example, the number average molecular weight may be in the range of from 500 g/mole to around 75,000. However, for many applications, smaller pendant PEG chains may be used. For example said PEG chain may have a molecular weight up to 3,000 g/mole. However, very small oligomers, consisting of discrete PEG chains with, for example, as few as 2 repeat units, for example from 2 to 50 repeat units, are useful for some applications, and are present as said PEG chain in one preferred embodiment of the invention. The pendant PEG chain may be straight-chain or branched. PEG chains, for example straight-chain or branched chains with 12, 20, 24, 36, 40 or 48 repeat units may for example be used."

Conjugation Processes

Conjugating reagents containing a functional group capable of reacting with the antibody or antigen-binding portion thereof according to the invention may be reacted with the antibody or antigen-binding portion to form a conjugate, and such a reaction forms a further aspect of the invention. In a preferred embodiment of this further aspect of the invention, a conjugating reagent having one of the structures CI, CI', CII or CIII described above (including all of the preferred sub-structures) is reacted with the antibody or antigen-binding portion thereof to form a conjugate. The immediate product of the conjugation process using one of these reagents is a conjugate which contains an electron-withdrawing group W. However, the conjugation process is reversible under suitable conditions. This may be desirable for some applications, for example where rapid release of the payload is required, but for other applications, rapid release of the payload may be undesirable. It may therefore be desirable to stabilise the conjugates by reduction of the electron-withdrawing moiety W to give a moiety which prevents release of the payload. Accordingly, the process described above may comprise an additional optional step of reducing the electron withdrawing group W in the conjugate. The use of a borohydride, for example sodium borohydride, sodium cyanoborohydride, potassium borohydride or sodium triacetoxyborohydride, as reducing agent is particularly preferred. Other reducing agents which may be used include for example tin(II) chloride, alkoxides such as aluminium alkoxide, and lithium aluminium hydride.

Thus, for example, a moiety W containing a keto group may be reduced to a moiety containing a CH(OH) group; an ether group may be obtained by the reaction of a hydroxy group with an etherifying agent; an ester group may be obtained by the reaction of a hydroxy group with an acylating agent; an amine group may be prepared from a ketone by reductive amination; or an amide may be formed by acylation of an amine. A sulfone may be reduced to a sulfoxide, sulfide or thiol ether. A cyano group may be reduced to an amine group.

A key feature of using conjugating reagents of formula CI or CII described above is that an α-methylene leaving group and a double bond are cross-conjugated with an electron withdrawing function that serves as a Michael activating moiety. If the leaving group is prone to elimination in the cross-functional reagent rather than to direct displacement and the electron-withdrawing group is a suitable activating moiety for the Michael reaction then sequential intramolecular bis-alkylation can occur by consecutive Michael and retro Michael reactions. The leaving moiety serves to mask a latent conjugated double bond that is not exposed until after the first alkylation has occurred to give a reagent of formula CI' and bis-alkylation results from sequential and interactive Michael and retro-Michael reactions. The cross-functional alkylating agents may contain multiple bonds conjugated to the double bond or between the leaving group and the electron withdrawing group.

Where bonding to the antibody or antigen-binding portion thereof is via two sulfur atoms derived from a disulfide bond in the antibody or antigen-binding portion, the process may be carried out by reducing the disulfide bond in situ following which the reduced product reacts with the conjugating reagent having one of the structures C described above. Preferably the disulfide bond is reduced and any excess reducing agent is removed, for example by buffer exchange, before the conjugating reagent is introduced. The disulfide bond can be reduced, for example, with dithiothreitol, mercaptoethanol, or tris-carboxyethylphosphine using conventional methods.

Conjugation reactions may be carried out under similar conditions to known conjugation processes, including the conditions disclosed in the prior art. For example, when using conjugating reagents having one of the structures C described above, the conjugation reaction according to the invention may be carried out under reaction conditions similar to those described in WO 2005/007197, WO 2009/047500, WO2010/100430, WO 2014/064423 and WO 2014/064424. The process may for example be carried out in a solvent or solvent mixture in which all reactants are soluble. For example, the protein may be allowed to react directly with the polymer conjugating reagent in an aqueous reaction medium. This reaction medium may also be buffered, depending on the pH requirements of the nucleophile. The optimum pH for the reaction will generally be at least 4.5, typically between about 5.0 and about 8.5, preferably about 6.0 to 7.5. The optimal reaction conditions will of course depend upon the specific reactants employed.

Reaction temperatures between 3-40° C. are generally suitable when using an aqueous reaction medium. Reactions conducted in organic media (for example THF, ethyl acetate, acetone, acetonitrile, DMF, DMSO) are typically conducted at temperatures up to ambient. In one preferred embodiment, the reaction is carried out in aqueous buffer which may contain a proportion of organic solvent, for example up to 20% by volume of organic solvent, typically from 5 to 20% by volume organic solvent.

The antibody or antigen-binding portion can be effectively conjugated using a stoichiometric equivalent or a slight excess of conjugating reagent. However, it is also possible to conduct the conjugation reaction with an excess of conjugating reagent, and this may be desirable for some proteins. The excess reagent can easily be removed by conventional means, for example ion exchange or HPLC chromatography, during subsequent purification of the conjugate.

Of course, it is possible for more than one conjugating reagent to be conjugated to the antibody or antigen-binding portion, where the antibody contains sufficient suitable attachment points. For example, in an antibody which contains two different disulfide bonds, or in an antibody which contains one disulfide bond and also carries a polyhistidine tag, it is possible to conjugate two molecules of the reagent per molecule of antibody. Antibodies generally contain 4 suitable disulfide bonds, and it is possible by a suitable choice of reaction conditions to conjugate one linker carrying a payload across each disulfide bond. If each linker carries a single payload, this give a conjugate with a drug antibody ratio (DAR) of 4. Additional copies of the payload may be attached by use of branched linkers as described above.

When the antibody or antigen-binding fragment thereof is conjugated to a radioactive metal or paramagnetic ion, then in some embodiments, the radioactive metal or paramagnetic ion can be reacted with a reagent having a long tail with one or more chelating groups attached to the long tail for binding these ions. In some embodiments the reagent may carry a reactive group designed to covalently tether the antibody or antigen-binding portion thereof. The long tail can be a polymer such as a polylysine, polysaccharide, polyethylene glycol (PEG) or other derivatised or derivatisable chain having pendant groups to which may be bound to a chelating group for binding the ions. Examples of chelating groups that may be used according to the embodiments herein include, but are not limited to, ethylenediaminetetraacetic acid (EDTA), diethylenetriaminepentaacetic acid (DTPA), DOTA, NOTA, NODAGA, NETA, deferoxamine (Df, which may also be referred to as DFO), porphyrins, polyamines, crown ethers, bis-thiosemicarbazones, polyoximes, and like groups. The same chelates, when complexed with non-radioactive metals, such as manganese, iron and gadolinium are useful for MRI, when used along with the antibody or antigen-binding portion thereof and carriers described herein. Macrocyclic chelates such as NOTA, NODAGA, DOTA, and TETA are of use with a variety of metals and radiometals including, but not limited to, radionuclides of gallium, yttrium and copper, respectively. Other ring-type chelates such as macrocyclic polyethers, which are of interest for stably binding radionuclides, such as Radium-223 for RAIT may be used. In certain embodiments, chelating moieties may be used to attach a PET imaging agent, such as an Aluminum-$^{18}$F or Zirconium-89 complex, to a targeting molecule for use in PET analysis.

Utility and Compositions

The antibodies and antigen-binding portions thereof of the invention, and the conjugates of the invention, find use in the treatment, prevention or diagnosis of diseases and conditions mediated by PSMA or characterised by increased expression of PSMA. The invention therefore provides an antibody or an antigen-binding portion thereof of the invention or a conjugate of the invention for use in diagnosis or therapy, specifically, for use in diagnosing, treating or preventing a disease or condition mediated by PSMA or characterised by increased expression of PSMA. The invention also provides a method of treating or preventing a disease or condition mediated by PSMA or characterised by increased expression of PSMA, comprising administering an antibody or antigen-binding portion thereof or a conjugate of the invention to a subject in need thereof in an amount effective to treat or prevent the disease or condition. The invention also provides the use of an antibody or an antigen-binding portion thereof or a conjugate according to the invention for use in the manufacture of a medicament for diagnosing, treating or preventing a disease or condition mediated by PSMA or characterised by increased expression of PSMA.

In some embodiments, the PSMA-mediated disease is a cancer, such as prostate cancer or a non-prostate cancer (including the nonprostate cancers described elsewhere herein). A non-prostate cancer preferably is selected from the group consisting of bladder cancer including transitional cell carcinoma; pancreatic cancer including pancreatic duct carcinoma; lung cancer including non-small cell lung carcinoma; kidney cancer including conventional renal cell carcinoma; sarcoma including soft tissue sarcoma; liver cancer, including metastatic adenocarcinoma; breast cancer including breast carcinoma; brain cancer including glioblastoma multiforme; neuroendocrine carcinoma; colon cancer including colonic carcinoma; testicular cancer including testicular embryonal carcinoma; and melanoma including malignant melanoma. The most effective cancer treatments generally require the co-administration of several drugs. It is thus preferred for the active agent of the invention to be administered in combination with at least one further chemotherapeutic agent.

In yet another aspect, the present invention provides a method of using antibodies or antigen-binding portions thereof or conjugates of the invention for detecting in vitro or in vivo the presence of PSMA antigen in a sample, e.g., for diagnosing a PSMA-related disease (for example a human PSMA-related disease). In some methods, this is achieved by contacting a sample to be tested, along with a control sample, with an antibody of the invention or an antigen-binding portion thereof or a conjugate of the invention (including a bispecific or multispecific molecule), under conditions that allow for formation of a complex between the antibody and PSMA. Such an assay can be carried out in vitro. Complex formation is then detected (e.g., by ELISA) in the test samples, and any statistically significant increase in the formation of complexes between the test and control samples is indicative of the presence of PSMA in the test sample.

In other embodiments, the present invention can be used in a method of diagnosing a disease or condition mediated by PSMA or characterised by increased expression of PSMA, comprising administering an antibody or antigen-binding portion thereof or a conjugate of the invention conjugated to a diagnostic agent to a subject having or suspected of having a disease or condition mediated by PSMA or characterised by increased expression of PSMA; exposing the subject to an imaging method to visualise the labelled antibody or antigen-binding portion thereof or the conjugate, and determining that the subject has a disease or condition mediated by PSMA or characterised by increased expression of PSMA.

For in vivo diagnostic purposes, an antibody or antigen-binding portion thereof of the invention is preferably in the form of a conjugate in which the antibody is labelled with a detectable marker, as described above. Detectable markers include radioactive or fluorescent markers. Radiolabels that can be used on the antibody or antigen-binding antibody fragment to be administered include for example actinium ($^{225}$Ac), astatine ($^{211}$At), bismuth ($^{213}$Bi or $^{212}$Bi), carbon ($^{14}$C), cobalt ($^{57}$Co), copper ($^{67}$Cu), fluorine ($^{18}$F), gallium ($^{68}$Ga or $^{67}$Ga), holmium ($^{166}$Ho), indium ($^{115}$In, $^{113}$In, $^{112}$In, or $^{111}$In), iodine ($^{131}$I, $^{125}$I, $^{123}$I, or $^{121}$I), lead ($^{212}$Pb), lutetium ($^{177}$Lu), palladium ($^{103}$Pd), phosphorous ($^{32}$P), platinum ($^{195}$Pt), rhenium ($^{186}$Re or $^{188}$Re), rhodium ($^{105}$Rh), ruthenium ($^{97}$Ru), samarium ($^{153}$Sm), scandium ($^{47}$Sc), technetium ($^{99}$Tc), ytterbium ($^{169}$Yb or $^{175}$Yb), or yttrium ($^{90}$Y). Fluorescent markers suitable for use with antibodies and antibody fragments are also well known in the art.

When labelled with an appropriate radionuclides (e.g., the positron emitter Iodine-124, Copper-64, Fluorine-18, Gallium-68 and/or Zirconium-89 for PET imaging) or fluorophore (for fluorescent imaging), the antibody or antigen-binding portion thereof can be used for preclinical imaging and/or for clinical imaging in patients. The antibody or antigen-binding portion thereof can also be used as potential SPECT imaging agents by simply changing the radiolabel to single photon emitting radionuclides such as Indium-111, Iodine-123 and Lutitium-177.

In another aspect, the present invention provides a pharmaceutical or diagnostic composition which comprises an antibody or an antigen-binding portion thereof according to the invention, or a conjugate according to the invention, together with a pharmaceutically acceptable carrier. The composition may also if desired contain an additional active ingredient.

EXAMPLES

Commercially available reagents referred to in the Examples were used according to manufacturer's instructions unless otherwise indicated. The source of cells within the Examples and throughout the specification is on each occasion identified either by ECACC or ATCC accession numbers. ECACC is the European Collection of Cell Cultures, Salisbury, England, whereas ATCC is the American Type Culture Collection, Manassas, USA. Unless otherwise defined, all technical and scientific terms used herein have the same meaning as commonly understood by one of ordinary skill in the art to which this invention belongs. Exemplary methods and materials are described below although methods and materials similar or equivalent to those described herein can also be used in the practice or testing of the present invention. The materials, methods, and examples are illustrative only and not intended to be limiting in scope.

Example 1: Generation of Antibodies

Five heavy chains and four light chain sequences (designated VH1 to VH5, and VK1 to VK4 respectively) were selected. Their amino acid sequences are SEQ ID Nos 10 to 14 and 15 to 18 respectively and their nucleic acid sequences are SEQ ID Nos 1 to 5 and 6 to 9 respectively. Comparator prior art antibodies were also selected: the heavy and light chain V region sequences of the mJ591 (amino acid sequences SEQ ID Nos 23 and 24 respectively, and nucleic acid Seq IDs 19 and 20 respectively), and of deimmunised J591 (amino acid sequences SEQ ID Nos 25 and 26 respectively, and nucleic acid Seq IDs 21 and 22 respectively).

DNA encoding variant V regions were synthesised and subcloned into pANT antibody expression vectors (FIG. 1a), with heavy and light chain V regions cloned into pANT17.2 and pANT13.2 respectively. Heavy chain V region genes were cloned into pANT17.2 via MluI and HindIII sites in frame with the human γ1 heavy chain gene (G1m3 (G1m(f)) allotype) and light chain V region genes were cloned into pANT13.2 via BssHII and BamHI sites in frame with the human kappa light chain constant region gene (Km3 allotype). Transcription of both heavy and light chain genes was under the control of the CMV I/E promoter (U.S. Pat. Nos. 5,168,062 and 5,385,839, University of Iowa) and the pANT17 plasmid contained a mutant dhfr minigene (Simonsen & Levinson 1983, PNAS 80:2495-2499) under the control of a SV40 promoter and polyA sequence for selection in eukaryotic cells. Both pANT17.2 and pANT13.2 contained a β-lactamase (Ap$^R$) gene for prokaryotic selection and a pMB 1 origin of replication for propagation in prokaryotic cells. All plasmids were propagated in E. coli XL1-blue (Stratagene Cat. No. 200130). The heavy and light chain expression constructs were then stably co-transfected into NS0 cells by electroporation and antibody expressing clones selected by including methotrexate in the growth medium. The chimeric, deimmunised and all combinations of humanised VH and Vκ chains (i.e. a total of 20 pairings for humanised variants of mJ591) were transfected into NS0 cells, and secreted antibodies were purified by protein A chromatography from the culture supernatants as described above.

The antibodies that were prepared are shown in Table 1:

TABLE 1

| Antibody Name | Heavy chain | Light chain |
|---|---|---|
| AB - P1 | SEQ ID No 35 | SEQ ID No 36 |
| AB - P2 | SEQ ID No 37 | SEQ ID No 38 |
| AB - 01 [VH4/VK3] | SEQ ID No 13 | SEQ ID No 17 |
| AB - 02 [VH5/VK3] | SEQ ID No 14 | SEQ ID No 17 |
| AB - 03 [VH4/VK4] | SEQ ID No 13 | SEQ ID No 18 |

TABLE 1-continued

| Antibody Name | Heavy chain | Light chain |
|---|---|---|
| AB - 04 [VH5/VK4] | SEQ ID No 14 | SEQ ID No 18 |
| AB - 05 [VH1/VK1] | SEQ ID No 10 | SEQ ID No 15 |
| AB - 06 [VH1/VK2] | SEQ ID No 10 | SEQ ID No 16 |
| AB - 07 [VH1/VK3] | SEQ ID No 10 | SEQ ID No 17 |
| AB - 08 [VH1/VK4] | SEQ ID No 10 | SEQ ID No 18 |
| AB - 09 [VH2/VK1] | SEQ ID No 11 | SEQ ID No 15 |
| AB - 10 [VH2/VK2] | SEQ ID No 11 | SEQ ID No 16 |
| AB - 11 [VH2/VK3] | SEQ ID No 11 | SEQ ID No 17 |
| AB - 12 [VH2/VK4] | SEQ ID No 11 | SEQ ID No 18 |
| AB - 13 [VH3/VK1] | SEQ ID No 12 | SEQ ID No 15 |
| AB - 14 [VH3/VK2] | SEQ ID No 12 | SEQ ID No 16 |
| AB - 15 [VH3/VK3] | SEQ ID No 12 | SEQ ID No 17 |
| AB - 16 [VH3/VK4] | SEQ ID No 12 | SEQ ID No 18 |
| AB - 17 [VH4/VK1] | SEQ ID No 13 | SEQ ID No 15 |
| AB - 18 [VH4/VK2] | SEQ ID No 13 | SEQ ID No 16 |
| AB - 19 [VH5/VK1] | SEQ ID No 14 | SEQ ID No 15 |
| AB - 20 [VH5/VK2] | SEQ ID No 14 | SEQ ID No 16 |
| AB - 21 [Chimeric] | SEQ ID No 23 | SEQ ID No 24 |
| AB - 22 [Deimmunised] | SEQ ID No 25 | SEQ ID No 26 |

Prior to purification, both the tubing and the Protein A column were depyrogenated using 0.4 M NaOH. The column was re-equilibrated with 20 column volumes of 1×PBS pH 7.4. Cell culture supernatants were harvested, adjusted to 1×PBS pH 7.4 using 10×PBS and filter sterilised. Filtered supernatant was pumped through the column at 0.5 mL/min. The column was washed with 1×PBS pH 7.4 and IgG was eluted using sterile 0.1 M Sodium Citrate pH 3, with 0.9 mL fractions collected and neutralised with 0.1 mL of sterile 1 M Tris-HCl pH 9. Under sterile conditions, the product was buffer exchanged into PBS pH 7.4 to remove any elution buffer. Protein A purified material was subsequently run on a HiLoad™ 26/60 Superdex™ 200 pg preparative SEC column (GE Healthcare) using a modified PBS (20 mM Phosphate, 150 mM NaCl, 20 mM EDTA, pH 7.5) as the mobile phase. Antibody was eluted in the monomeric fraction following which, peak fractions were pooled, concentrated and filter sterilised. After concentration, antibodies were quantified by OD280 nm using an extinction coefficient, Ec (0.1%) based on the predicted amino acid sequence of each antibody.

Example 2: Generation of PSMA Expressing NS0 Cell Lines

Figure 1B:
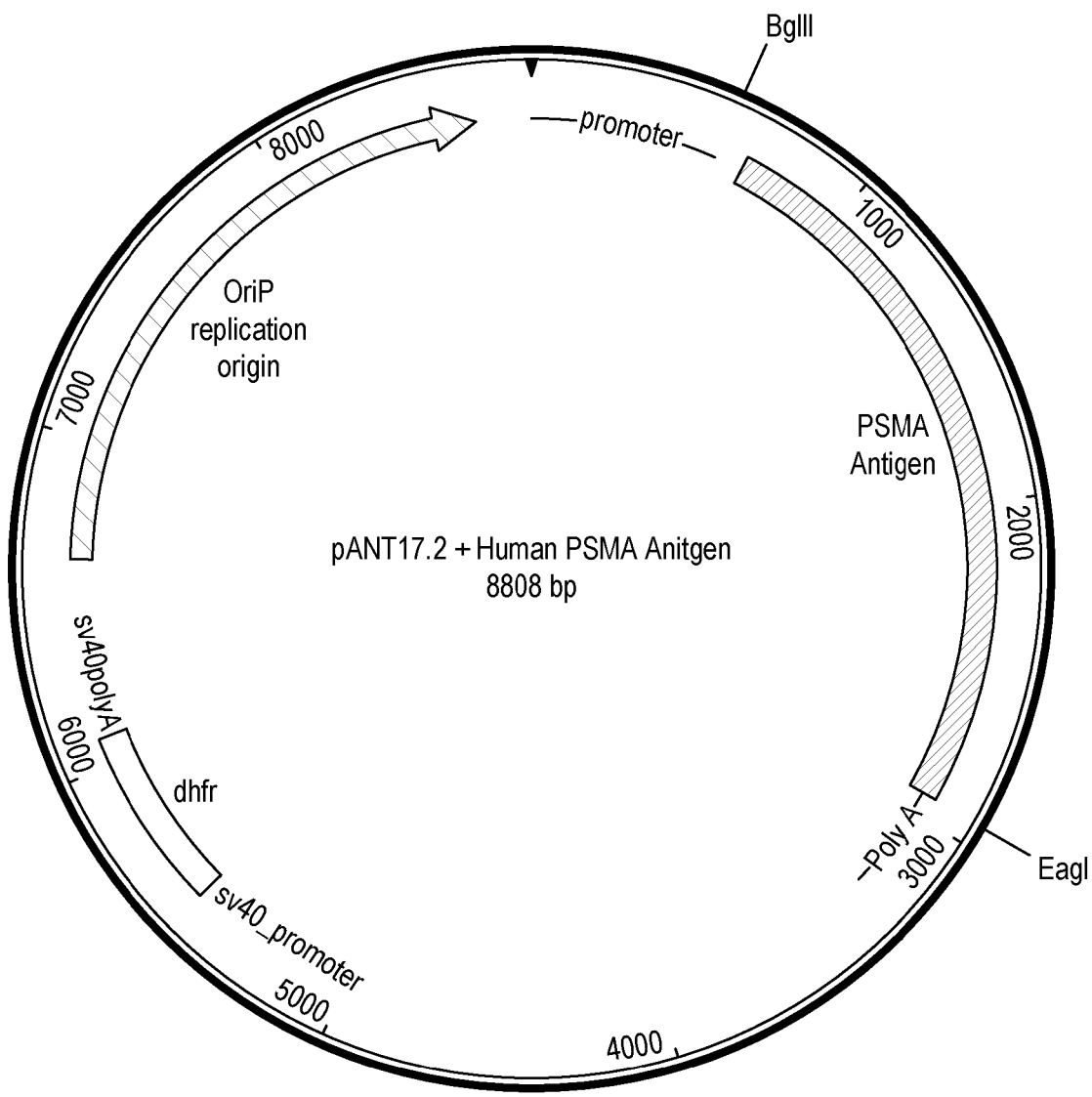

Full length human PSMA antigen (FOLH1_HUMAN ECACC Accession Number Q04609) was codon optimised (DNA SEQ ID No. 31 Amino Acid Seq ID No. 32), synthesised and subcloned into the expression vector pANT17.2 via BglII and EagI sites (removing the IgG1 heavy chain expression cassette) (FIG. 1b). Transcription of the PSMA gene was under the control of the CMV I/E promoter (U.S. Pat. Nos. 5,168,062 and 5,385,839, University of Iowa) and the pANT17.2 plasmid contained a mutant dhfr minigene (Simonsen & Levinson 1983, *PNAS* 80:2495-2499) under the control of a SV40 promoter and polyA sequence for selection in eukaryotic cells. pANT17.2 also contained a β-lactamase (Ap$^R$) gene for prokaryotic selection and a pMB 1 origin of replication for propagation in prokaryotic cells. All plasmids were propagated in E. coli XL1-blue (Stratagene Cat. No. 200130). The PSMA expression construct was then stably co-transfected into NS0 cells by electroporation and PSMA expressing clones selected for by including methotrexate in the growth medium. PSMA expressing clones were analysed by a FACS based assay.

DNA encoding a control PSMA binding antibody (Deimmunised J415-Seq IDs 27-30) was synthesised and subcloned into the expression vectors pANT17.2 and pANT13.2 as described previously (see U.S. Pat. No. 7,045,605). The heavy and light chain expression constructs were then stably co-transfected into NS0 cells by electroporation and antibody expressing clones selected by including methotrexate in the growth medium. Secreted antibody was purified from the cell culture supernatants by Protein A chromatography. Purified antibody was used to assess the PSMA expression of transfected NS0 cell lines as described below.

Figure 2:
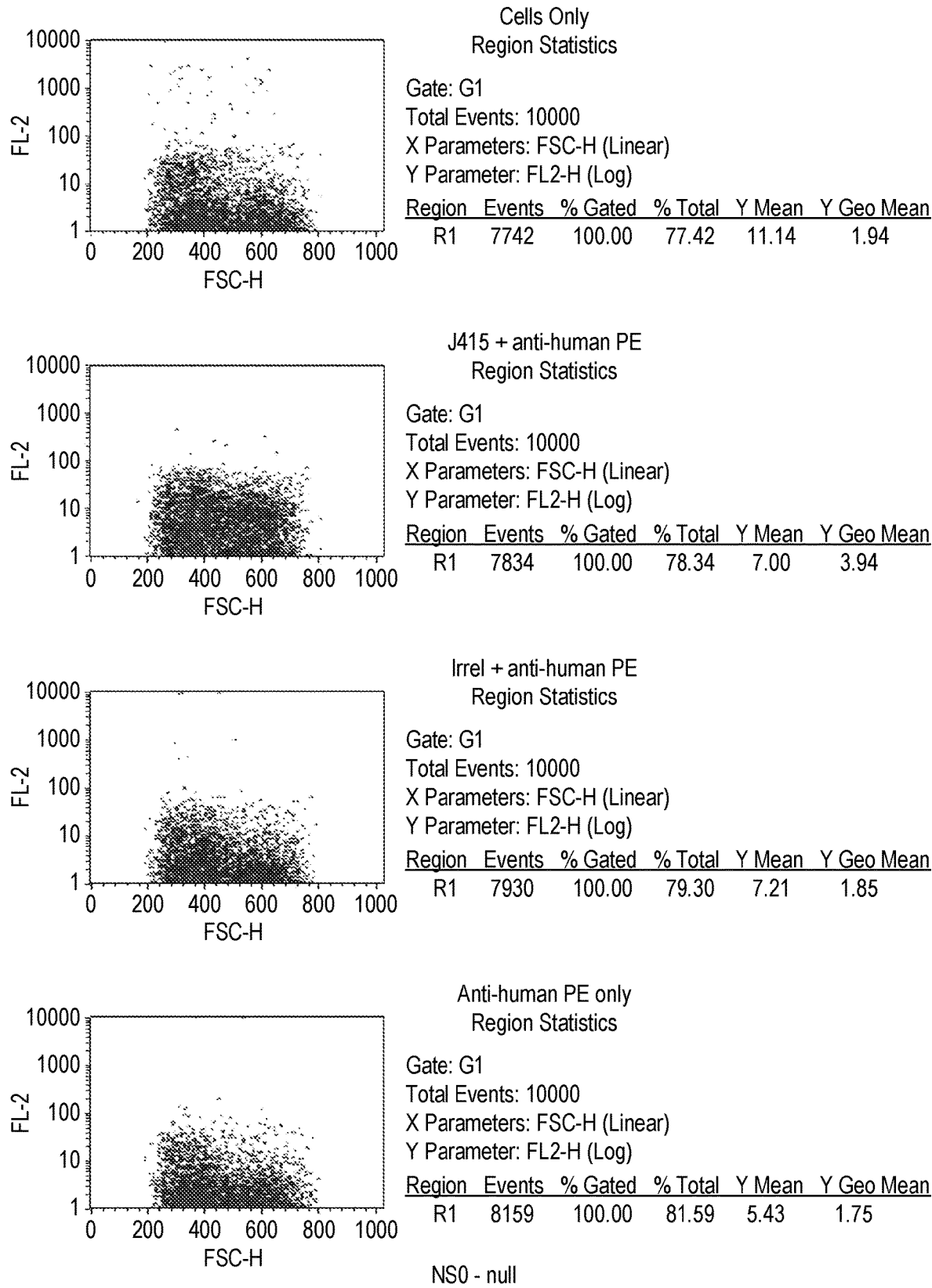
FIG. 2 shows expression of PSMA in a transfected cell line.
Figure 2:
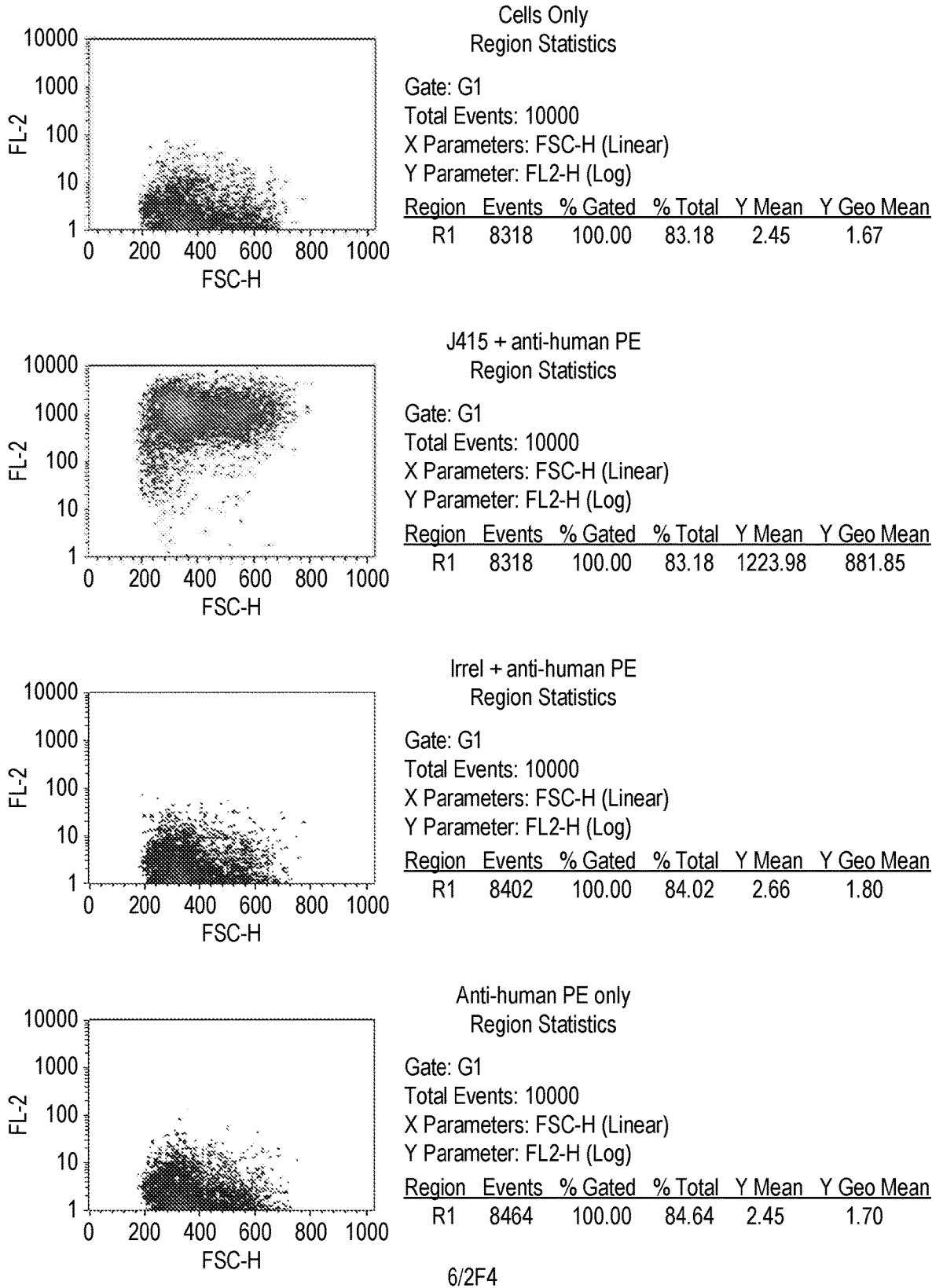

The expression of PSMA antigen on NS0 cells was assessed in a FACS binding ELISA using deimmunised J415 as a reference antibody. Null expressing or PSMA expressing NS0 cells ($5 \times 10^5$ cells per staining) were harvested, washed once with Dulbecco's PBS (PAA Laboratories, Yeovil, UK), resuspended in blocking buffer (PBS containing 1% BSA/0.05% sodium azide, 2.5% goat serum) and incubated at room temperature for 30 minutes. Blocked cells were then resuspended in a 50 μL well of either deimmunised J591 (5 μg/mL) or an isotype matched negative control (5 μg/mL) diluted in FACS buffer (PBS containing 1% BSA/0.05% sodium azide) and incubated on ice for 1 hour. Following incubation, cells were washed 2× with FACS buffer and then resuspended in 50 ul/well of anti-human-PE (Sigma) diluted 1:100 in FACS buffer and incubated on ice for 1 hour. Following incubation, cells were washed 2× with FACS buffer, transferred to FACS tubes and analysed on a Becton Dickinson (Becton Dickinson, Oxford, UK) FACScalibur instrument, collecting 15000 events per tube. As shown in FIG. 2, a lead cell line (6/2F4) was identified which demonstrated significant PSMA expression when compared with the untransfected null cell line.

Example 3: Analysis of Humanised Antibodies

Figure 3:
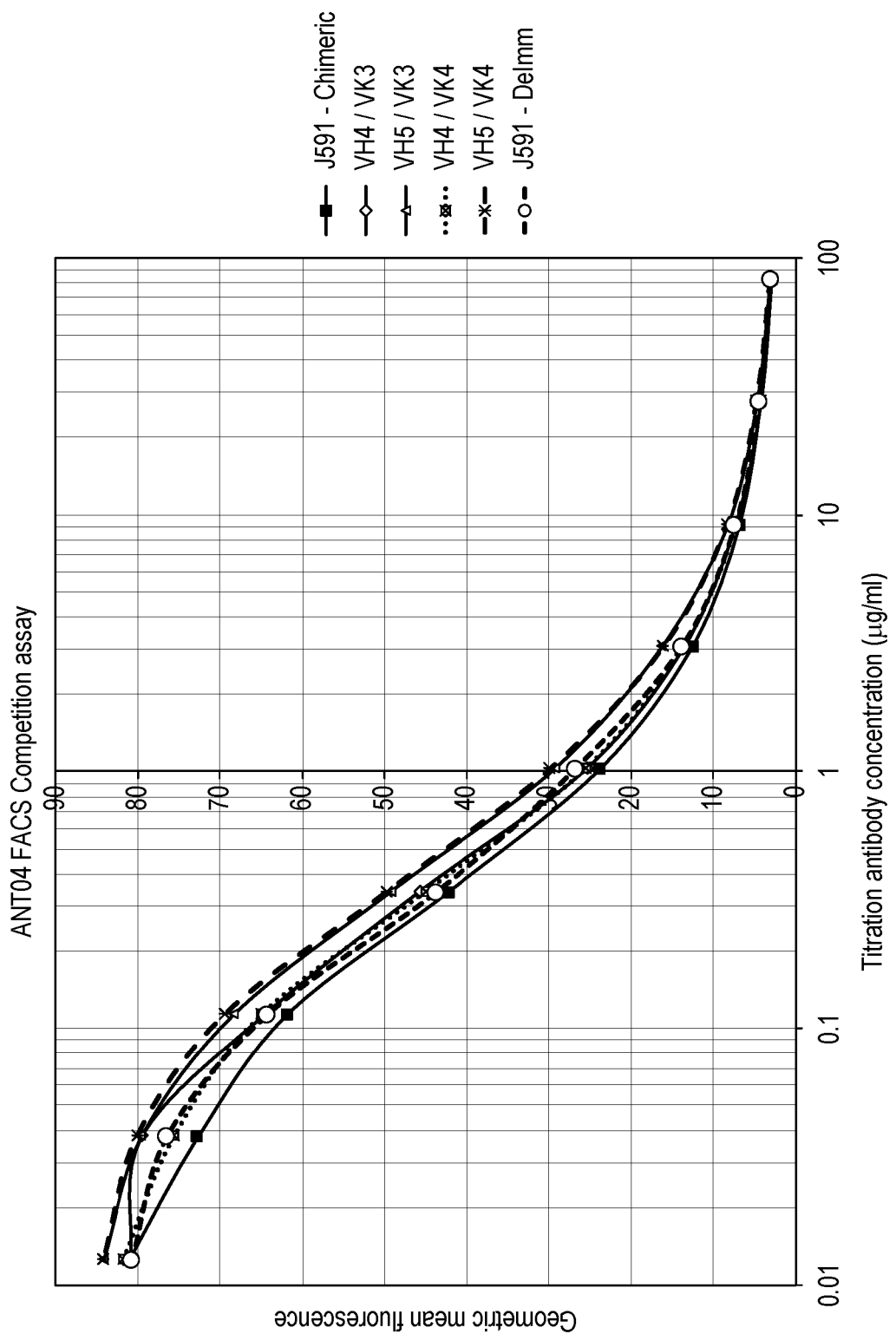
FIG. 3 shows the competitive binding of antibodies of the invention and antibodies of the prior art to PSMA antigen as analysed by FACS.

The binding of NS0-derived J591 variants to PSMA antigen was assessed in a competition FACS ELISA against the parent chimeric J591 and the deimmunised J591 reference antibodies. The deimmunised J591 antibody was fluorescently labelled using the AlexaFluor 488 antibody labelling kit (Molecular Probes, Paisley, UK). PSMA expressing NS0 cells (Clone 6/2F4, $3 \times 10^5$ cells per staining) were harvested, washed once with Dulbecco's PBS (PAA Laboratories, Yeovil, UK), resuspended in blocking buffer (PBS containing 1% BSA/0.05% sodium azide, 2.5% goat serum) and incubated at room temperature for 30 minutes. Test humanised antibodies at various concentrations were pre-mixed with a constant concentration of Alexa-fluor 488 labelled deimmunised J591 antibody (0.5 μg/mL final concentration). Blocked cells were then resuspended in 150 μL/well of the pre-diluted antibody mixes and incubated on ice for 1 hour. Following incubation, cells were washed 2× with PBS containing 1% BSA/0.05% sodium azide, transferred to FACS tubes and analysed on a Becton Dickinson (Becton Dickinson, Oxford, UK) FACScalibur instrument, collecting 15000 events per tube. Data was analysed by plotting the geometric mean fluorescence intensity against test antibody concentration. As shown in FIG. 3, all lead humanised PSMA variants displayed competitive binding profiles similar to the mJ591 chimeric and deimmunised antibodies.

Example 4: Synthesis of Conjugation Reagents Comprising Auristatin Cytotoxic Payloads

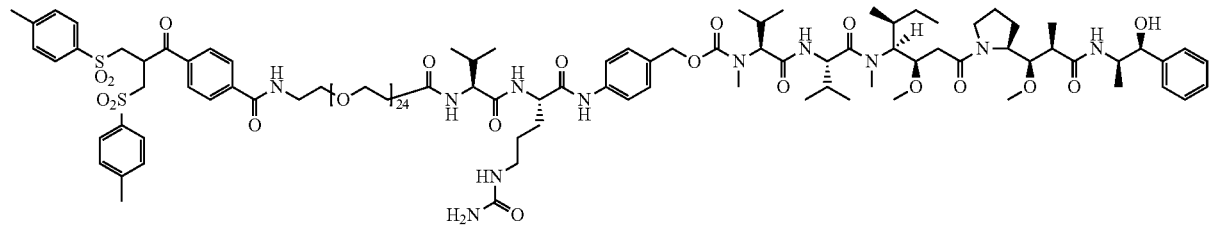

1

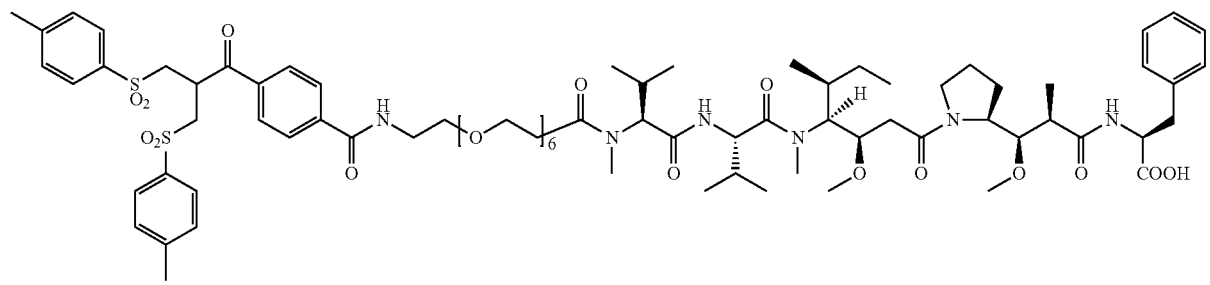

2

Bis-sulfone reagents 1 and 2 were prepared as described within WO2014064423. Reagent 2 was prepared in an analogous way to reagent 1 using a bis-sulfide form which was oxidised to bis-sulfone once the MMAF was attached.

Example 5: Synthesis of a Conjugation Reagent Comprising a Maytansine Cytotoxic Payload

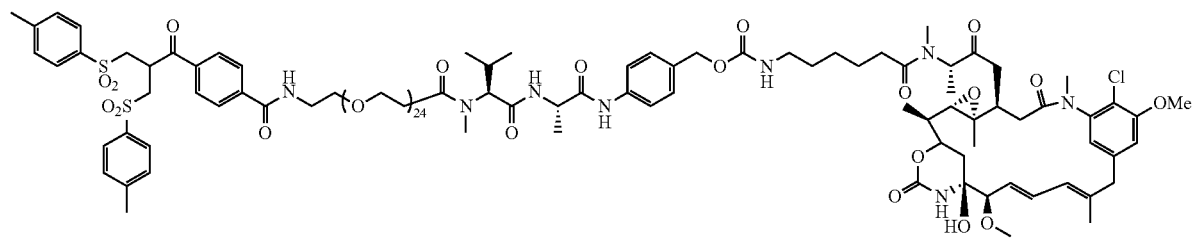

5

Bis-sulfone PEG(24)-val-ala-PAB-AHX-DM1 conjugation reagent 5 was prepared in an analogous way to reagent 1 of Example 4, as described within WO2014064424, via the coupling of bis-sulfone-PEG(24)-acid to val-ala-PAB-AHX-DM1.

Example 6: Synthesis of Conjugation Reagent 7 Comprising a Maytansine Cytotoxic Payload 1(54), 2241-2252) in dimethylformamide (DMF, 70 mL) was added alpha-methoxy-omega-mercapto hepta(ethylene glycol) (3.20 g) and triethylamine (2.50 mL). The resulting reaction mixture was stirred under an inert nitrogen atmosphere at room temperature. After 19 h, volatiles were removed in vacuo. The resulting residue was dissolved in water (2.4 mL) and purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give compound 8 as a thick clear colourless oil (1.77 g). m/z [M+H]$^+$ 901.

7

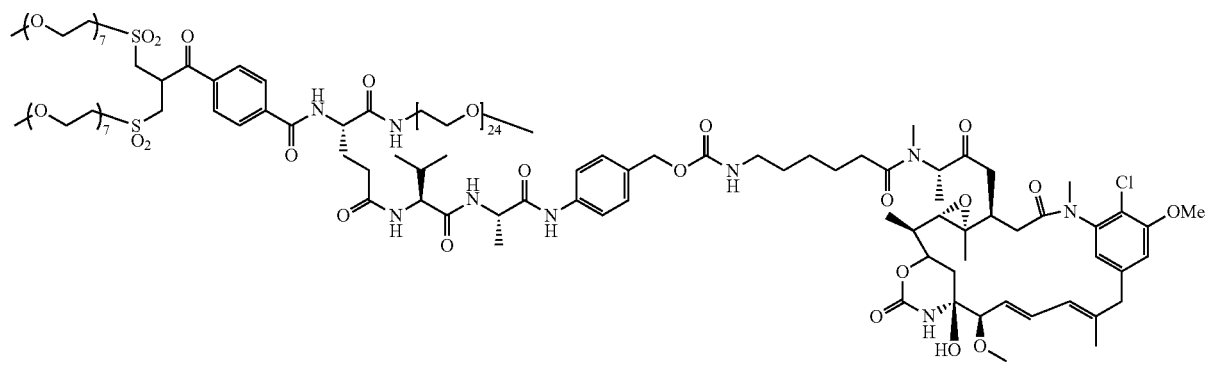

Step 1: Synthesis of compound 8

Step 2: Synthesis of Reagent 9

8

To a stirred solution of 4-[2,2-bis[(p-tolylsulfonyl)-methyl]acetyl]benzoic acid (1.50 g, *Nature Protocols*, 2006,

9

To a stirred solution of 8 (1.32 g) in methanol:water (18 mL, 9:1 v/v) at room temperature was added Oxone® (2.70 g). After 2.5 h, the volatiles were removed in vacuo. The resulting residue was dissolved in dichloromethane (3×10 mL), filtered through a column of magnesium sulfate and washed with dichloromethane (2×7 mL). The eluent and washings were combined and the volatiles were removed in vacuo to give a thick clear pale yellow oil 1.29 g. A portion of the residue (700 mg) was dissolved in water:acetonitrile (1.50 mL, 3:1 v/v), and purified by reverse phase C18-column chromatography eluting with buffer A (v/v): water: 5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give reagent 9 as a thick clear colourless oil (524 mg). m/z [M+H]$^+$ 965.

Step 3: Synthesis of Compound 10.

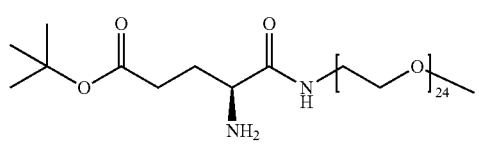

A solution of Fmoc-L-Glu-(OtBu)-OH (36 mg) in DMF (2 mL) was cooled to 0° C. under an argon atmosphere and (benzotriazol-1-yloxy)tris-(dimethylamino) phosphonium hexafluorophosphate (BOP) (41 mg) was added, followed by NH$_2$—PEG(24u)-OMe (100 mg) and N,N-diisopropylethylamine (DIPEA) (19 μL). The solution was allowed to warm to room temperature and after 22 h the volatiles were removed in vacuo. The resulting residue was dissolved in dichloromethane (1 mL) and purified by normal phase column chromatography eluting with dichloromethane: methanol (100:0 v/v to 80:20 v/v). The organic solvent was removed in vacuo to give Fmoc-L-Glu-[OtBu]-[PEG(24u)-OMe] as a colourless oil (84 mg). Piperidine (49 μL) was added to a solution of compound Fmoc-L-Glu-[OtBu]-[PEG(24u)-OMe] (74 mg) in DMF (2 mL) under an argon atmosphere and the resulting solution stirred at room temperature for 22 h, after which the volatiles were removed in vacuo. The resulting residue was triturated with hexane (3×0.7 mL). The organic solvent was decanted each time and the resulting residue dried in vacuo to give compound 10 as a white solid (61 mg). m/z [M+H]$^+$ (1274, 70%), [M+2H]$^{2+}$ (638, 100%).

Step 4: Synthesis of compound 11.

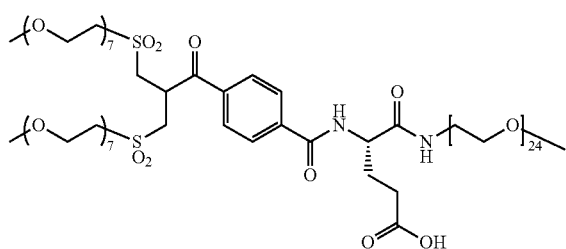

A solution of compound 9 (26.6 mg) in DMF (550 μL) was cooled to 0° C. under an argon atmosphere to which HATU (10.5 mg) was added and the solution stirred for 0.5 h at 0° C. To this was added a solution of reagent 10 (32 mg) in DMF (550 μL). The resulting solution was stirred for 5 min at 0° C. before addition of NMM (2.9 μL) and HATU (10.5 mg). The reaction solution was allowed to stir at 0° C. for 2 h before being warmed to room temperature and stirred for a further 3.5 h. After this time the volatiles were removed in vacuo. The resulting residue was dissolved in water and acetonitrile (v/v; 1/1, 1.2 mL), and purified by reverse phase C18-column chromatography eluting with buffer A (v/v): water:5% acetonitrile:0.1% formic acid and buffer B (v/v): acetonitrile:0.1% formic acid (100:0 v/v to 0:100 v/v). The organic solvent was removed in vacuo and the aqueous solvent removed by lyophilisation to give bis-mPEG(7u) sulfone-propanoyl-benzamide-Glu-[OtBu]-[PEG(24u)-OMe] as a colourless oil (30.5 mg, 55%). $^1$H NMR (400 MHz, MeOH-∂$_4$) 8.19 (2H, d), 8.04 (2H, d), 4.83-4.71 (1H, m), 4.58 (1H, dd), 3.92-3.83 (6H, m), 3.78-3.56 (140H, m), 3.57-3.51 (6H, m), 3.40 (4H, dd), 3.36 (3H, s), 3.35 (6H, s), 2.41 (2H, t), 2.24-2.13 (1H, m), 2.10-1.98 (1H, m), 1.45 (9H, s); m/z [M+Na]+(2243, 50%), [M+H]$^+$ (2221, 40%), [M+Na+2H]$^{3+}$ (747, 100%). A solution of bis-mPEG(7u) sulfone-propanoyl-benzamide-Glu-[OtBu]-[PEG(24u)-OMe] (30 mg) in dichloromethane (2 mL) under an argon atmosphere was cooled to 0° C. to which trifluoroacetic acid (500 μL) was added and the resulting solution stirred for 1.5 h. The reaction mixture was allowed to warm to room temperature and stirred for a further 1 h. After this time the volatiles were removed in vacuo. The resulting residue was dissolved in water and acetonitrile (v/v; 1/1, 0.6 mL), and purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent removed by lyophilisation to give compound 11 as a colourless oil (20 mg). $^1$H NMR (400 MHz, MeOH-∂$_4$) 8.19 (2H, d), 8.04 (2H, d), 4.81-4.72 (1H, m), 4.59 (1H, dd), 3.92-3.84 (6H, m), 3.67-3.50 (146H, m), 3.40 (4H, dd), 3.36 (3H, s), 3.35 (6H, s), 2.48 (2H, t), 2.26-2.15 (1H, m), 2.15-2.03 (1H, m); m/z [M+H]+(2165, 55%), [M+2H]2+(1083, 60%), [M+2H+Na]$^{3+}$ (729, 100%).

Step 5: Synthesis of Reagent 7

A solution of compound 11 (15.0 mg) in DMF (600 μL) was cooled to 0° C. under an argon atmosphere. HATU (2.9 mg) was added and the solution stirred for 0.5 h at 0° C. To this was added a solution of val-ala-PAB-AHX-DM1 (Concortis/Levena Biopharma, 9.2 mg) and NMM (0.8 μL) in DMF (600 μL), which had been stirred at room temperature for 0.5 h. After 5 min, an additional amount of HATU (2.9 mg) and NMM (0.8 μL) was added and the reaction mixture stirred at 0° C. After 3 h, an additional amount of HATU (0.7 mg) was added and the reaction mixture stirred at 0° C. After a further 2 h, the reaction was stored at −20° C. for 16 h. The reaction solution was concentrated in vacuo and purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent removed by lyophilisation to give the reagent 7 as a thick clear colourless oil (14.3 mg). $^1$H NMR (600 MHz, MeOH-∂$_4$) (selected characteristic signals) 5.69 (1H, dd,), 6.59 (1H, dd), 6.68 (1H, s), 6.69 (1H, d), 7.10 (1H, s), 7.28 (2H, d), 7.57 (2H, d), 8.01 (2H, d), 8.16 (2H, d).

Example 7: Synthesis of Conjugation Reagent 12 Comprising an Auristatin Cytotoxic Payload

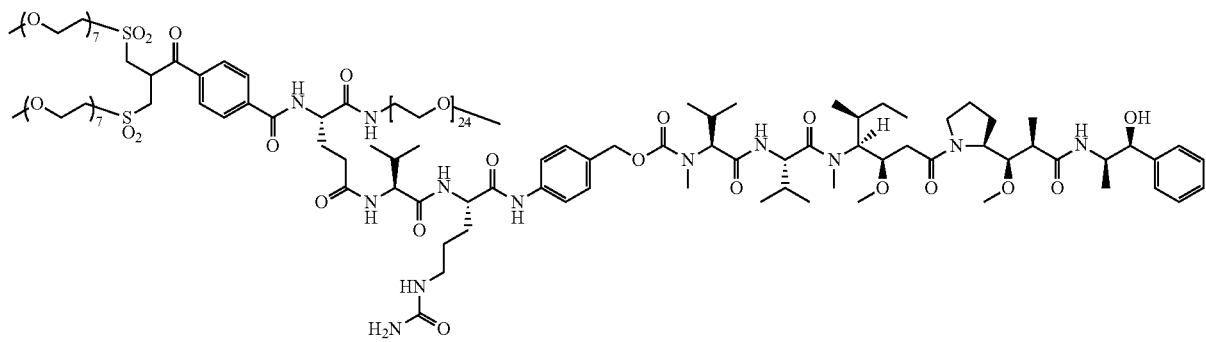

12

Reagent 12 was synthesised in analogous way to reagent 1 of Example 4 from compound 11 and val-cit-PAB-MMAE TFA salt (Concortis/Levena Biopharma) having the structure below:

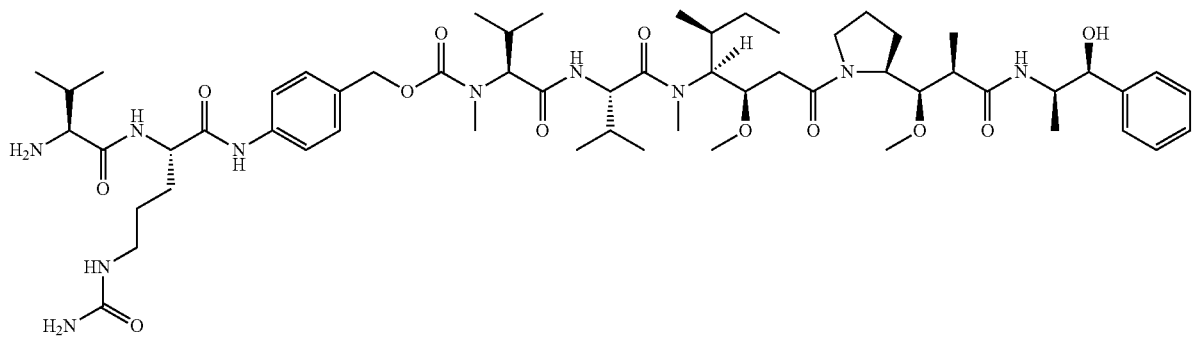 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](N)C(C)C)cc1)C(C)C]

Reagent 12 was isolated as a colourless oil. m/z [M+H]$^+$ (3270, 12%), [M+2H]$^{2+}$ (1636, 50%), [M+3H]$^{3+}$ (1091, 100%).

Example 8: Synthesis of Conjugation Reagent 13 Comprising an Auristatin Cytotoxic Payload

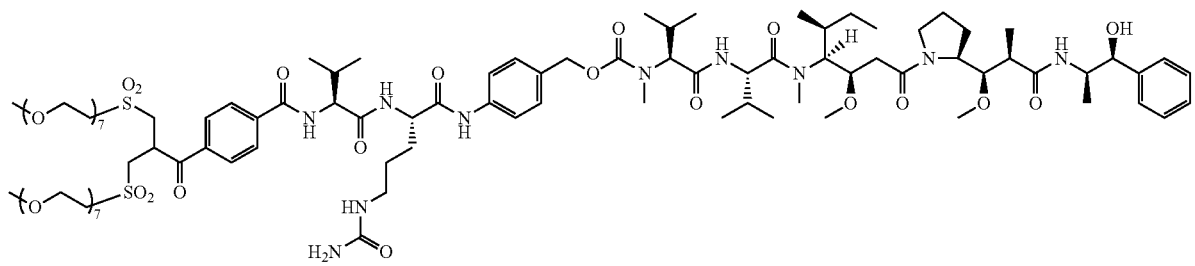

13

To the TFA salt of val-cit-PAB-MMAE salt (25.0 mg) was added a solution of reagent 9 (15.6 mg) in DMF (1.5 mL) and stirred under an inert nitrogen atmosphere at room temperature for 5 min. The mixture was cooled to 0° C. and aliquots of HATU (6.1 mg) and NMM (1.8 µL) were added every 20 min for a total of 5 additions. After 1.5 h, the reaction mixture was warmed to room temperature. After 2 h, volatiles were removed in vacuo. The resulting residue was dissolved in water and acetonitrile (v/v; 1/1, 0.6 mL), and purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give reagent 13 as a white powder (22.4 mg). m/z [M+2H]$^{2+}$ 1035.

Example 9: Synthesis of Conjugation Reagent 14 Comprising an Auristatin Cytotoxic Payload

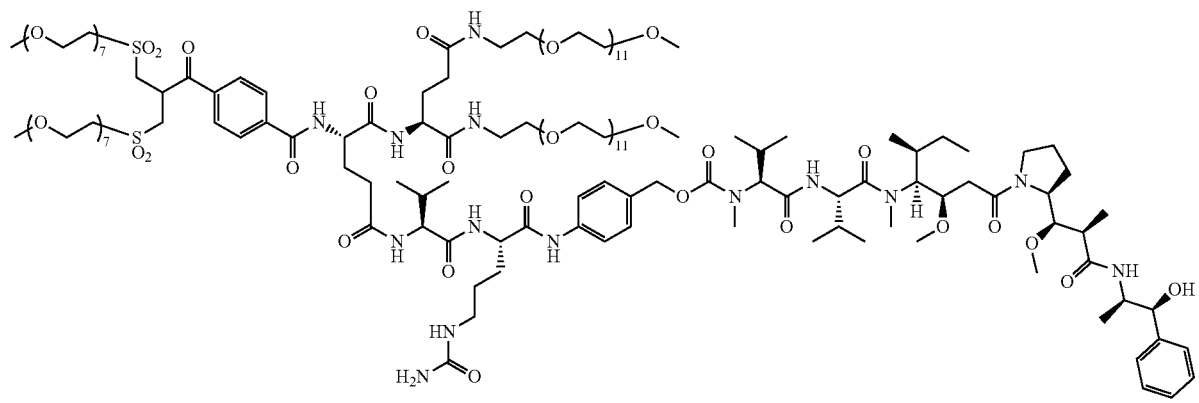

14

Step 1: Synthesis of compound 15.

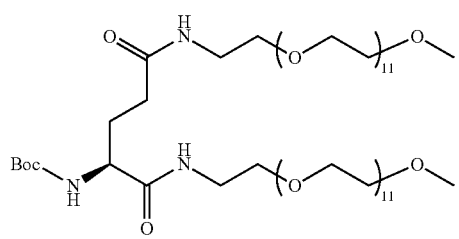

15

Boc-L-Glu (134.9 mg) and BOP (724 mg) were dissolved in anhydrous DMF (4 mL) and were stirred at 0° C. under a nitrogen atmosphere. This solution was then added to a solution of H₂N-PEG(12u)-Me (685 mg) and NMM (179.8 µL) in DMF (3 mL), which had previously been stirred for 75 min. The combined solution was then stirred under nitrogen at 0° C. for 4.5 h. Additional BOP (241 mg) and NMM (60 µL) were added and the reaction mixture left for 24 h at 4° C. The volatiles were removed in vacuo and the resulting residue was purified by reverse phase C18-column chromatography eluting with eluting with buffer A (v/v): water:5% acetonitrile:0.1% formic acid and buffer B (v/v): acetonitrile:0.1% formic acid (100:0 v/v to 65:35 v/v). The organic solvent was removed in vacuo and the aqueous solvent was removed by lyophilisation. The material was repurified by normal phase flash chromatography eluting with ethyl acetate:methanol (100:0 v/v to 0:100 v/v). The organic solvent was removed in vacuo and the aqueous solvent was removed by lyophilisation to give compound 15 as a colourless oil (450 mg). m/z [M+H]⁺ (1331, 100%), [M+2H]²⁺ (666, 100%).

Step 2: Synthesis of Compound 16.

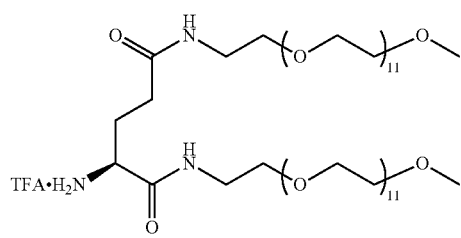

16

Compound 15 (450 mg) was dissolved in dichloromethane (25 mL) to which was added trifluoroacetic acid (2.5 mL). The solution stirred at room temperature for 5 h. After which the volatiles were removed in vacuo. The resulting residue was purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 60:40 v/v). The organic solvent was removed in vacuo and the aqueous solvent was removed by lyophilisation to give compound 16 as a clear colourless solid (320 mg). m/z [M+Na]⁺ (1253, 10%) [M+H]²⁺ (617, 100%)

Step 3: Synthesis of Compound 17.

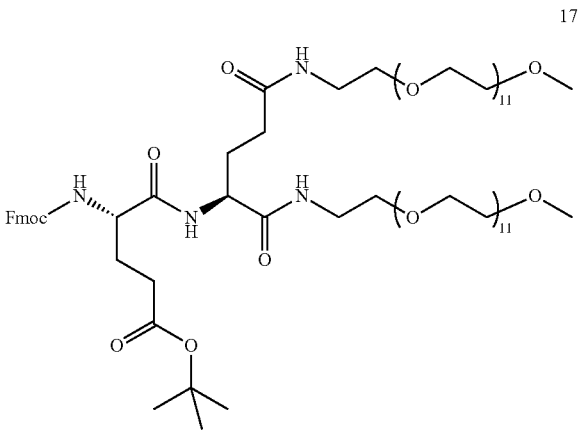

17

To a stirred solution of Fmoc-L-Glu-(OtBu)-OH (36.6 mg) in anhydrous DMF (2 mL) was added HATU (37.30 mg). The reaction mixture was stirred at 0° C. under a nitrogen atmosphere for 1 h and then added to a solution of compound 16 (103.5 mg) and NMM (19.2 µL) in DMF (1 mL). Additional DMF (1 mL) was added. The stirred reaction was left to warm to room temperature over 5 h. The volatiles were removed in vacuo. The resulting pale yellow oil was purified by reverse phase C18-column chromatography eluting with buffer A (v/v): water:5% acetonitrile:0.1% formic acid and buffer B (v/v): acetonitrile:0.1% formic acid (100:0 v/v to 50:50 v/v). The organic solvent was removed in vacuo and the aqueous solvent was removed by lyophilisation to give compound 17 as a white solid (173 mg). m/z [M+H]⁺ (1638, 100%), [M+Na]⁺ (1661, 60%).

Step 4: Synthesis of Compound 18.

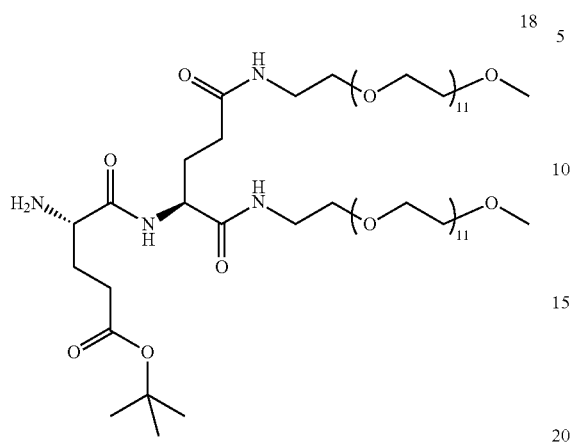

To a stirred solution of compound 17 (173 mg) in anhydrous DMF (3.2 mL) was added piperidine (104.4 µL). The solution was stirred at room temperature under argon for 1.5 h. The volatiles were removed in vacuo and the residue triturated repeatedly with hexane (5×10 mL). The product was dried in vacuo to give compound 18 (152 mg) as a clear colourless oil. m/z [M+H]$^+$ (1417, 85%), [M+2H]$^{2+}$ (709, 100%), [M+Na]$^+$ (1439, 30%)

Step 5: Synthesis of Compound 19.

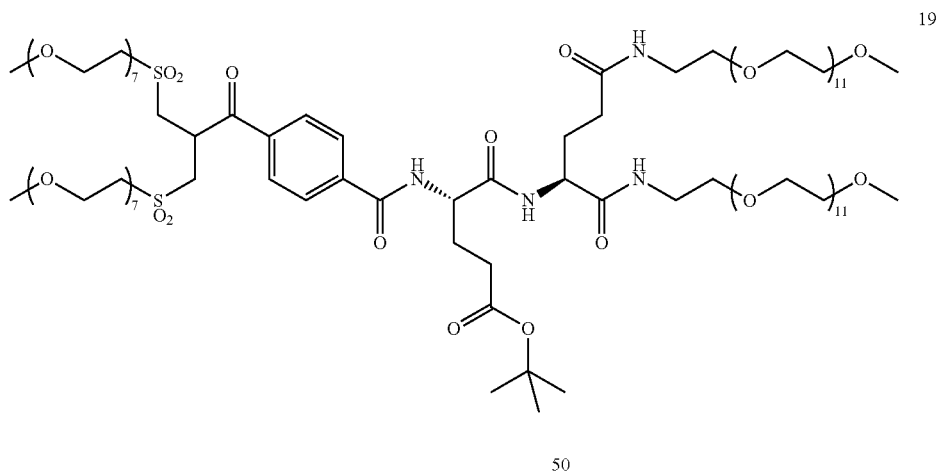

To a stirred solution of compound 9 (114 mg) in anhydrous DMF (3 mL) was added HATU (51.4 mg). The reaction mixture was stirred at 0° C. for 0.5 h then added to a solution of compound 18 (152.0 mg) in DMF (3 mL), followed by NMM (14.8 µL). The reaction mixture was stirred in an ice bath for 3.5 h after which the volatiles were removed in vacuo. The resulting residue was purified by reverse phase C18-column chromatography eluting with buffer A (v/v): water:5% acetonitrile:0.1% formic acid and buffer B (v/v): acetonitrile:0.1% formic acid (100:0 v/v to 55:45 v/v). The organic solvent was removed in vacuo and the aqueous solvent was removed by lyophilisation to give compound 19 as a clear colourless oil (160.6 mg). m/z [M+H]$^+$ (2367, 95%), [M+2H]$^{2+}$ (1184, 80%).

Step 6: Synthesis of Compound 20.

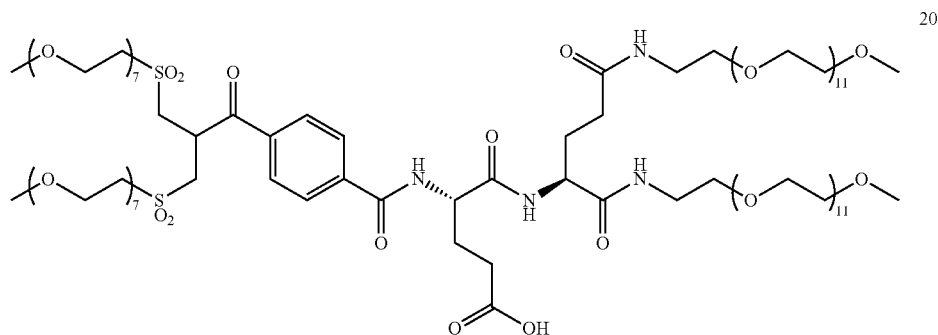

To the stirred solution of compound 19 (156 mg) in anhydrous dichloromethane (6 mL) was added trifluoroacetic acid (6 mL). The reaction mixture was stirred at room temperature for 2 h, after which the volatiles were removed in vacuo, the residue dissolved in water (25 mL) and lyophilised to give compound 20 as a clear colourless oil (156 mg). m/z [M+H]$^+$ (2307, 90%), [M+2H]2+(1153, 100%).

Step 7: Synthesis of Reagent 14.

Reagent 14 was synthesised in analogous way to reagent 1 of Example 4 from compound 20 and val-cit-PAB-MMAE TFA salt. Reagent 14 was isolated as a colourless oil. m/z [M+H](3410, 40%), [M+2H]2+(1706, 60%), [M+3H]$^{3+}$ (1137, 85%), [M+4H]$^{4+}$ (854, 70%).

Example 10: Synthesis of Conjugation Reagent 21 Comprising an Auristatin Cytotoxic Payload

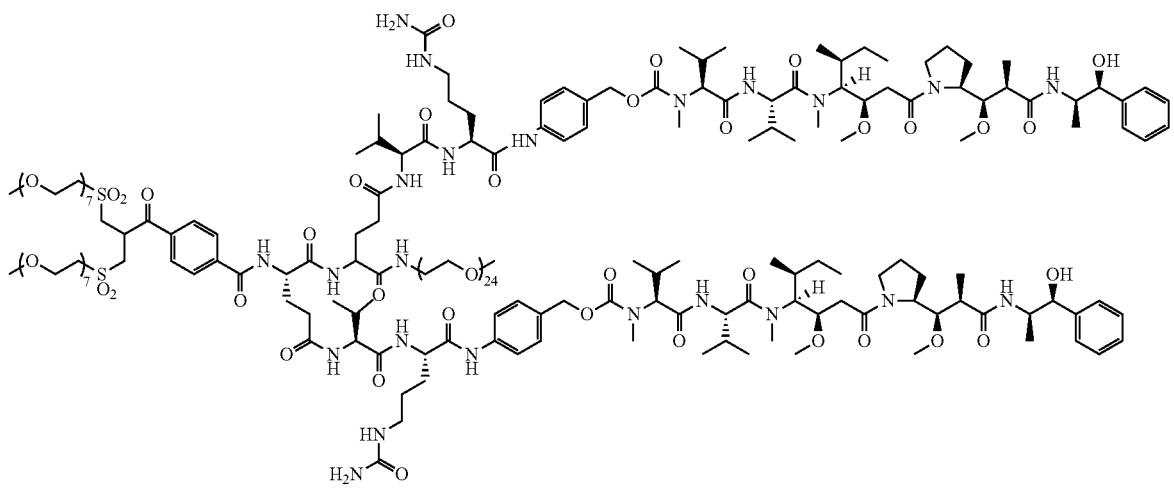

Step 1 Synthesis of Compound 22.

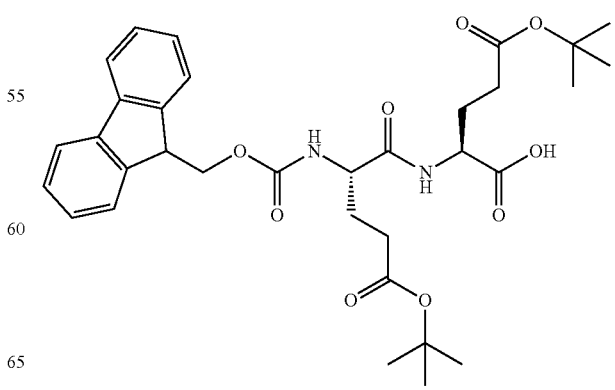

To a stirred solution of Fmoc-L-Glu-(OtBu)-OH (2 g) in anhydrous DMF (18 mL) was added HOBt (666 mg) and N,N'-diisopropylcarbodiimide (DIC) (768 μL). The reaction mixture was stirred at 0° C. for 10 min and then 2.5 h at room temperature. H-L-Glu-(OtBu)-OH (1.19 g) and DIPEA (2.46 mL) were added and the reaction mixture was stirred for 18 h at room temperature. The reaction mixture was diluted with water (100 mL) and acidified to pH 2.0 by adding dilute hydrochloric acid. The aqueous layer was extracted with ethyl acetate (3×100 mL), and the organic phases combined and washed with water (2×50 mL) and saturated brine solution (1×50 mL). The ethyl acetate layer was dried over sodium sulfate for 2 h, filtered and the filtrate concentrated in vacuo. The product was isolated by reverse phase C18-column chromatography eluting with buffer A (v/v): water: 5% acetonitrile: 0.1% formic acid and buffer B (v/v): acetonitrile: 0.1% formic acid (100:0 v/v to 80:20 v/v). The organic solvent was removed in vacuo and the aqueous solvent was removed by lyophilisation to give compound 22 as a white solid (875 mg). m/z [M+H]$^+$ (611, 85%), [M+Na]$^+$ (633, 55%), [2M+Na]$^+$ (1243, 55%).

Step 2: Synthesis of Compound 23.

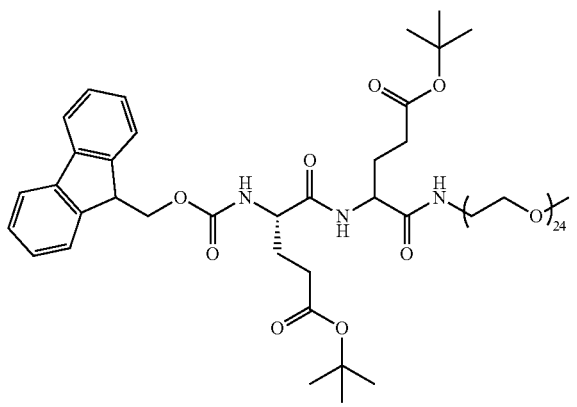

23

To a stirred solution of compound 22 (510 mg) and NH$_2$—PEG(24u)-OMe (1 g) in anhydrous DMF (5 mL) was added DIPEA (43.8 μL) and HATU (47.6 mg). The reaction mixture was stirred at 0° C. for 10 min and then 16 h at room temperature. The solution was concentrated in vacuo to 2 mL and purified by reverse phase C18-column chromatography eluting with buffer A (v/v): water:5% acetonitrile: 0.1% formic acid and buffer B (v/v): acetonitrile:0.1% formic acid (100:0 v/v to 83:17 v/v). The organic solvent was removed in vacuo and the aqueous solvent was removed by lyophilisation to give compound 23 as a white solid (644 mg). m/z [M+H]$^+$ (1681, 40%), [M+Na]$^+$ (1703, 30%) and [M+2H]2$^+$ (841, 55%).

Step 3: Synthesis of Compound 24.

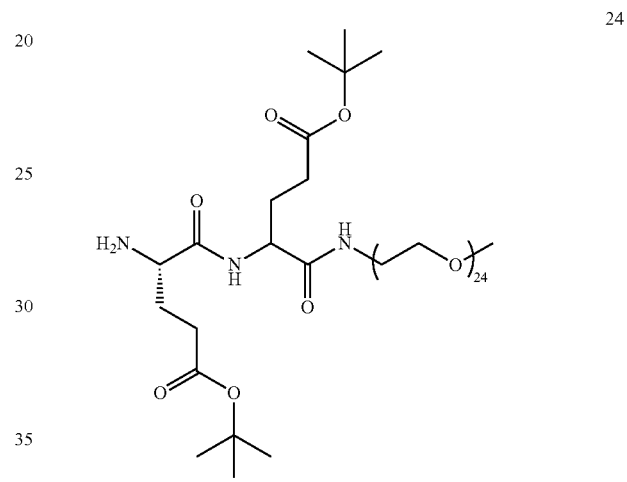

24

To a stirred solution of compound 23 (193 mg) in anhydrous DMF (900 μL) was added piperidine (34 μL) and the reaction mixture was stirred for 1 h at room temperature. The solution was concentrated in vacuo to dryness and the residue triturated with diethyl ether (2×2.5 mL). The product was dried in vacuo to give compound 24 as an off-white solid (166 mg).

Step 4: Synthesis of Compound 25.

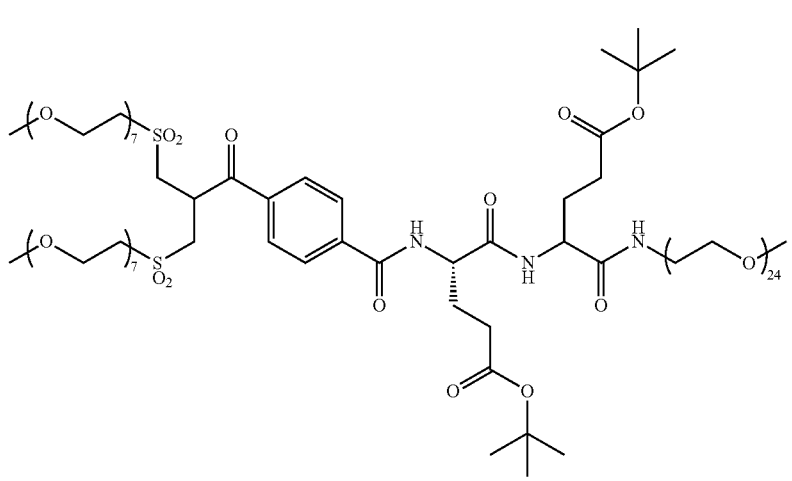

25

Reagent 25 was synthesised in analogous way to reagent 19 of Example 9 from compound 24 and compound 9. Reagent 25 was isolated as a colourless oil. m/z [M+H]$^+$ (2407, 25%), [M+Na]$^+$ (2429, 70%).

Step 5: Synthesis of Reagent 26.

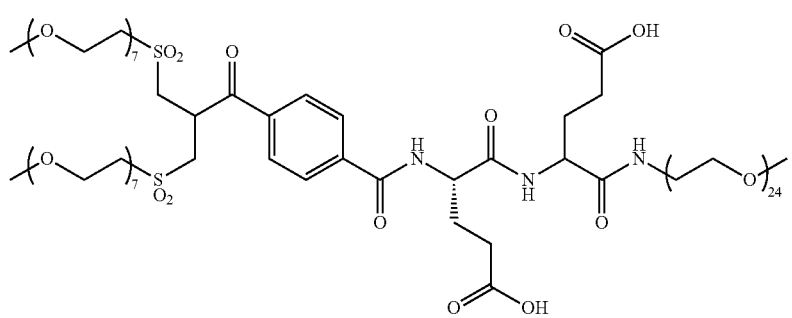

26

Reagent 26 was synthesised in analogous way to reagent 20 of Example 9 from reagent 25.

Reagent 26 was isolated as a colourless oil. m/z [M+H]$^+$ (2294, 20%), [M+Na]$^+$ (2317, 10%).

Step 6: Synthesis of Reagent 21.

To a stirred solution of reagent 26 (28.1 mg), val-cit-PAB-MMAE TFA salt (30.6 mg) and HATU (13.9 mg) in anhydrous DMF (1.5 mL) was added NMM (6.7 µL) and the reaction mixture was stirred at 0° C. for 5 h. The solution was diluted with water (1 mL) and purified by reverse phase C18-column chromatography eluting with buffer A (v/v): water:5% acetonitrile:0.1% TFA and buffer B (v/v): acetonitrile:0.1% TFA (100:0 v/v to 60:40 v/v). The organic solvent was removed in vacuo and the aqueous solvent was removed by lyophilisation to give reagent 21 as a white solid (36.1 mg). m/z [M+2H]$^{2+}$ (2253, 40%), [M+3H]$^{3+}$ (1502, 60%) and [M+4H]$^{4+}$ (1127, 100%).

Example 11: General Protocol for Conjugation of Reagents to Anti-PSMA Antibodies to Produce Antibody Drug Conjugates (ADCs) with DAR 4

A solution of anti-PSMA antibody (e.g. AB-03) at a concentration of 5.2 mg/mL in reaction buffer (20 mM sodium phosphate, 150 mM NaCl, 20 mM EDTA, pH 7.5), was heated to 40° C. for 15 min. TCEP (6 equiv. per mAb) was added to the mAb solution, mixed gently and incubated at 40° C. for 1 h before being allowed to cool to 22° C. Conjugation reagents 1, 2, 5, 7, 12, 13, 14 and 21 were dissolved in MeCN or DMF to give a 1.6 mM stock solution. The reduced mAb solution was diluted to 4.2 mg/mL with reaction buffer. Conjugation reagent (6 equiv. per mAb) was added to the mAb solution, the reaction was mixed gently and incubated at 22° C. for 6 to 22 h. After incubation, the reaction was treated with 50 mM N-acetyl-L-cysteine (20 equiv. over reagent) at 22° C. for 1 h.

Figure 4A:
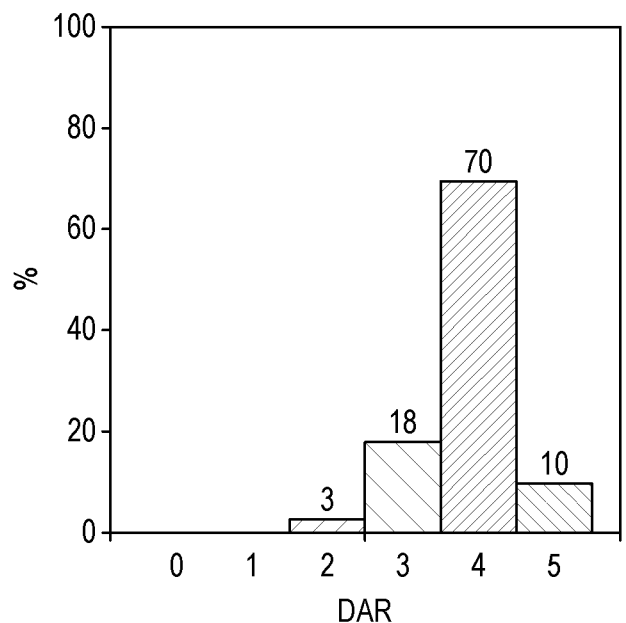
FIG. 4 shows the distribution of drug to antibody ratios (DARs) for an antibody-drug-conjugate prepared using an antibody of the invention.
Figure 4B:
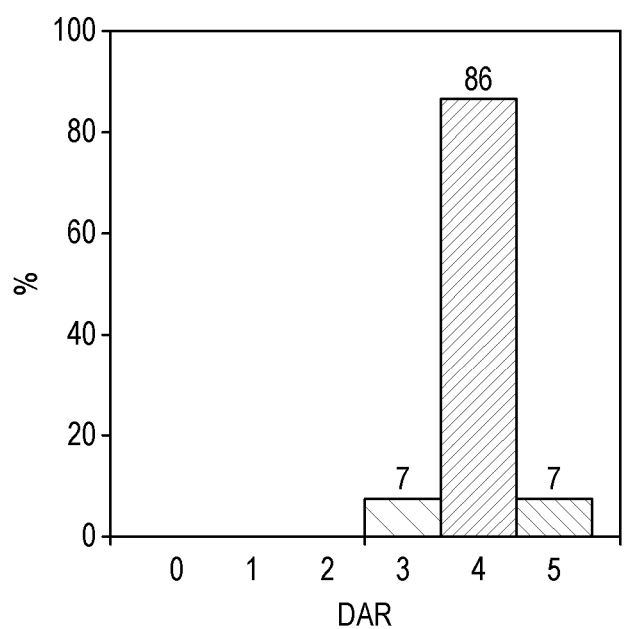

Reaction samples may be analysed by hydrophobic interaction chromatography (HIC) using a TOSOH TSK-gel Butyl-NPR column. The area of each peak obtained for each drug to antibody ratio (DAR) variant separated, (identified by the ratio of the UV absorbance maxima for drug and antibody and order of peak elution), was plotted as a bar chart. The results of conjugations with reagents 1 and 2, giving rise to ADCs 3 and 4, respectively, are shown in FIGS. 4A and 4B respectively. The major product for each reaction was the DAR 4 conjugate.

Reaction mixtures were purified by preparative HIC using ToyoPearl Phenyl 650S resin equilibrated with Buffer A: 50 mM sodium phosphate, 2.0 M NaCl, pH 7.0, and Buffer B: 80% 50 mM sodium phosphate, 20% isopropanol, pH 7.0. An equal volume of 4.0 M NaCl in 50 mM sodium phosphate, pH 7.0, was added to the conjugation mixture which was then injected onto the column and subsequently eluted using a 0-100% Buffer B gradient. Fractions of eluted peaks were collected and analysed by analytical HIC. Fractions containing DAR 4 were combined, buffer exchanged into PBS pH 7.4 and concentrated in VivaSpin 20 (10 kDa MWCO PES membrane) concentrators. The final sample was quantified by Bradford assay before further evaluation. Conjugation reagents 1, 2, 5, 7, 12, 13, 14 and 21 produced ADCs 3, 4, 6, 27, 28, 29, 30 and 31 respectively.

Example 12: Conjugation of Anti-PSMA Antibody with the Maleimide Reagent Mc-Vc-PAB-MMAE to Produce a Conjugate 32 with Average DAR 4

Anti-PSMA antibody AB-03 at a concentration of 5.2 mg/mL in reaction buffer was heated to 40° C. for 15 min. TCEP (2 eq.) was added to the mAb solution, mixed gently and then incubated at 40° C. for 1 h and allowed to cool to 22° C. The maleimide reagent, mc-val-cit-PAB-MMAE (Concortis/Levena Biopharma), was dissolved in MeCN to give a 2.1 mM stock solution. The reduced mAb solution was diluted to 4.2 mg/mL with reaction buffer. mc-val-cit-PAB-MMAE (4 eq. per mAb) was added to the mAb solution, the reaction was mixed gently and incubated at 22° C. for 1 h. The reaction was treated with 50 mM N-acetyl-L-cysteine (20 eq. over reagent) and allowed to proceed at 22° C. for 1 h. The crude conjugation mixture was analysed by hydrophobic interaction chromatography. The crude reaction was diafiltrated (Vivaspin 20, 10 kDa PES membrane) to remove reactants and concentrate the conjugate. The concentrated sample was buffer exchanged into DPBS, pH 7.1-7.5 and then sterile filtered (0.22 m PVDF membranes).

Example 13: Conjugation of Antibodies AB-P1 and AB-P2 with Mc-Vc-PAB-MMAE to Produce Average DAR 4 Conjugates 33 and 34

Conjugation was carried out in an analogous manner to the production of conjugate 32 of Example 12.

Example 14: In Vitro Cell-Killing Analysis of an Anti-PSMA ADC 3, Prepared from Bis-Sulfone-PEG(24u)-Val-Cit-PAB-MMAE Conjugation Reagent 1

Loss of tumour cell viability following treatment with cytotoxic drugs or ADCs in vitro can be measured by growing cell lines in the presence of increasing concentrations of drugs or ADCs and quantifying the loss of proliferation or metabolic activity using CellTiter Glo® Luminescence reagent (Promega Corp. Technical Bulletin TB288; Lewis Phillips G. D, Cancer Res 2008; 68:9280-9290). The protocol describes cell seeding, drug treatment and determination of the cell viability in reference to untreated cells based on ATP synthesis, which is directly related to the number of cells present in the well.

PSMA-positive LNCaP (clone FGC) and C4-2 cells, as well as PSMA-negative PC-3 cells were detached with TrypLE and resuspended in complete medium. Cells were counted using disposable Neubauer counting chambers and cell density adjusted to $10\times10^4$ cells/mL for LNCaP, $2\times10^4$ cells/mL for C4-2 and $1\times10^4$ cells/mL for PC-3 respectively. Cells were seeded (100 μL/well) into either Tissue Culture treated (C4-2) or Poly-D-Lysine coated (LNCaP and PC-3) white, opaque-walled, 96-well plates and incubated for 24 h at 37° C. and 5% $CO_2$. Tumour cell lines LNCaP (CRL-1740) and PC-3 (CRL-1435) were purchased from the American Type Culture Collection (ATCC). LNCaP and C4-2 cells were grown in RPMI-1640 medium containing 2 mM glutamine (Life Technologies®), 10% fetal bovine serum, 100 U/mL Penicillin and 100 μg/mL Streptomycin. PC-3 cells were grown in Ham's F-12K (Life Technologies®), 10% fetal bovine serum, 100 UI/mL Penicillin and 100 μg/mL Streptomycin (Invitrogen). The cells were maintained as described in the product information sheets and following ATCC general recommendations for tissue culture. Cells were cultured according to ATCC recommendations and references quoted therein, for example, Culture of Animal Cells: A Manual of Basic Technique by R. Ian Freshney $3^{rd}$ edition, published by Alan R. Liss, N.Y. 1994, or $5^{th}$ edition published by Wiley-Liss, N.Y. 2005.

The cell viability assay was carried out using the CellTiter Glo® Luminescence reagent, as described by the manufacturer's instructions, (Promega Corp. Technical Bulletin TB288; Lewis Phillips G. D, Cancer Res 2008; 68:9280-9290). Luminescence was recorded using a plate reader (e.g. Molecular Devices Spectramax M3 plate reader), and data subsequently analysed using a four parameter non-linear regression model.

If plotted as a graph, viability was expressed as % of untreated cells and calculated using the following formula:

$$\% \text{ Viability} = 100 \times \frac{Luminescence_{Sample} - Luminescence_{No\ cell\ Control}}{Luminescence_{Untreated} - Luminescence_{No\ cell\ Control}}$$

The % viability (Y-axis) was plotted against the logarithm of drug concentration in nM (X-axis) to extrapolate the $IC_{50}$ values for all conjugates as well as free drugs.

The in vitro activity of ADC 3 was determined by measuring the inhibitory effect on cell growth of the PSMA receptor over-expressing cancer cell line LNCaP. A control DAR 4 non-binding mAb drug conjugate was also included in the study to demonstrate antigen selective cell-killing. The non-binding control was a trastuzumab ADC prepared from conjugation reagent 1 by the method used to prepare 3. Trastuzumab binds the target HER-2, which is not present, or present at very low levels, on LNCap cells. Thus trastuzumab ADC is not specifically targeted at these cells and should only have a non-specific cytotoxic effect.

Serial dilutions of ADC or free drug (MMAE) were made in triplicate by pipetting across a 96 well plate from columns 3-10 with 2-2.5-fold dilutions for MMAE or the MMAE DAR 4 conjugate respectively in cell culture medium as a diluent. The LNCaP cells were treated with free drug or drug-conjugate concentrations shown in table 2. Cells were subsequently incubated with the drug (total volume 200 μL/well), at 37° C. and 5% $CO_2$ for a further 96 h.

TABLE 2

| Cell line | Drug/drug-conjugate | Concentration range |
|---|---|---|
| LNCaP | MMAE | 0.01-20 nM |
| LNCaP | DAR 4 ADC 3 | 0.01-5 nM |

Figure 5:
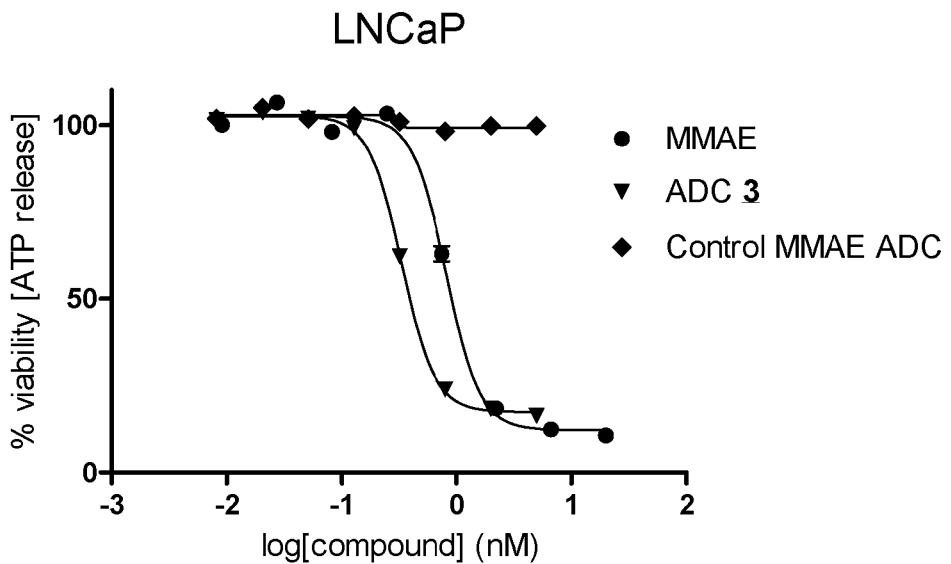
FIG. 5 shows cell viability responses of LNCaP cells when treated with an antibody-drug-conjugate prepared using an antibody of the invention.

The results are shown in FIG. 5 and $IC_{50}$ values are shown in Table 3, illustrating cell viability responses to treatment with either ADC 3 or free drug within LNCaP cells. ADC 3 is active within the PSMA-positive LNCaP cell line, whereas the non-binding trastuzumab control ADC shows little or no cytotoxic effect upon these cells. The trastuzumab ADC data did not allow for the determination of an $IC_{50}$ value.

TABLE 3

| Sample | LNCaP $IC_{50}$ (nM) |
|---|---|
| MMAE | 0.81 |
| ADC 3 | 0.33 |

Example 15: In Vitro Cell-Killing Analysis of an Anti-PSMA ADC 6 Prepared from Bis-Sulfone-PEG(24u)-Val-Ala-PAB-AHX-DM1 Conjugation Reagent 5

The in vitro activity of the DAR 4 ADC 6 was determined as described for ADC 3 in Example 14. Serial dilutions of ADC were made in triplicate by pipetting across a 96 well plate from columns 3-10 with 2.5-3-fold dilutions for ADC 6 or trastuzumab control conjugate, respectively, using cell culture medium as a diluent. As within Example 14, a non-binding control trastuzumab ADC was used to demonstrate antigen selective cell-killing by ADC 6. The non-binding control was prepared from conjugation reagent 5 by the same method used to prepare 6. Trastuzumab binds the target HER-2, which is not present, or present at very low levels, on LNCap cells. Thus, trastuzumab ADC is not specifically targeted at these cells and should only have a non-specific cytotoxic effect.

The PSMA-positive cell line, LNCaP was treated with free drug or conjugate concentrations as shown in table 4.

TABLE 4

| Cell line | ADC | Concentration range |
|---|---|---|
| LNCaP | Trastuzumab Control ADC | 0.005-10 nM |
| LNCaP | ADC 6 | 0.005-10 nM |

Figure 6:
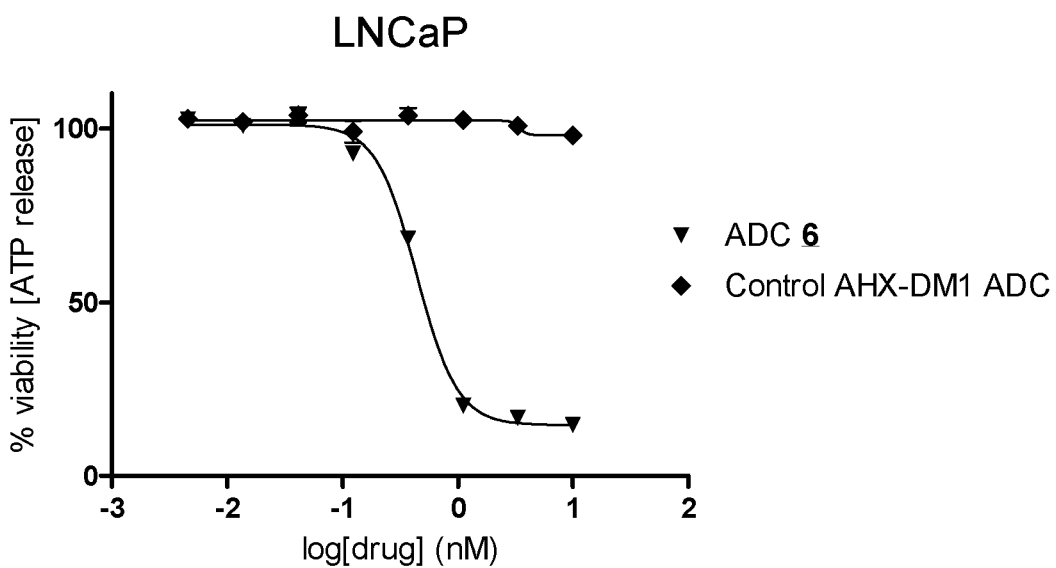
FIG. 6 shows cell viability responses of LNCaP cells when treated with a different antibody-drug-conjugate prepared using an antibody of the invention.
Figure 7:
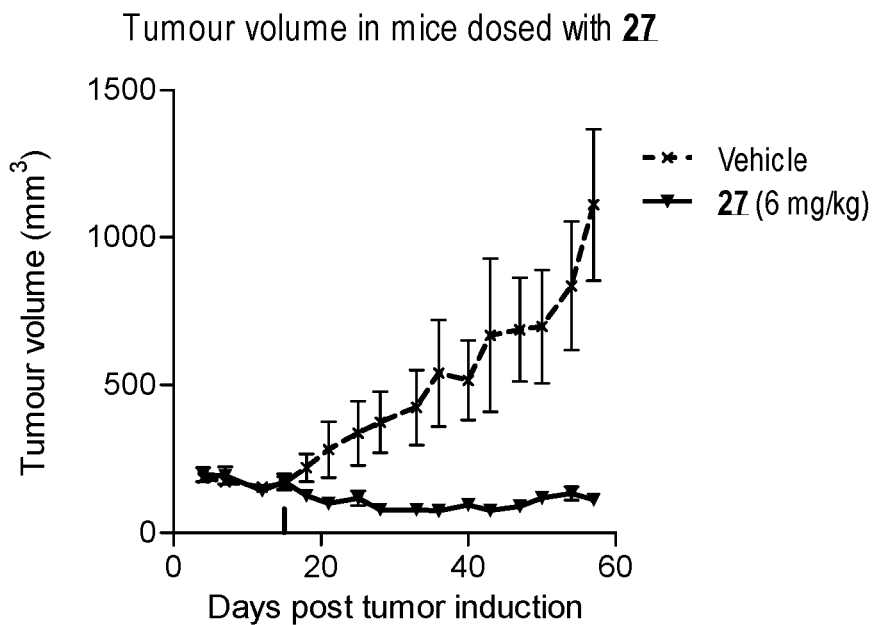
FIGS. 7 to 14 show changes in tumour volume over time in an in vivo xenograft model in response to dosing with antibody-drug conjugates prepared using an antibody of the invention.
Figure 8:
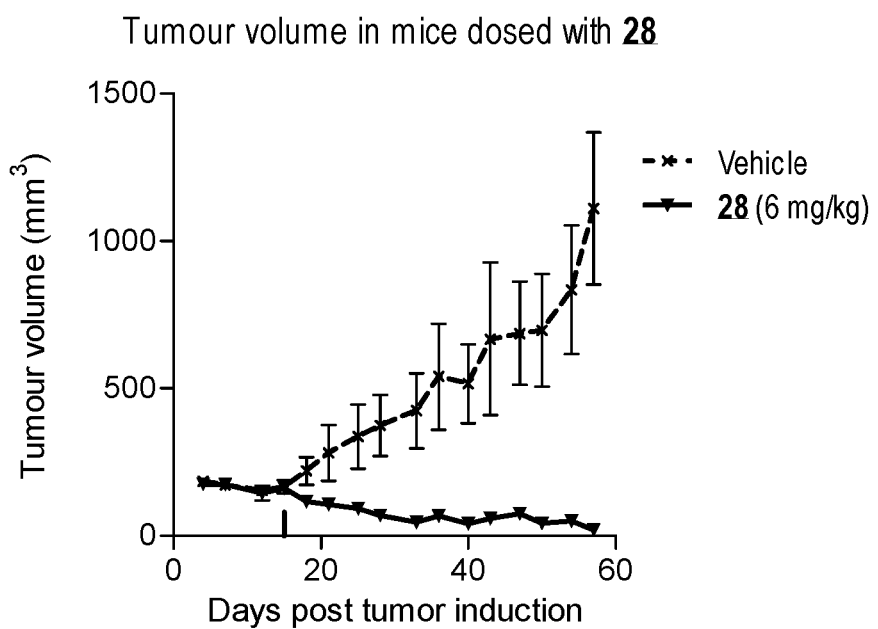
Figure 9:
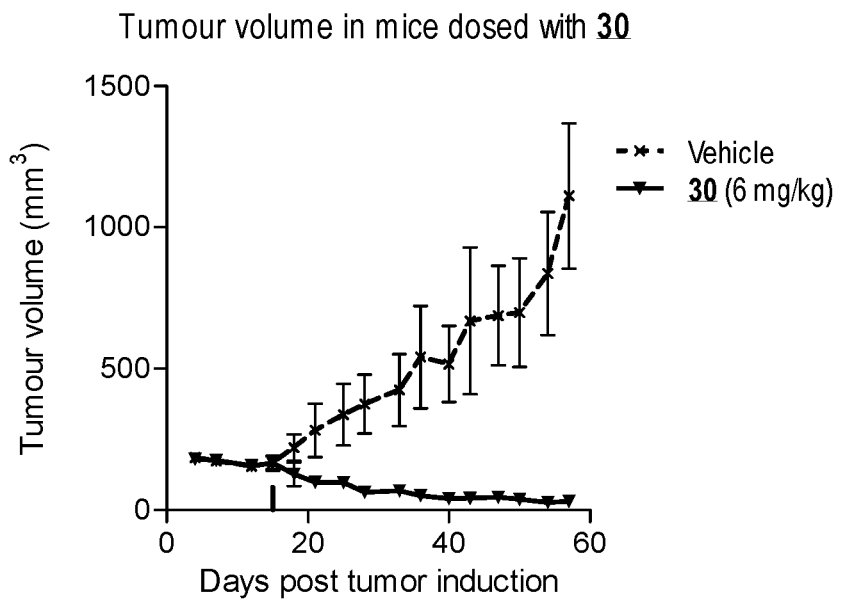
Figure 10:
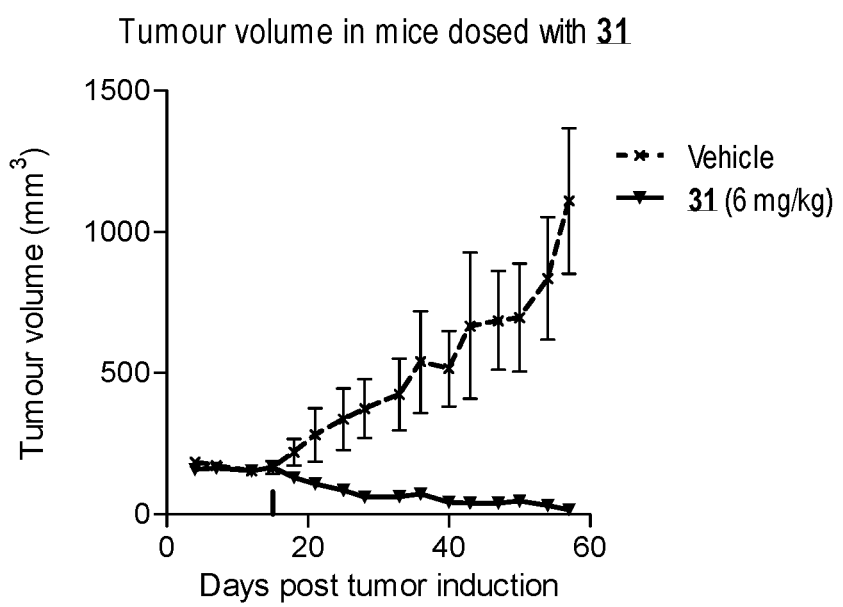
Figure 11:
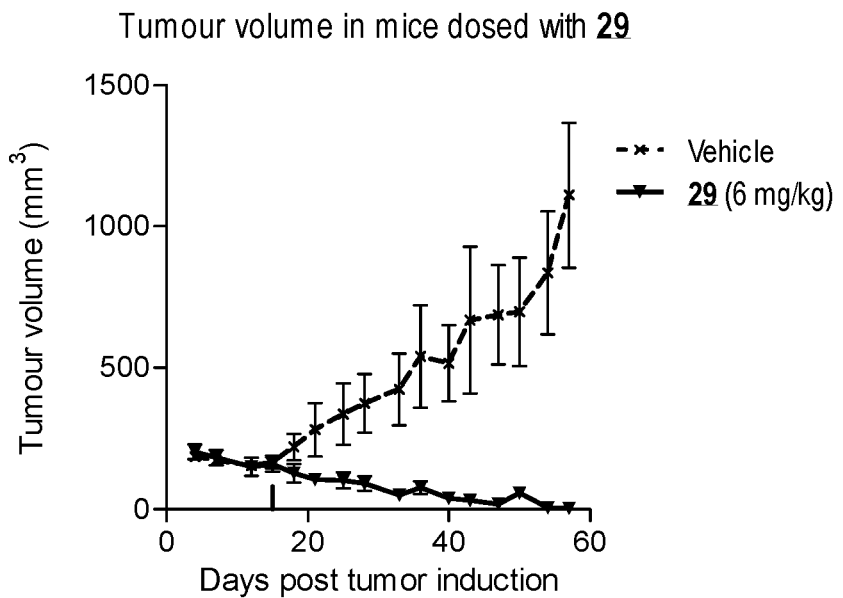
Figure 12:
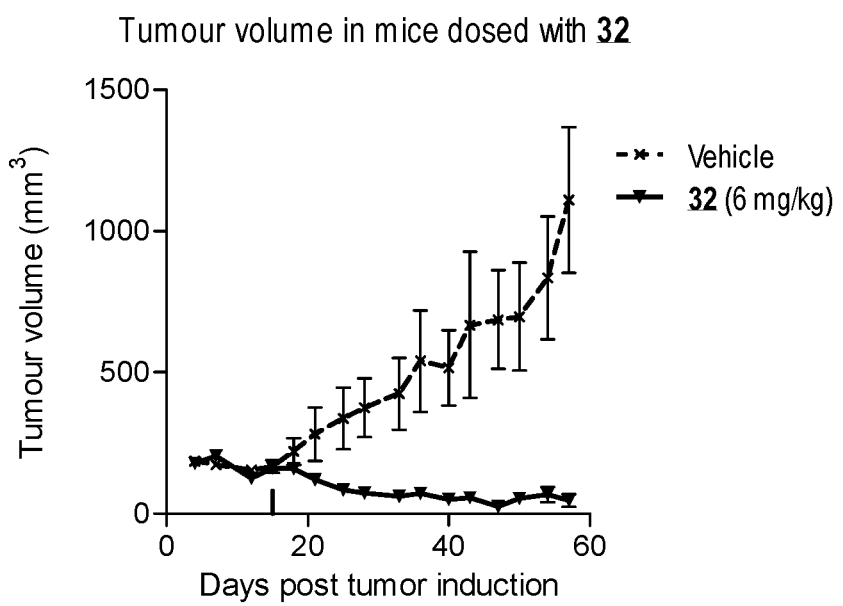
Figure 13:
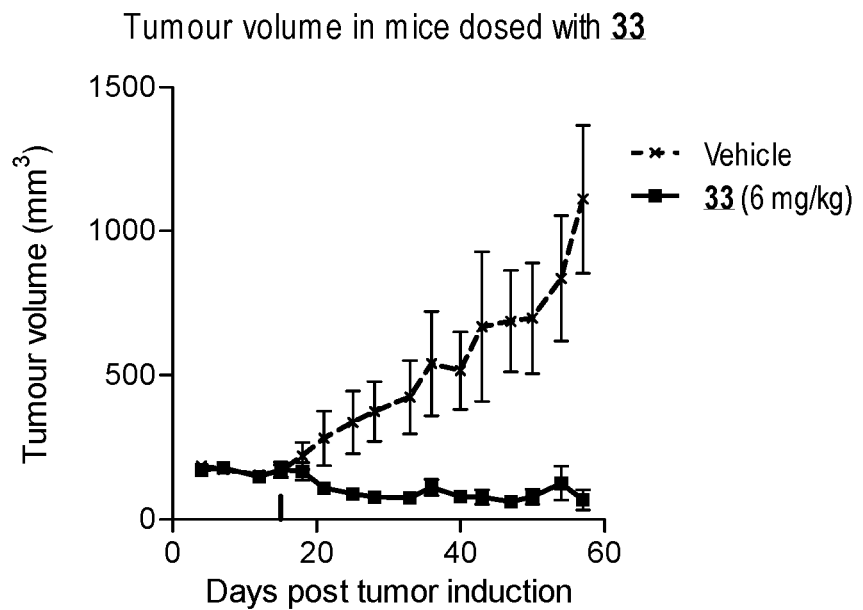
Figure 14:
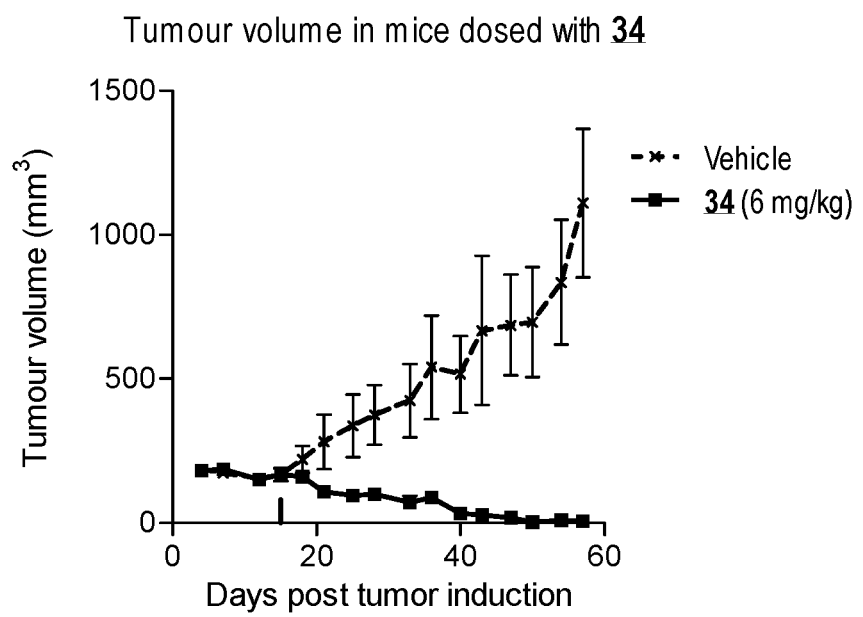

The results are shown in FIG. 6, which illustrates cell viability responses to treatment with ADC 6 or trastuzumab control ADC within LNCaP cells. Viability is expressed as % of untreated cells. The % viability (Y-axis) is plotted against the logarithm of drug concentration in nM (X-axis) to determine the $IC_{50}$ values for both conjugates. The $IC_{50}$ values are shown in Table 5.

TABLE 5

| Sample | LNCaP IC$_{50}$ (nM) |
|---|---|
| Trastuzumab Control ADC | Not determined |
| DAR 4 ADC 6 | 0.44 |

As shown in FIG. 6 and Table 5, ADC 6 is active in the PSMA-positive LNCaP cell line.

Example 16: Analysis of Antibody Drug Conjugates and Free Payloads by In Vitro Cell Viability Assay The in vitro efficacies of ADCs 27, 28, 29, 30 and 31, prepared as described within Example 11, and ADCs 32, 33 and 34, prepared as described within Examples 12 and 13, respectively, were determined by measuring their inhibitory effect upon cell growth of PSMA over-expressing cancer cell lines, as described in Example 14.

Eight point serial dilutions of ADCs or free drugs were prepared in the relevant culture medium. All three cell lines were treated with ADC concentrations of 50-0.00064 nM. MMAE was used at 500-0.0064 nM on C4-2 cells and 10,000-0.128 nM on both LNCaP and PC-3 cells. The medium from the plate containing the adherent cells was removed and replaced by 100 μL/well of the serially diluted compounds. The cells were then incubated at 37° C. and 5% CO$_2$ for a further 96 h.

As shown in Table 6, in the concentration range tested, all ADCs were able to specifically inhibit the proliferation of PSMA expressing LNCaP and C4-2 cells, showing very limited effect on PSMA-negative PC-3 cells.

TABLE 6

IC$_{50}$ values showing the anti-proliferative effect of ADCs and free payloads on LNCaP, C4-2 and PC-3 cells (negative control).

| Sample | LNCaP IC$_{50}$ (nM) | C4-2 IC$_{50}$ (nM) | PC-3 IC$_{50}$ (nM) |
|---|---|---|---|
| 27 | 0.61 | 0.02 | >50 |
| 28 | 0.38 | 0.06 | >50 |
| 30 | 0.47 | 0.11 | >50 |
| 31 | 0.17 | 0.03 | >50 |
| 29 | 0.59 | 0.08 | >50 |
| 32 | 0.84 | 0.11 | >10 |
| 33 | 0.18 | 0.06 | >50 |
| 34 | 0.27 | 0.07 | >50 |
| MMAE |  | 0.28 | 8.2 |
| AHX-DM1 | 341 | 57 | >1000 |

Example 17: Evaluation of Antibody Drug Conjugates (ADCs) and Free Payloads in an In Vivo Efficacy Study Healthy female severe combined immunodeficient (SCID) mice (C.B-17/Icr-Prkdcscid, Charles River Laboratories) were used. The animals were maintained in SPF health status according to the FELASA guidelines in housing rooms under controlled environmental conditions. Animal enclosures were designed to provide sterile and adequate space with bedding material, food and water, environmental and social enrichment.

Xenografts were initiated with C4-2 human prostate carcinoma cells by subcutaneous injection in SCID mice. On the day of tumour induction, each test mouse received 10$^7$ C4-2 cells in 200 μL of RPMI 1640 into the right flank. Tumours were measured in two dimensions using calipers, and volume was calculated using the formula:

$$\text{Tumor Volume (mm}^2\text{)} = \frac{w^2 \times l}{2}$$

where w=width and l=length, in mm, of the tumour.

Eighteen days after tumour implantation, designated as Day 1 of the study, the animals were sorted into groups each consisting of five mice with group mean tumour volumes of 100 to 200 mm$^3$. Treatment began on Day 1 in all groups. Treatment groups were given intravenous injection (i.v.) on Day 1 at 6 mg/kg with antibody-drug conjugates 27, 28, 30, 31, 29, 32 and also the Antibody-drug conjugates 33 and 34. PBS was given to mice in the vehicle-treated control group.

Mice were monitored individually, and each animal was euthanized when its tumour reached the endpoint volume of 2000 mm$^3$. Treatment tolerability was assessed by body weight measurements and frequent observation for clinical signs of treatment-related side effects.

Percentage change in tumour volume was calculated for each mouse at day 57 and expressed as % mean±standard error. All regimens were well tolerated and could be evaluated for efficacy. The results are shown in FIGS. 7 to 14, which show the percentage change in tumour volume for antibody-drug conjugates 27, 28, 30, 31, 29, 32 and also antibody-drug conjugates 33 and ADC 34. In each case, the Figures show the changes in tumour volume over time in response to dosing with antibody-drug conjugate. Values are expressed as % mean±standard error.

Example 18: Comparison of the Stability of Anti-PSMA Antibodies by Heat Stress Test Antibody samples (0.5 mg/mL in PBS) were incubated at 75° C. for 30 min followed by incubation in an ice-bath for 5 min prior to being analysed for their extent of aggregation. Analysis of antibody solutions was carried out by Size Exclusion Chromatography (SEC) and by turbidity measurements.

SEC:

SEC was performed using a TOSOH Bioscience TSK gel Super SW 3000 column. UV absorbance at 280 nm was monitored during an isocratic elution with a 0.2 M Potassium phosphate buffer, pH 6.8 (0.2 M potassium chloride and 15% isopropanol). The elution times and number of peaks indicate whether the sample contains aggregated, degraded or native antibody. The % area under the curve (Abs280) was used to determine the quantity of each species present in the SEC analysis.

Results:

The results of the SEC measurements are shown in Table 7.

TABLE 7

| Antibody analysis- post stress test. | Ab in native conformation (%) | Ab in aggregated form (%) |
|---|---|---|
| AB-03 | 75 | 25 |
| AB-P1 | 0 | 100 |
| AB-P2 | 0 | 100 |
| AB-22 | 0 | 100 |

From this SEC analysis, it can be seen that antibodies AB-22, AB-P1 and AB-P2 are less stable than AB-03, displaying a much greater propensity to aggregate upon heating and cooling.

Example 19: Comparison of the Stability of Anti-PSMA Antibodies by Thermal Shift Assay Antibody was diluted to 1.5 mg/mL with DPBS, pH 7.1-7.5, and the concentration determined by measuring OD at 280 nm using a Nanodrop instrument. SEC analysis was carried out prior to thermal-shift analysis to confirm that over 99% of each antibody was present in their native form.

An RT-PCR instrument (StepOnePlus, Applied Biosystems) was set-up for a fluorescence-based thermal-shift assay using Sypro Orange dye as a fluorescent reporter. The assay was set-up in a PCR 96 well plate with five replicates per antibody sample and a final reaction volume of 20 µL per well. 13.5 µL of DPBS was pipetted in each well followed by the addition of 4 µL of antibody. Finally, the Sypro Orange reagent was diluted in DPBS from 5000× (stock solution) to 40× and 2.5 µL of the 40× solution was added to each well. Five replicates of a blank were also included in the plate, replacing the 4 µL of antibody sample with 4 µL of DPBS. The assay mixtures were mixed using a multi-channel pipette. The plate was sealed with an optical clear film, centrifuged for 1 min at 1000 rpm and placed into the RT-PCR instrument. Samples were heated using a continuous ramp mode at 1% ramp rate from 25° C. through 99° C. Fluorescence data was collected throughout the temperature ramp, using an excitation filter at 470 nm and emission filter at 610 nm. The total assay time was approximately 45 min. The melting curves generated by the instrument software during the thermal unfolding of the antibodies result from the plotting of fluorescence vs. temperature. The melting temperature (Tm), is the temperature at which half of the antibody molecules are unfolded, (indicated by a 50% increase in fluorescence), and can be determined from the inflection point of the melting curve. The Tms are conventionally calculated by plotting a derivative plot. This is the change in fluorescence divided by the change in time (the change rate) plotted on the Y-axis versus temperature on the X-axis. Tm values for each antibody were determined from the maximum value of the peaks obtained from this plot. Analysis of the melting curves obtained was carried out using GraphPad Prism software (v.5.04).

Figure 23A:
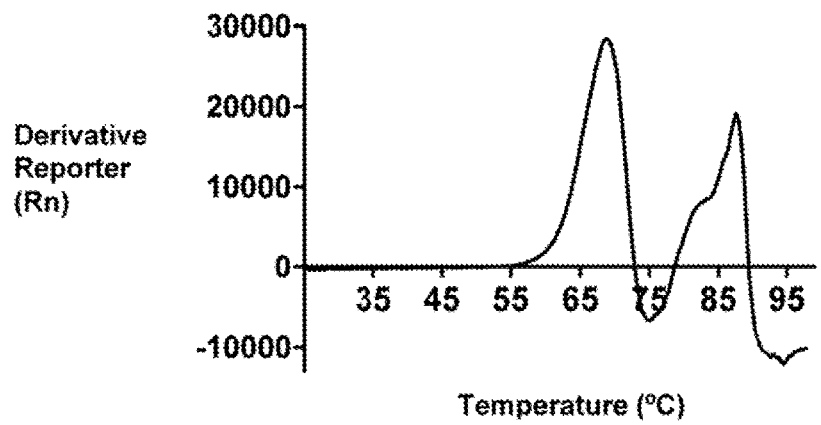
FIG. 23 shows first derivative plots from raw melting point data obtained for (A) AB-03, (B) AB-P1 and (C) AB-P2 antibodies.
Figure 23B:
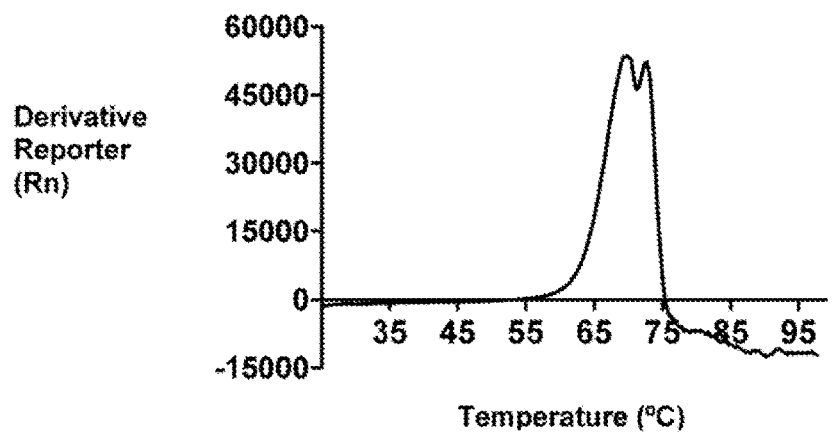
Figure 23C:
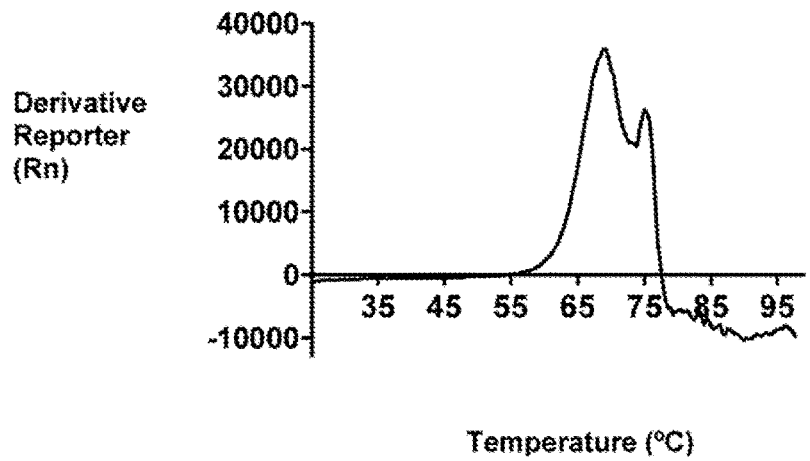

It was determined that the requirement for correction for background fluorescence, (caused by buffer components and free dye), was very low and raw data were used directly for plotting the derivative as it was determined that the fluorescent background correction had little effect on the fitted values of $T_m$. As shown in FIG. 23, two peaks were observed for each of the three antibodies assayed as a result of their multiple domain structure. The first transition peak (Tm1) represents the unfolding of the CH2 and Fab domains, and the second transition peak (Tm2) represents the unfolding of the CH3 domain. Values for $T_m1$ and $T_m2$ of antibodies AB-03, AB-P1 and AB-P2 are given in Table 8. These Tm data show that while the Fab and CH2 domains of the three antibodies show a similar level of stability, the CH3 domain of AB-03 is much more stable than AB-P1 and AB-P2, as the melting temperature is approximately 12-15° C. higher.

TABLE 8

|  | AB-03 | AB-P1 | AB-P2 |
| --- | --- | --- | --- |
| $T_{m1}$ (° C.) | 68.9 ± 0.1 | 69.8 ± 0.1 | 68.9 ± 0.1 |
| $T_{m2}$ (° C.) | 87.5 ± 0.1 | 72.6 ± 0.1 | 75.2 ± 0.1 |

Example 20: Synthesis of Conjugation Reagent 35 Comprising Amido-6'-β3-Cyclodextrin and a Maytansinoid Cytotoxic Payload

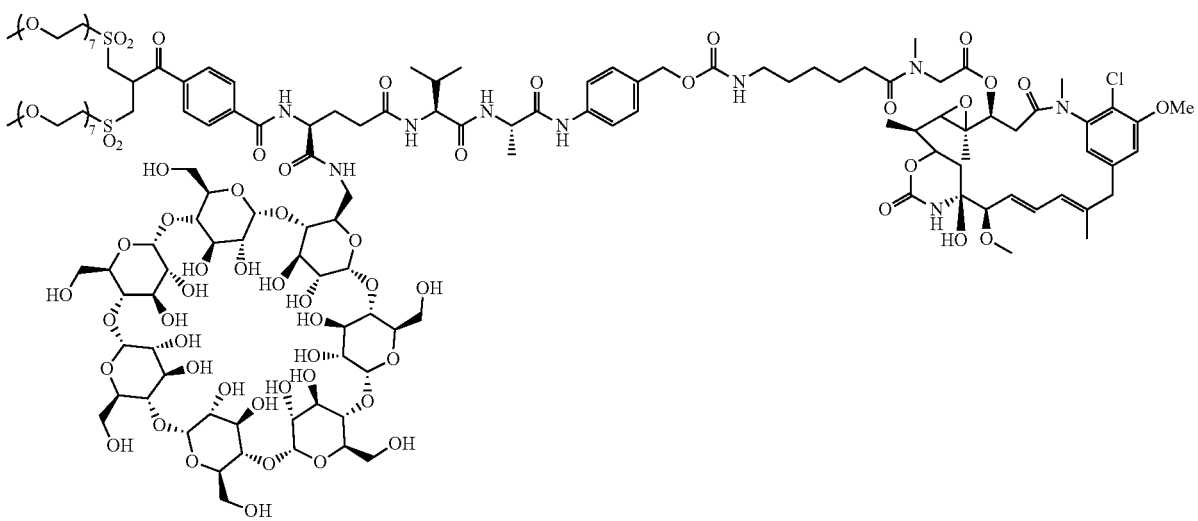

35

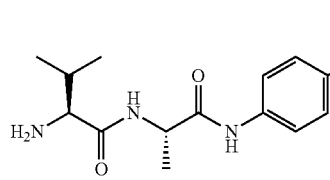
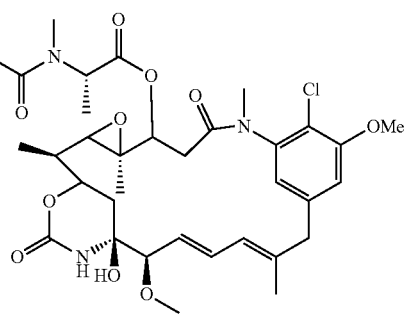

Val-Ala-PAB-AHX-DM1

Step 1: Synthesis of Compound 36.

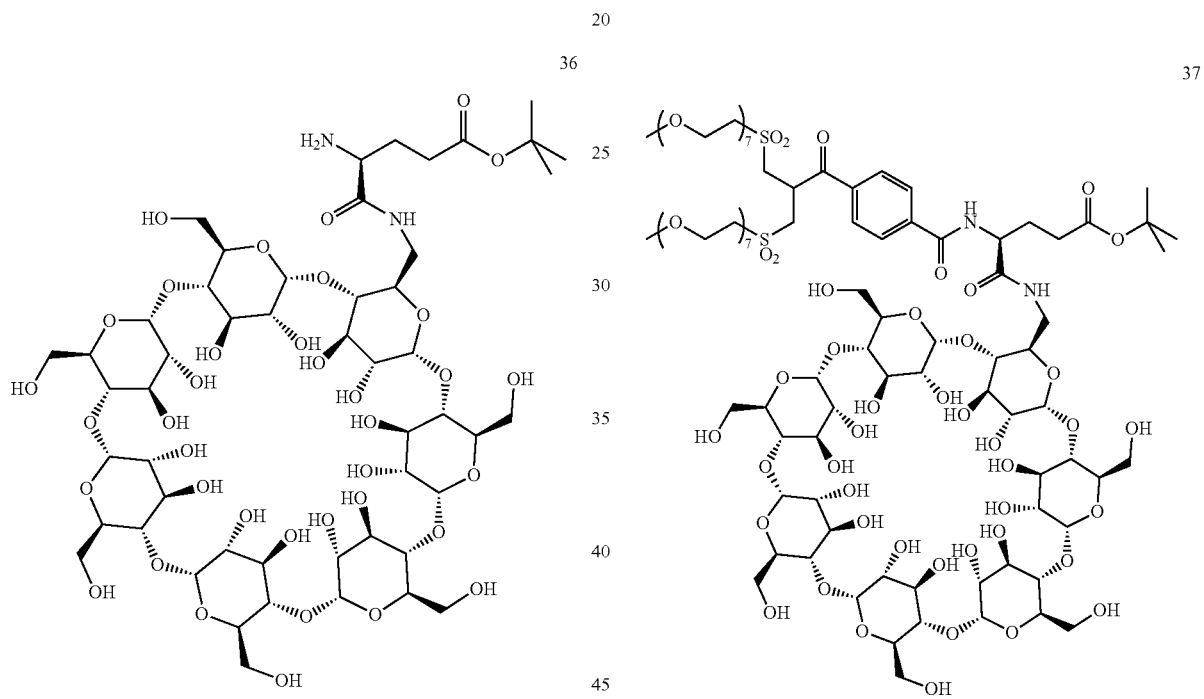

To a solution of Fmoc-Glu-(OtBu)-OH (55 mg) in DMF (1 mL) was added a solution of HATU (116 mg) in DMF (1 mL), NMM (34 μl) and a solution of 6-monodeoxy-6-monoamino-3-cyclodextrin hydrochloride (150 mg) in DMF (2 mL). After stirring the reaction mixture for 16 h at room temperature, NMM (13 μl) was added followed after a further 1 h by additional 6-monodeoxy-6-monoamino-β-cyclodextrin hydrochloride (8 mg) in DMF (200 μL). After 3 h, the volatiles were removed in vacuo. The residue was dissolved in DMF (5 mL) and piperidine (151 μL) was added to the solution which was stirred for 1 h at room temperature. The reaction solution was then concentrated in vacuo and the resultant oil precipitated into diethyl ethyl (4×200 mL) at room temperature and filtered to give compound 36 as a white solid. m/z [M+H]$^+$ (1320, 50%).

Step 2: Synthesis of Compound 37.

To a solution of reagent 9 (156 mg) in DMF (2 mL) was added a solution of HATU (141 mg) in DMF (1 mL), NMM (41 μl) and a solution of compound 36 (196 mg) in DMF (2.5 mL). After stirring for 2.5 h at 0° C., additional reagent 9 (19 mg) in DMF (500 μl) was added. After 20 min, the solution was concentrated in vacuo and the residue purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent removed by lyophilisation to give compound 37 as a colourless oil (76 mg). m/z [M+H]$^+$ (2267, 20%), [M+2H]$^{2+}$ (1134, 100%).

Step 3: Synthesis of Compound 38.

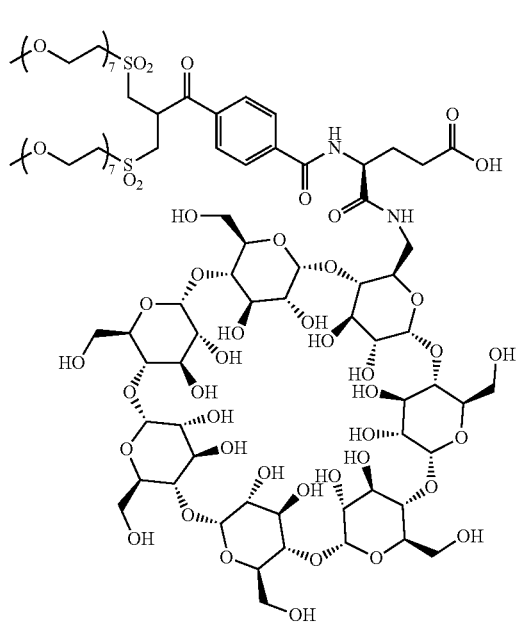

To a solution of compound 37 (33 mg) in THF:chloroform (5 mL, 1:4 v/v) was added p-toluenesulfonic acid (14 mg) and the resulting suspension was stirred at room temperature. After 3.5 hours, the volatiles were removed in vacuo and the resulting residue was purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent removed by lyophilisation to give compound 38 as a colourless oil (26 mg). m/z $[M+H]^+$ (2212, 25%), $[M+2H]^{2+}$ (1106, 100%).

Step 4: Synthesis of Reagent 35.

To a stirred solution of compound 38 (18 mg) in DMF (250 µL) under an inert argon atmosphere at room temperature was added HATU (6 mg). After 1 h, additional HATU (6 mg) and NMM (1.1 µL) was added and the solution left to stir for a further 0.5 h. A separate solution of Val-Ala-PAB-AHX-DM1.TFA salt (Concortis/Levena Biopharma, 7.5 mg) and NMM (1.7 µL) in DMF (100 µL) was prepared and stirred for 20 min at room temperature before the two solutions were combined. Additional HATU (6 mg) and NMM (1.7 µL) were added and the solution was stirred at room temperature. After 2 h, additional HATU (6 mg) was added and the solution was left to stir for a further 4 h at room temperature before additional NMM (1.7 µL) was added. After 3.5 h, the volatiles were removed in vacuo and the resulting residue purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give reagent 35 (2.7 mg). m/z $[M+Na+2H]^{3+}$ (1100, 65%). $[M+3H]^{3+}$ (1094, 100%).

It will be understood that similar compounds can be made using alternative cyclodextrin rings, for example 3α-cyclodextrin.

Example 21: Conjugation of Anti-PSMA Antibody with Reagent 35 to Produce Antibody Drug Conjugate 39 with Average DAR 4

Conjugation reagent 35 was conjugated to anti-PSMA antibody, giving rise to ADC 39. Anti-PSMA antibody AB-03, at a concentration of 5.2 mg/mL in 20 mM sodium phosphate, pH 7.5 (containing 150 mM NaCl and 20 mM EDTA) was heated to 40° C. in a heating block for 15 min. TCEP (6 eq. per mAb) was added to the mAb solution, mixed gently and incubated at 40° C. for 1 h before being allowed to cool to 22° C. Conjugation reagent 35, was dissolved in DMF to give a 1.5 mM solutions. The reduced mAb solution was diluted to 4.4 mg/mL with 20 mM sodium phosphate, pH 7.5 (containing 150 mM NaCl and 20 mM EDTA). Conjugation reagent (5.6 eq. per mAb) was added to the mAb solution, the reaction was mixed gently and incubated at 22° C. for 6 to 22 h. After this the reaction was treated with 50 mM N-acetyl-L-cysteine (20 eq. over reagent) at 22° C. for 1 h. The crude conjugation mixture was analysed by hydrophobic interaction chromatography. The crude reaction was mixed with an equal volume of 50 mM sodium phosphate, pH 7 (4 M NaCl) and the resulting solution was loaded onto a ToyoPearl Phenyl-650S HIC column equilibrated with 50 mM sodium phosphate, pH 7 (2 M NaCl). The ADC was eluted from the column with a gradient of 50 mM sodium phosphate, pH 7 (20% isopropanol). Fractions containing DAR 4 ADC were pooled and concentrated (Vivaspin 20, 10 kDa PES membrane). The concentrated sample was buffer exchanged into PBS, pH 7.1-7.5 and sterile filtered (0.22 m PVDF membranes). DAR assignments were based on A248/A280 absorption ratios. The average DAR of conjugates was calculated from the relative peak areas of individual DAR species following HIC analysis at 280 nm.

Example 22: Analysis of Antibody Drug Conjugate 39 by In Vitro Cell Viability Assay The in vitro efficacy of the antibody drug conjugate 39, prepared in Example 21 was determined by measuring the inhibitory effect of the conjugate upon cell growth of a target over-expressing cancer cell line.

Loss of tumour cell viability following treatment with ADCs or free payloads in vitro can be measured by growing cell lines in the presence of increasing concentrations of compounds and quantifying the loss of proliferation or metabolic activity using Cell-Titer Glo® Luminescent reagent (Promega). The protocol describes cell seeding, drug treatment and determination of the cell viability in reference to untreated cells based on ATP synthesis, which is directly correlated to the number of cells present in the well.

The characteristics of the cell line as well as the seeding densities for the assays are described in the table below.

Cells were counted using disposable Neubauer counting chambers and cell density adjusted as detailed in the table below. LNCaP cells were seeded at 50 µL/well into Tissue Culture treated opaque-walled 96-well white plates and incubated for 24 h at 37° C. and 5% $CO_2$.

| Cell line | Target | Growth Medium | Seeding density |
|---|---|---|---|
| LNCaP clone FGC | PSMA | RPMI-1640 medium (Life Technologies ®), 10% fetal bovine serum, 100 U/mL Penicillin and 100 µg/mL Streptomycin | $1 \times 10^4$ cells per well |

Eight point serial dilutions of compounds were prepared in the relevant culture medium. The titration range was adjusted for each compound/cell line combination. For LNCaP cells, growth medium was removed and replaced by 100 μL/well of 1×ADC dilutions. The cells were then incubated at 37° C. and 5% $CO_2$ for a further 96 h.

The cell viability assay was carried out using the Cell-Titer Glo® Luminescent reagent (Promega), as described by the manufacturer.

Luminescence was recorded using a Molecular Devices SpectramaxM3 plate reader and data subsequently analysed using GraphPad Prism four parameter non-linear regression model. Viability was expressed as % of untreated cells and calculated using the following formula:

$$\% \text{ Viability} = 100 \times \frac{Luminescence_{Sample} - Luminescence_{No\ cell\ Control}}{Luminescence_{Untreated} - Luminescence_{No\ cell\ Control}}$$

The % viability was plotted against the logarithm of drug concentration in nM to extrapolate the $IC_{50}$ value for the conjugate. The concentration range used for the conjugate was 50 nM-3.1 pM and the $IC_{50}$ value obtained was 1.3 nM The $IC_{50}$ value obtained for conjugate 39 shows that the ADC of the invention has potent cell killing properties in vitro.

---

The invention claimed is:

1. An antibody or antigen-binding portion thereof which binds to PSMA and comprises:
   a heavy chain variable domain comprising the sequence given in SEQ ID NO:33, wherein SEQ ID NO: 33 is:
   EVQLVQSGX$^9$E X$^{11}$KKPGASVKV SCKX$^{24}$SGYTFT EYTIHWVX$^{38}$QA

X$^{41}$GKGLEWIGN INPNX$^{55}$GGTTY NQKFEDRX$^{68}$TX$^{70}$

TVDKSTSTAY MELSSLRSED TAVYYCAAGW NFDYWGQGTT

VTVSS wherein:
   X$^9$ is A or P
   X$^{11}$ is V or L
   X$^{24}$ is A or T
   X$^{38}$ is R or K
   X$^{41}$ is P or H
   X$^{55}$ is N or Q
   X$^{68}$ is V or A; and
   X$^{70}$ is I or L;
   and
   a light chain variable domain comprising the sequence given in SEQ ID NO:34, wherein SEQ ID NO: 34 is:
   DIX$^3$MTQSPSX$^{10}$ LSASVGDRVT ITCKASQDVG TAVDWYQQKP

GQAPKLLIYW ASTRHTGVPD RFX$^{63}$GSGSGTD FTLTISRLQX$^{80}$

EDFAX$^{85}$YX$^{87}$CQQ YNSYPLTFGQ GTX$^{103}$VDIK wherein
   X$^3$ is Q or V
   X$^{10}$ is T or F
   X$^{63}$ is S or T
   X$^{80}$ is P or S
   X$^{85}$ is V or D
   X$^{87}$ is Y or F; and
   X$^{103}$ is K or M.

2. An antibody or antigen-binding portion thereof as claimed in claim 1, wherein in SEQ ID NO:33 X$^9$ is A, X$^{11}$ is V, X$^{24}$ is A or T, X$^{38}$ is R or K, X$^{41}$ is P, X$^{55}$ is N or Q, X$^{68}$ is V or A and X$^{70}$ is I.

3. An antibody or antigen-binding portion thereof as claimed in claim 1, wherein in SEQ ID NO:33 X$^9$ is A, X$^{11}$ is V, X$^{24}$ is A, X$^{38}$ is R, or K, X$^{41}$ is P, X$^{55}$ is N, X$^{68}$ is V and X$^{70}$ is I.

4. An antibody or antigen-binding portion thereof as claimed in claim 1, wherein in SEQ ID NO:34 X$^3$ is Q or V, X$^{10}$ is T, X$^{63}$ is S or T, X$^{80}$ is P or S, X$^{85}$ is V or D, X$^{87}$ is Y or F and X$^{103}$ is K.

5. An antibody or antigen-binding portion thereof as claimed in claim 1, wherein in SEQ ID NO:34 X$^3$ is Q, X$^{10}$ is T, X$^{63}$ is S, X$^{80}$ is P, X$^{85}$ is V, X$^{87}$ is Y and X$^{103}$ is K.

6. A polynucleotide encoding an antibody or antigen-binding portion thereof as claimed in claim 1.

7. A vector comprising the polynucleotide as claimed in claim 6.

8. A host cell comprising a vector as claimed in claim 7.

9. An antibody conjugate comprising an antibody or antigen-binding portion thereof as claimed in claim 1 and a payload.

10. An antibody conjugate as claimed in claim 9, in which the payload is bonded to the antibody or antigen-binding portion thereof via a bonding portion which has the general formula:

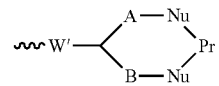

(I)

in which Pr represents said antibody or antigen-binding portion thereof, each Nu represents a nucleophile present in or attached to the antibody or antigen-binding portion thereof, each of A and B independently represents a $C_{1-4}$ alkylene or alkenylene chain, and W' represents an electron withdrawing group or a group obtained by reduction of an electron withdrawing group.

11. A conjugate as claimed in claim 10, in which W' is a keto group —CO—.

12. A conjugate as claimed in claim 10, in which the bonding portion has the formula:

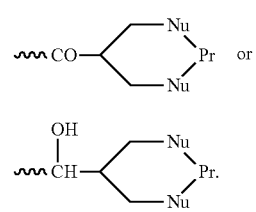

13. A conjugate as claimed in claim 9, which has the general formula:
    $(((D_q\text{-}Lk^1)_r\text{-}P^1)_p\text{-}Lk^2\text{-}Lk^3)_e\text{-}Ab$ (III)
in which D represents the payload;
q represents an integer from 1 to 10;
$Lk^1$ represents a linker;
r represents an integer from 1 to 10;
$P^1$ represents a bond or a c-valent group —$P^2$—NH— where c is from 2 to 11 and $P^2$ is a group containing at least one ethylene unit —$CH_2$—$CH_2$— or ethylene glycol unit —O—$CH_2$—$CH_2$—;
p represents an integer from 1 to 10;
$Lk^2$ represents a bond or a d-valent linker where d is from 2 to 11 and which consists of from 1 to 9 aspartate and/or glutamate residues;
$Lk^3$ represents a linker of the general formula:
—CO-Ph—Y—Z— (AII) in which Ph is an optionally substituted phenyl group; Y represents a CO group or a CH,OH group; and Z represents a group of formula:

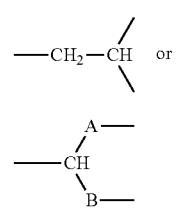

in which each of A and B represents a $C_{1-4}$ alkylene or alkenylene group;
Ab represents an antibody or antigen-binding portion thereof as claimed in claim 1, being bonded to $Lk^3$ via two sulfur atoms derived from a disulfide bond in the antibody or antigen-binding portion thereof; and e represents an integer from 1 to s where s is the number of disulfide bonds present in the antibody or antigen-binding portion thereof prior to conjugating to $Lk^3$.

14. A conjugate as claimed in claim 9, in which the payload is or includes an auristatin or a maytansinoid.

15. A conjugate as claimed in claim 9, which includes from 1 to 20 molecules of a therapeutic agent.

16. A conjugate as claimed in claim 9, which includes a radioisotope.

17. A conjugate as claimed in claim 9, in which the payload is or includes a detectable marker selected from the group consisting of at least one of a radioactive substance, a dye, a contrast agent, a fluorescent compound, a bioluminescent compound, an enzyme, an enhancing agent, or a nanoparticle.

18. A method of diagnosing or treating a cancer mediated by PSMA or characterised by increased expression of PSMA comprising administering an antibody or antigen-binding portion thereof as claimed in claim 1 to a subject in need thereof in an amount effective to treat or prevent the disease or condition.

19. A method using an antibody or an antigen-binding portion thereof as claimed in claim 1 said method comprising:
    (a) contacting a test sample with the antibody or the antigen-binding portion thereof, or the antibody conjugate under conditions that allow for formation of a complex between a PSMA antigen and the antibody or the antigen-binding portion thereof, or the antibody conjugate;
    (b) detecting the presence of the complex.

20. A method of diagnosing or treating a cancer mediated by PSMA or characterised by increased expression of PSMA comprising administering an antibody conjugate as claimed in claim 13 to a subject in need thereof in an amount effective to treat or prevent the disease or condition.

21. A method using an antibody conjugate as claimed in claim 9, said method comprising:
    (a) contacting a test sample with the antibody conjugate under conditions that allow for formation of a complex between a PSMA antigen and the antibody or the antigen-binding portion thereof, or the antibody conjugate;
    (b) detecting the presence of the complex.

22. The method of claim 18, wherein the cancer is prostate cancer.

23. The method of claim 18, wherein the cancer is bladder cancer, pancreatic, lung cancer kidney cancer, sarcoma, liver cancer, breast cancer, brain cancer, colon cancer, testicular cancer, or melanoma.

24. The method of claim 18, wherein the cancer is transitional cell carcinoma of the bladder, pancreatic duct carcinoma, non-small cell lung carcinoma, conventional renal cell carcinoma, soft tissue sarcoma, metastatic adenocarcinoma of the liver, breast carcinoma, glioblastoma multiforme, neuroendocrine carcinoma, colonic carcinoma, testicular embryonal carcinoma, or malignant melanoma.

25. A polynucleotide encoding an antibody or antigen-binding portion thereof as claimed in claim 5.

26. An antibody conjugate comprising an antibody or antigen-binding portion thereof as claimed in claim 5 and a payload.

27. The conjugate as claimed in claim 16, wherein the radioisotope is selected from the group consisting of Iodine-131, Yttrium-90, Lutetium-177, Copper-67, Astatine-211, Lead-212/Bismuth-212, Actinium- 225/Bismuth-213, and Thorium.

28. An antibody or antigen-binding portion thereof as claimed in claim 1, wherein the heavy chain variable domain comprises the sequence

```
                                        (SEQ ID NO: 13)
EVQLVQSGAE VKKPGASVKV SCKASGYTFT EYTIHWVRQA

PGKGLEWIGN INPNNGGTTY NQKFEDRVTI TVDKSTSTAY

MELSSLRSED TAVYYCAAGW NFDYWGQGTT VTVSS;
``` and
the light chain variable domain comprises the sequence

```
                                        (SEQ ID NO: 18)
DIQMTQSPST LSASVGDRVT ITCKASQDVG TAVDWYQQKP

GQAPKLLIYW ASTRHTGVPD RFSGSGSGTD FTLTISRLQP

EDFAVYYCQQ YNSYPLTFGQ GTKVDIK.
```

29. An antibody conjugate comprising the antibody or antigen-binding portion thereof as claimed in claim 28, in which the payload is bonded to the antibody or antigen-binding portion thereof via a bonding portion which has the general formula:

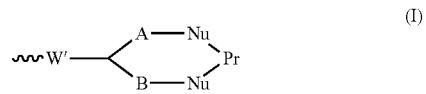

(I)

in which Pr represents said antibody or antigen-binding portion thereof, each Nu represents a nucleophile present in or attached to the antibody or antigen-binding portion thereof, each of A and B independently represents a $C_{1-4}$ alkylene or alkenylene chain, and W' represents an electron withdrawing group or a group obtained by reduction of an electron withdrawing group.

30. A polynucleotide encoding an antibody or antigen-binding portion thereof as claimed in claim 3.

31. An antibody conjugate comprising an antibody or antigen-binding portion thereof as claimed in claim 3 and a payload.

* * * * *

UNITED STATES PATENT AND TRADEMARK OFFICE
CERTIFICATE OF CORRECTION

PATENT NO. : 11,485,792 B2
APPLICATION NO. : 16/303596
DATED : November 1, 2022
INVENTOR(S) : Timothy D. Jones et al.

It is certified that error appears in the above-identified patent and that said Letters Patent is hereby corrected as shown below:

In the Specification

In Column 8, Line 26, please delete "$^7$As" and replace it with -- $^{77}$As --;

In Column 8, Line 27, please delete "$^{10}$Rh" and replace it with -- $^{105}$Rh --;

In Column 16, Line 36, please delete formula "$((D_q\text{-}Lk^1)_r\text{-}P)_z\text{-}Lk^2\text{-}Lk^3\text{-}(L)_2$" and replace it with -- $((D_q\text{-}Lk^1)_r\text{-}P^1)_z\text{-}Lk^2\text{-}Lk^3\text{-}(L)_2$ --;

In Column 31, Line 44, please delete "J3-lactamase" and replace it with -- β-lactamase --;

In Column 32, Line 58, please delete "J3-lactamase" and replace it with -- β-lactamase --;

In Column 50, Line 52, please delete "0.22 m" and replace it with -- 0.22 μm --;

In Column 60, Line 31, please delete "0.22 m" and replace it with -- 0.22 μm --; and In the Claims In Column 95, Claim 3, Line 47, please delete "or K,".

Signed and Sealed this
Twentieth Day of December, 2022

Katherine Kelly Vidal
*Director of the United States Patent and Trademark Office*

SEQUENCE LISTING

<160> NUMBER OF SEQ ID NOS: 38

<210> SEQ ID NO 1
<211> LENGTH: 345
<212> TYPE: DNA
<213> ORGANISM: Artificial Sequence
<220> FEATURE:
<223> OTHER INFORMATION: synthetic construct

<400> SEQUENCE: 1

```
gaggtccagc tggtgcagtc tggacctgag ctgaagaagc ctggggcctc agtgaaggtc      60
tcctgcaaga cttctggata cacattcact gaatacacca tccactgggt gaagcaggcc     120
catggaaagg gccttgagtg gattggaaac attaatccta acaatggtgg tactacctac     180
aaccagaagt tcgaggacag agccacattg actgtagaca agtccaccag cacagcctac     240
atggagctca gcagcctgag atctgaggat actgcagtct attactgtgc agctggttgg     300
aactttgact actggggcca aggcaccacg gtcaccgtct cctca                    345
```

<210> SEQ ID NO 2
<211> LENGTH: 345
<212> TYPE: DNA
<213> ORGANISM: Artificial Sequence
<220> FEATURE:
<223> OTHER INFORMATION: synthetic construct

<400> SEQUENCE: 2

```
gaggtccagc tggtgcagtc tggagctgag gtgaagaagc ctggggcctc agtgaaggtc      60
tcctgcaaga cttctggata cacattcact gaatacacca tccactgggt gaagcaggcc     120
cctggaaagg gccttgagtg gattggaaac attaatccta acaatggtgg tactacctac     180
aaccagaagt tcgaggacag agccacaatc actgtagaca agtccaccag cacagcctac     240
atggagctca gcagcctgag atctgaggat actgcagtct attactgtgc agctggttgg     300
aactttgact actggggcca aggcaccacg gtcaccgtct cctca                    345
```

<210> SEQ ID NO 3
<211> LENGTH: 345
<212> TYPE: DNA
<213> ORGANISM: Artificial Sequence
<220> FEATURE:
<223> OTHER INFORMATION: synthetic construct

<400> SEQUENCE: 3

```
gaggtccagc tggtgcagtc tggagctgag gtgaagaagc ctggggcctc agtgaaggtc      60
tcctgcaaga cttctggata cacattcact gaatacacca tccactgggt gaggcaggcc     120
cctggaaagg gccttgagtg gattggaaac attaatccta acaatggtgg tactacctac     180
```

```
aaccagaagt tcgaggacag agccacaatc actgtagaca agtccaccag cacagcctac    240
atggagctca gcagcctgag atctgaggat actgcagtct attactgtgc agctggttgg    300
aactttgact actggggcca aggcaccacg gtcaccgtct cctca                    345
```

<210> SEQ ID NO 4
<211> LENGTH: 345
<212> TYPE: DNA
<213> ORGANISM: Artificial Sequence
<220> FEATURE:
<223> OTHER INFORMATION: synthetic construct

<400> SEQUENCE: 4

```
gaggtccagc tggtgcagtc tggagctgag gtgaagaagc ctggggcctc agtgaaggtc     60
tcctgcaagg cttctggata cacattcact gaatacacca tccactgggt gaggcaggcc    120
cctggaaagg gccttgagtg gattggaaac attaatccta caatggtgg tactacctac    180 aaccagaagt tcgaggacag agtcacaatc actgtagaca agtccaccag cacagcctac    240
atggagctca gcagcctgag atctgaggat actgcagtct attactgtgc agctggttgg    300
aactttgact actggggcca aggcaccacg gtcaccgtct cctca                    345
```

<210> SEQ ID NO 5
<211> LENGTH: 345
<212> TYPE: DNA
<213> ORGANISM: Artificial Sequence
<220> FEATURE:
<223> OTHER INFORMATION: synthetic construct

<400> SEQUENCE: 5

```
gaggtccagc tggtgcagtc tggagctgag gtgaagaagc ctggggcctc agtgaaggtc     60
tcctgcaagg cttctggata cacattcact gaatacacca tccactgggt gaggcaggcc    120
cctggaaagg gccttgagtg gattggaaac attaatccta accagggtgg tactacctac    180
aaccagaagt tcgaggacag agtcacaatc actgtagaca agtccaccag cacagcctac    240
atggagctca gcagcctgag atctgaggat actgcagtct attactgtgc agctggttgg    300
aactttgact actggggcca aggcaccacg gtcaccgtct cctca                    345
```

<210> SEQ ID NO 6
<211> LENGTH: 321
<212> TYPE: DNA
<213> ORGANISM: Artificial Sequence
<220> FEATURE:
<223> OTHER INFORMATION: synthetic construct

<400> SEQUENCE: 6

```
gacattgtga tgacccagtc tcccagcttc ctgtccgcat cagtaggaga cagggtcacc     60
atcacttgca aggccagtca ggatgtgggt actgctgtag actggtatca acagaaacca    120
gggcaagctc ctaaactact gatttactgg gcatccaccc ggcacactgg agtccctgat    180
cgcttcacag gcagtggatc tgggacagat ttcactctca ccatcagcag actgcagtct    240
gaagactttg cagattattt ctgtcagcaa tataacagct atcctctcac gttcggccag    300
gggaccatgg tggatatcaa a                                              321
```

<210> SEQ ID NO 7
<211> LENGTH: 321
<212> TYPE: DNA
<213> ORGANISM: Artificial Sequence
<220> FEATURE:

<223> OTHER INFORMATION: synthetic construct

<400> SEQUENCE: 7

```
gacattgtga tgacccagtc tcccagcacc ctgtccgcat cagtaggaga cagggtcacc      60
atcacttgca aggccagtca ggatgtgggt actgctgtag actggtatca acagaaacca     120
gggcaagctc ctaaactact gatttactgg gcatccaccc ggcacactgg agtccctgat     180
cgcttcacag gcagtggatc tgggacagat ttcactctca ccatcagcag actgcagtct     240
gaagactttg cagattattt ctgtcagcaa tataacagct atcctctcac gttcggccag     300
gggaccaagg tggatatcaa a                                               321
```

<210> SEQ ID NO 8
<211> LENGTH: 321
<212> TYPE: DNA
<213> ORGANISM: Artificial Sequence
<220> FEATURE:
<223> OTHER INFORMATION: synthetic construct

<400> SEQUENCE: 8

```
gacattgtga tgacccagtc tcccagcacc ctgtccgcat cagtaggaga cagggtcacc      60
atcacttgca aggccagtca ggatgtgggt actgctgtag actggtatca acagaaacca     120
gggcaagctc ctaaactact gatttactgg gcatccaccc ggcacactgg agtccctgat     180
cgcttcagcg gcagtggatc tgggacagat ttcactctca ccatcagcag actgcagcct     240
gaagactttg cagattatta ctgtcagcaa tataacagct atcctctcac gttcggccag     300
gggaccaagg tggatatcaa a                                               321
```

<210> SEQ ID NO 9
<211> LENGTH: 321
<212> TYPE: DNA
<213> ORGANISM: Artificial Sequence
<220> FEATURE:
<223> OTHER INFORMATION: synthetic construct

<400> SEQUENCE: 9

```
gacattcaga tgacccagtc tcccagcacc ctgtccgcat cagtaggaga cagggtcacc      60
atcacttgca aggccagtca ggatgtgggt actgctgtag actggtatca acagaaacca     120
gggcaagctc ctaaactact gatttactgg gcatccaccc ggcacactgg agtccctgat     180
cgcttcagcg gcagtggatc tgggacagat ttcactctca ccatcagcag actgcagcct     240
gaagactttg cagtttatta ctgtcagcaa tataacagct atcctctcac gttcggccag     300
gggaccaagg tggatatcaa a                                               321
```

<210> SEQ ID NO 10
<211> LENGTH: 115
<212> TYPE: PRT
<213> ORGANISM: Artificial Sequence
<220> FEATURE:
<223> OTHER INFORMATION: synthetic construct

<400> SEQUENCE: 10

```
Glu Val Gln Leu Val Gln Ser Gly Pro Glu Leu Lys Lys Pro Gly Ala
 1               5                  10                  15

Ser Val Lys Val Ser Cys Lys Thr Ser Gly Tyr Thr Phe Thr Glu Tyr
            20                  25                  30

Thr Ile His Trp Val Lys Gln Ala His Gly Lys Gly Leu Glu Trp Ile
        35                  40                  45
```

Gly Asn Ile Asn Pro Asn Asn Gly Gly Thr Thr Tyr Asn Gln Lys Phe
            50                  55                  60

Glu Asp Arg Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ala Gly Trp Asn Phe Asp Tyr Trp Gly Gln Gly Thr Thr Val Thr
            100                 105                 110

Val Ser Ser
        115

<210> SEQ ID NO 11
<211> LENGTH: 115
<212> TYPE: PRT
<213> ORGANISM: Artificial Sequence
<220> FEATURE:
<223> OTHER INFORMATION: synthetic construct

<400> SEQUENCE: 11

Glu Val Gln Leu Val Gln Ser Gly Ala Glu Val Lys Lys Pro Gly Ala
  1               5                  10                  15

Ser Val Lys Val Ser Cys Lys Thr Ser Gly Tyr Thr Phe Thr Glu Tyr
                20                  25                  30

Thr Ile His Trp Val Lys Gln Ala Pro Gly Lys Gly Leu Glu Trp Ile
            35                  40                  45

Gly Asn Ile Asn Pro Asn Asn Gly Gly Thr Thr Tyr Asn Gln Lys Phe
            50                  55                  60

Glu Asp Arg Ala Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ala Gly Trp Asn Phe Asp Tyr Trp Gly Gln Gly Thr Thr Val Thr
            100                 105                 110

Val Ser Ser
        115

<210> SEQ ID NO 12
<211> LENGTH: 115
<212> TYPE: PRT
<213> ORGANISM: Artificial Sequence
<220> FEATURE:
<223> OTHER INFORMATION: synthetic construct

<400> SEQUENCE: 12

Glu Val Gln Leu Val Gln Ser Gly Ala Glu Val Lys Lys Pro Gly Ala
  1               5                  10                  15

Ser Val Lys Val Ser Cys Lys Thr Ser Gly Tyr Thr Phe Thr Glu Tyr
                20                  25                  30

Thr Ile His Trp Val Arg Gln Ala Pro Gly Lys Gly Leu Glu Trp Ile
            35                  40                  45

Gly Asn Ile Asn Pro Asn Asn Gly Gly Thr Thr Tyr Asn Gln Lys Phe
            50                  55                  60

Glu Asp Arg Ala Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ala Gly Trp Asn Phe Asp Tyr Trp Gly Gln Gly Thr Thr Val Thr
            100                 105                 110

Val Ser Ser
    115

<210> SEQ ID NO 13
<211> LENGTH: 115
<212> TYPE: PRT
<213> ORGANISM: Artificial Sequence
<220> FEATURE:
<223> OTHER INFORMATION: synthetic construct

<400> SEQUENCE: 13

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
    50                  55                  60

Glu Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser
    115

<210> SEQ ID NO 14
<211> LENGTH: 115
<212> TYPE: PRT
<213> ORGANISM: Artificial Sequence
<220> FEATURE:
<223> OTHER INFORMATION: synthetic construct

<400> SEQUENCE: 14

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Lys Gly Leu Glu Trp Ile
        35                  40                  45

Gly Asn Ile Asn Pro Asn Gln Gly Gly Thr Thr Tyr Asn Gln Lys Phe
    50                  55                  60

Glu Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser
    115

<210> SEQ ID NO 15
<211> LENGTH: 107
<212> TYPE: PRT
<213> ORGANISM: Artificial Sequence
<220> FEATURE:
<223> OTHER INFORMATION: synthetic construct

<400> SEQUENCE: 15

Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Arg Leu Gln Ser
65                  70                  75                  80

Glu Asp Phe Ala Asp Tyr Phe Cys Gln Gln Tyr Asn Ser Tyr Pro Leu
                85                  90                  95

Thr Phe Gly Gln Gly Thr Met Val Asp Ile Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: synthetic construct

<400> SEQUENCE: 16

Asp Ile Val Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Arg Leu Gln Ser
65                  70                  75                  80

Glu Asp Phe Ala Asp Tyr Phe Cys Gln Gln Tyr Asn Ser Tyr Pro Leu
                85                  90                  95

Thr Phe Gly Gln Gly Thr Lys Val Asp Ile Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: synthetic construct

<400> SEQUENCE: 17

Asp Ile Val Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Arg Leu Gln Pro
65                  70                  75                  80

Glu Asp Phe Ala Asp Tyr Tyr Cys Gln Gln Tyr Asn Ser Tyr Pro Leu
                85                  90                  95

Thr Phe Gly Gln Gly Thr Lys Val Asp Ile Lys
            100                 105

<210> SEQ ID NO 18
<211> LENGTH: 107
<212> TYPE: PRT
<213> ORGANISM: Artificial Sequence
<220> FEATURE:
<223> OTHER INFORMATION: synthetic construct

<400> SEQUENCE: 18

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Arg Leu Gln Pro
65                  70                  75                  80

Glu Asp Phe Ala Val Tyr Tyr Cys Gln Gln Tyr Asn Ser Tyr Pro Leu
                85                  90                  95

Thr Phe Gly Gln Gly Thr Lys Val Asp Ile Lys
            100                 105

<210> SEQ ID NO 19
<211> LENGTH: 345
<212> TYPE: DNA
<213> ORGANISM: Artificial Sequence
<220> FEATURE:
<223> OTHER INFORMATION: synthetic construct

<400> SEQUENCE: 19
gaggtccagc tgcaacagtc tggacctgag ctgaagaagc ctgggacttc agtgaggata      60
tcctgcaaga cttctggata cacattcact gaatacacca tccactgggt gaagcagagc     120
catggaaaga gccttgagtg gattggaaac attaatccta acaatggtgg tactacctac     180
aaccagaagt tcgaggacaa ggccacattg actgtagaca gtcctccag cacagcctac      240 atggagctcc gcagcctgac atctgaggat tctgcagtct attactgtgc agctggttgg     300
aactttgact actggggcca aggcaccacg ctcaccgtct cctca                     345

<210> SEQ ID NO 20
<211> LENGTH: 321
<212> TYPE: DNA
<213> ORGANISM: Artificial Sequence
<220> FEATURE:
<223> OTHER INFORMATION: synthetic construct

<400> SEQUENCE: 20
gacattgtga tgacccagtc tcacaaattc atgtccacat cagtaggaga cagggtcagc      60
atcatctgca aggccagtca ggatgtgggt actgctgtag actggtatca acagaaacca     120
gggcaatctc ctaaactact gatttactgg gcatccaccc ggcacactgg agtccctgat     180
cgcttcacag gcagtggatc tgggacagat ttcactctca ccatcaccaa tgtgcagtct     240
gaagacctgg cagattattt ctgtcagcaa tataacagct atcctctcac gttcggcgcc     300
gggaccatgc tggatctcaa a                                               321

<210> SEQ ID NO 21
<211> LENGTH: 345
<212> TYPE: DNA
<213> ORGANISM: Artificial Sequence
<220> FEATURE:
<223> OTHER INFORMATION: synthetic construct

<400> SEQUENCE: 21
gaggtccaac tggtacagtc tggacctgaa gtgaagaagc ctggggctac agtgaagata     60
tcctgcaaga cttctggata cacattcact gaatatacca tacactgggt gaagcaggcc    120
cctggaaagg gccttgagtg gattggaaac atcaatccta caatggtgg taccacctac     180
aatcagaagt tcgaggacaa ggccacacta actgtagaca agtccaccga tacagcctac    240
atggagctca gcagcctaag atctgaggat actgcagtct attattgtgc agctggttgg    300
aactttgact actggggcca agggaccctg ctcaccgtct cctca                    345

<210> SEQ ID NO 22
<211> LENGTH: 321
<212> TYPE: DNA
<213> ORGANISM: Artificial Sequence
<220> FEATURE:
<223> OTHER INFORMATION: synthetic construct

<400> SEQUENCE: 22
gacatccaga tgacccagtc tccctcatcc ctgtccacat cagtaggaga cagggtcacc     60
ctcacctgta aggccagtca agatgtgggt actgctgtag actggtatca acagaaacca    120
ggaccatctc ctaaactact gatttattgg gcatccactc ggcacactgg aatccctagt    180
cgcttctcag gcagtggatc tgggacagac ttcactctca ccatttctag tcttcagcct    240
gaagactttg cagattatta ctgtcagcaa tataacagct atcctctcac gttcggtcct    300
gggaccaagg tggacatcaa a                                               321

<210> SEQ ID NO 23
<211> LENGTH: 115
<212> TYPE: PRT
<213> ORGANISM: Artificial Sequence
<220> FEATURE:
<223> OTHER INFORMATION: synthetic construct

<400> SEQUENCE: 23

Glu Val Gln Leu Gln Gln Ser Gly Pro Glu Leu Lys Lys Pro Gly Thr
1               5                   10                  15

Ser Val Arg Ile Ser Cys Lys Thr Ser Gly Tyr Thr Phe Thr Glu Tyr
            20                  25                  30

Thr Ile His Trp Val Lys Gln Ser His Gly Lys Ser Leu Glu Trp Ile
        35                  40                  45

Gly Asn Ile Asn Pro Asn Asn Gly Gly Thr Thr Tyr Asn Gln Lys Phe
    50                  55                  60

Glu Asp Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ala Gly Trp Asn Phe Asp Tyr Trp Gly Gln Gly Thr Thr Leu Thr
            100                 105                 110

Val Ser Ser

<210> SEQ ID NO 24
<211> LENGTH: 107
<212> TYPE: PRT
<213> ORGANISM: Artificial Sequence
<220> FEATURE:
<223> OTHER INFORMATION: synthetic construct

<400> SEQUENCE: 24

```
Asp Ile Val Met Thr Gln Ser His Lys Phe Met Ser Thr Ser Val Gly
1               5                   10                  15

Asp Arg Val Ser Ile Ile Cys Lys Ala Ser Gln Asp Val Gly Thr Ala
            20                  25                  30

Val Asp Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Thr Asn Val Gln Ser
65                  70                  75                  80

Glu Asp Leu Ala Asp Tyr Phe Cys Gln Gln Tyr Asn Ser Tyr Pro Leu
                85                  90                  95

Thr Phe Gly Ala Gly Thr Met Leu Asp Leu Lys
            100                 105
```

<210> SEQ ID NO 25
<211> LENGTH: 115
<212> TYPE: PRT
<213> ORGANISM: Artificial Sequence
<220> FEATURE:
<223> OTHER INFORMATION: synthetic construct

<400> SEQUENCE: 25

```
Glu Val Gln Leu Val Gln Ser Gly Pro Glu Val Lys Lys Pro Gly Ala
1               5                   10                  15

Thr Val Lys Ile Ser Cys Lys Thr Ser Gly Tyr Thr Phe Thr Glu Tyr
            20                  25                  30

Thr Ile His Trp Val Lys Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
50                  55                  60

Glu Asp Lys Ala Thr Leu Thr Val Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Leu Leu Thr
            100                 105                 110

Val Ser Ser
        115
```

<210> SEQ ID NO 26
<211> LENGTH: 107
<212> TYPE: PRT
<213> ORGANISM: Artificial Sequence
<220> FEATURE:
<223> OTHER INFORMATION: synthetic construct

<400> SEQUENCE: 26

```
Asp Ile Gln Met Thr Gln Ser Pro Ser Ser Leu Ser Thr Ser Val Gly
1               5                   10                  15
```

Asp Arg Val Thr Leu Thr Cys Lys Ala Ser Gln Asp Val Gly Thr Ala
            20                  25                  30

Val Asp Trp Tyr Gln Gln Lys Pro Gly Pro Ser Pro Lys Leu Leu Ile
        35                  40                  45

Tyr Trp Ala Ser Thr Arg His Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Gln Gln Tyr Asn Ser Tyr Pro Leu
                85                  90                  95

Thr Phe Gly Pro Gly Thr Lys Val Asp Ile Lys
            100                 105

<210> SEQ ID NO 27
<211> LENGTH: 348
<212> TYPE: DNA
<213> ORGANISM: Artificial Sequence
<220> FEATURE:
<223> OTHER INFORMATION: synthetic construct

<400> SEQUENCE: 27
gaagtgaaac ttgaggagtc tggaggaggc ttggtgcaac ctggagggtc catgaaaatc    60
tcctgtgttg cctctggatt cactttcagt aattactgga tgaactgggt ccgccagtct   120
ccagagaagg ggcttgagtg ggttgctgaa attagatcgc aatctaataa ttttgcaaca   180
cattatgcgg agtctgtgaa agggagggtc atcatctcaa gagatgattc caagagtagt   240
gtctacctgc aaatgaacag tttgagagct gaagacactg ccgtttatta ctgtaccagg   300
cgatggaata tttctgggg ccaaggcacc actgtcacag tctcctca                348

<210> SEQ ID NO 28
<211> LENGTH: 321
<212> TYPE: DNA
<213> ORGANISM: Artificial Sequence
<220> FEATURE:
<223> OTHER INFORMATION: synthetic construct

<400> SEQUENCE: 28
aacattgtaa tgacccaatt tcccaaatcc atgtccgcct cagcaggaga gaggatgacc    60
ttgacctgca aggccagtga gaatgtgggt acttatgtgt cctggtatca acagaaacca   120
acacagtctc ctaagatgtt gatatacggg gcatccaacc ggttcactgg ggtcccagat   180
cgcttctccg gcagtggatc tggaacagat ttcattctga ccatcagcag tgtgcaggca   240
gaagaccttg tagattatta ctgtggacag agttacacct ttccgtacac gttcggaggg   300
gggaccaagc tggaaatgaa g                                             321

<210> SEQ ID NO 29
<211> LENGTH: 116
<212> TYPE: PRT
<213> ORGANISM: Artificial Sequence
<220> FEATURE:
<223> OTHER INFORMATION: synthetic construct

<400> SEQUENCE: 29

Glu Val Lys Leu Glu Glu Ser Gly Gly Gly Leu Val Gln Pro Gly Gly
1               5                   10                  15

Ser Met Lys Ile Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
            35                  40                  45

Ala Glu Ile Arg Ser Gln Ser Asn Asn Phe Ala Thr His Tyr Ala Glu
 50                  55                  60

Ser Val Lys Gly Arg Val Ile Ile Ser Arg Asp Asp Ser Lys Ser Ser
 65                  70                  75                  80

Val Tyr Leu Gln Met Asn Ser Leu Arg Ala Glu Asp Thr Ala Val Tyr
                 85                  90                  95

Tyr Cys Thr Arg Arg Trp Asn Asn Phe Trp Gly Gln Gly Thr Thr Val
                100                 105                 110

Thr Val Ser Ser
        115

<210> SEQ ID NO 30
<211> LENGTH: 107
<212> TYPE: PRT
<213> ORGANISM: Artificial Sequence
<220> FEATURE:
<223> OTHER INFORMATION: synthetic construct

<400> SEQUENCE: 30

Asn Ile Val Met Thr Gln Phe Pro Lys Ser Met Ser Ala Ser Ala Gly
 1               5                  10                  15

Glu Arg Met Thr Leu Thr Cys Lys Ala Ser Glu Asn Val Gly Thr Tyr
             20                  25                  30

Val Ser Trp Tyr Gln Gln Lys Pro Thr Gln Ser Pro Lys Met Leu Ile
         35                  40                  45

Tyr Gly Ala Ser Asn Arg Phe Thr Gly Val Pro Asp Arg Phe Ser Gly
     50                  55                  60

Ser Gly Ser Gly Thr Asp Phe Ile Leu Thr Ile Ser Ser Val Gln Ala
 65                  70                  75                  80

Glu Asp Leu Val Asp Tyr Tyr Cys Gly Gln Ser Tyr Thr Phe Pro Tyr
                 85                  90                  95

Thr Phe Gly Gly Gly Thr Lys Leu Glu Met Lys
                100                 105

<210> SEQ ID NO 31
<211> LENGTH: 2253
<212> TYPE: DNA
<213> ORGANISM: Artificial Sequence
<220> FEATURE:
<223> OTHER INFORMATION: synthetic construct

<400> SEQUENCE: 31
atgtggaacc tgctgcacga gacagacagc gccgtggcca ccgccagacg gcctagatgg      60
ctgtgtgccg cgctctggt gctggctggc ggcttcttcc tgctgggctt cctgttcggc     120
tggttcatca agagcagcaa cgaggccacc aacatcaccc ccaagcacaa catgaaggcc     180
tttctggacg agctgaaggc cgagaatatc aagaagttcc tgtacaactt cacccagatc     240
ccccacctgg ccggcaccga gcagaacttc cagctcgcca agcagatcca gagccagtgg     300
aaagagttcg gcctggacag cgtggaactg gcccactacg acgtgctgct gagctacccc     360
aacaagaccc acccaactca tcagcatc atcaacgagg acgcaacga gattttcaac     420 accagcctgt cgagccccc tccacccggc tacgagaacg tgtccgacat cgtgcccca     480 ttcagcgcct tcagtccaca aggcatgccc gagggcgacc tggtgtacgt gaactacgcc     540
cggaccgagg acttcttcaa gctggaacgg gacatgaaga tcaactgctc cggcaagatc     600

```
gtgatcgcca gatacggcaa ggtgttccgg ggcaacaaag tgaagaacgc ccagctcgct      660
ggggccaagg gcgtgatcct gtacagcgac cccgccgact acttcgcccc tggcgtgaag      720
tcctaccccg acggctggaa tctgcctggc ggcggagtgc agcggggcaa catcctgaac      780
ctgaacggcg ctggcgaccc cctgacacct ggctaccccg ccaacgagta cgcctacaga      840
cggggaatcg ccgaggccgt gggcctgcct agcatccctg tgcaccccat cggctactac      900
gacgcccaga aactgctgga aaagatgggc ggcagcgccc ctcccgacag ctcttggaga      960
ggcagcctga aggtgcccta acgtgggc cctggcttca ccggcaactt cagcacccag       1020
aaagtgaaga tgcacatcca cagcaccaac gaagtgaccc ggatctacaa cgtgatcggc      1080
accctgagag cgccgtgga acccgacaga tacgtgatcc tgggcggcca ccgggatagc      1140
tgggtgttcg cggcatcga ccctcagtct ggcgccgctg tggtgcacga gatcgtgcgg      1200
agctttggca ccctgaagaa agagggctgg cggcccagac ggaccatcct gttcgcctct      1260
tgggacgccg aggaattcgg cctgctgggc agcaccgagt gggccgagga aacagcaga      1320 ctgctccagg aacggggcgt cgcctacatc aacgccgaca gcagcatcga gggcaactac      1380
accctgcggg tggactgcac ccccctgatg tacagcctgg tgcacaacct gaccaaagag      1440
ctgaagtccc ccgacgaggg cttcgaggc aagagcctgt acgagagctg gaccaagaag      1500
tcccccagcc ccgagttcag cggcatgccc agaatcagca agctgggcag cggcaacgac      1560
ttcgaggtgt cttccagcg gctgggaatc gccagcggca gagcccggta caccaagaac      1620
tgggagacaa caagttctc cggctacccc ctgtaccaca gcgtgtacga gacatacgag      1680
ctggtggaaa agttctacga ccccatgttc aagtaccacc tgaccgtggc ccaagtgcgc      1740
ggaggcatgg tgttcgagct ggccaacagc atcgtgctgc ccttcgactg ccgggactac      1800
gccgtggtgc tgcggaagta cgccgacaaa atctacagca tcagcatgaa gcaccccag      1860 gaaatgaaga cctacagcgt gtccttcgac agcctgttca gcgccgtgaa gaatttcacc      1920
gagatcgcca gcaagttcag cgagcggctc caggacttcg acaagagcaa ccccatcgtg      1980
ctgagaatga tgaacgacca gctcatgttc ctggaacggg ccttcatcga ccccctgggc      2040
ctgcccgacc ggcccttcta cagacacgtg atctatgccc ccagcagcca caacaaatac      2100
gccggcgaga gcttccccgg aatctacgat gccctgttcg acatcgagag caaggtggac      2160
cccagcaagg cctgggggcga agtgaagcgg caaatctacg tggccgcctt cacagtgcaa      2220
gccgctgccg agacactgag cgaagtggcc tag                                  2253
```

<210> SEQ ID NO 32
<211> LENGTH: 750
<212> TYPE: PRT
<213> ORGANISM: Artificial Sequence
<220> FEATURE:
<223> OTHER INFORMATION: synthetic construct

<400> SEQUENCE: 32

```
Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
```

```
                65                  70                  75                  80

Pro His Leu Ala Gly Thr Glu Gln Asn Phe Gln Leu Ala Lys Gln Ile
                         85                  90                  95

Gln Ser Gln Trp Lys Glu Phe Gly Leu Asp Ser Val Glu Leu Ala His
                        100                 105                 110

Tyr Asp Val Leu Leu Ser Tyr Pro Asn Lys Thr His Pro Asn Tyr Ile
                        115                 120                 125

Ser Ile Ile Asn Glu Asp Gly Asn Glu Ile Phe Asn Thr Ser Leu Phe
                        130                 135                 140

Glu Pro Pro Pro Gly Tyr Glu Asn Val Ser Asp Ile Val Pro Pro
        145                 150                 155                 160

Phe Ser Ala Phe Ser Pro Gln Gly Met Pro Glu Gly Asp Leu Val Tyr
                        165                 170                 175

Val Asn Tyr Ala Arg Thr Glu Asp Phe Phe Lys Leu Glu Arg Asp Met
                        180                 185                 190

Lys Ile Asn Cys Ser Gly Lys Ile Val Ile Ala Arg Tyr Gly Lys Val
                        195                 200                 205

Phe Arg Gly Asn Lys Val Lys Asn Ala Gln Leu Ala Gly Ala Lys Gly
                        210                 215                 220

Val Ile Leu Tyr Ser Asp Pro Ala Asp Tyr Phe Ala Pro Gly Val Lys
        225                 230                 235                 240

Ser Tyr Pro Asp Gly Trp Asn Leu Pro Gly Gly Val Gln Arg Gly
                        245                 250                 255

Asn Ile Leu Asn Leu Asn Gly Ala Gly Asp Pro Leu Thr Pro Gly Tyr
                        260                 265                 270

Pro Ala Asn Glu Tyr Ala Tyr Arg Arg Gly Ile Ala Glu Ala Val Gly
                        275                 280                 285

Leu Pro Ser Ile Pro Val His Pro Ile Gly Tyr Tyr Asp Ala Gln Lys
                        290                 295                 300

Leu Leu Glu Lys Met Gly Gly Ser Ala Pro Pro Asp Ser Ser Trp Arg
        305                 310                 315                 320

Gly Ser Leu Lys Val Pro Tyr Asn Val Gly Pro Gly Phe Thr Gly Asn
                        325                 330                 335

Phe Ser Thr Gln Lys Val Lys Met His Ile His Ser Thr Asn Glu Val
                        340                 345                 350

Thr Arg Ile Tyr Asn Val Ile Gly Thr Leu Arg Gly Ala Val Glu Pro
                        355                 360                 365

Asp Arg Tyr Val Ile Leu Gly Gly His Arg Asp Ser Trp Val Phe Gly
                        370                 375                 380

Gly Ile Asp Pro Gln Ser Gly Ala Ala Val Val His Glu Ile Val Arg
        385                 390                 395                 400

Ser Phe Gly Thr Leu Lys Lys Glu Gly Trp Arg Pro Arg Arg Thr Ile
                        405                 410                 415

Leu Phe Ala Ser Trp Asp Ala Glu Glu Phe Gly Leu Leu Gly Ser Thr
                        420                 425                 430

Glu Trp Ala Glu Glu Asn Ser Arg Leu Leu Gln Glu Arg Gly Val Ala
                        435                 440                 445

Tyr Ile Asn Ala Asp Ser Ser Ile Glu Gly Asn Tyr Thr Leu Arg Val
                        450                 455                 460

Asp Cys Thr Pro Leu Met Tyr Ser Leu Val His Asn Leu Thr Lys Glu
        465                 470                 475                 480

Leu Lys Ser Pro Asp Glu Gly Phe Glu Gly Lys Ser Leu Tyr Glu Ser
                        485                 490                 495
```

-continued

```
Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
    690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750
```

```
<210> SEQ ID NO 33
<211> LENGTH: 115
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (9)..(9)
<223> OTHER INFORMATION: The residue at this position may be Ala or Pro
<220> FEATURE:
<221> NAME/KEY: VARIANT
<222> LOCATION: (11)..(11)
<223> OTHER INFORMATION: The residue at this position may be Val or Leu
<220> FEATURE:
<221> NAME/KEY: VARIANT
<222> LOCATION: (24)..(24)
<223> OTHER INFORMATION: The residue at this position may be Ala or Thr
<220> FEATURE:
<221> NAME/KEY: VARIANT
<222> LOCATION: (38)..(38)
<223> OTHER INFORMATION: The residue at this position may be Arg or Lys
<220> FEATURE:
<221> NAME/KEY: VARIANT
<222> LOCATION: (41)..(41)
<223> OTHER INFORMATION: The residue at this position may be Pro or His
<220> FEATURE:
<221> NAME/KEY: VARIANT
<222> LOCATION: (55)..(55)
```

<223> OTHER INFORMATION: The residue at this position may be Asn or Gln
<220> FEATURE:
<221> NAME/KEY: VARIANT
<222> LOCATION: (68)..(68)
<223> OTHER INFORMATION: The residue at this position may be Val or Ala
<220> FEATURE:
<221> NAME/KEY: VARIANT
<222> LOCATION: (70)..(70)
<223> OTHER INFORMATION: The residue at this position may be Ile or Leu

<400> SEQUENCE: 33

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
    50                  55                  60

Glu Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser
        115

<210> SEQ ID NO 34
<211> LENGTH: 107
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (3)..(3)
<223> OTHER INFORMATION: The residue at this position may be Gln or Val
<220> FEATURE:
<221> NAME/KEY: VARIANT
<222> LOCATION: (10)..(10)
<223> OTHER INFORMATION: The residue at this position may be Thr or Phe
<220> FEATURE:
<221> NAME/KEY: VARIANT
<222> LOCATION: (63)..(63)
<223> OTHER INFORMATION: The residue at this position may be Ser or Thr
<220> FEATURE:
<221> NAME/KEY: VARIANT
<222> LOCATION: (80)..(80)
<223> OTHER INFORMATION: The residue at this position may be Pro or Ser
<220> FEATURE:
<221> NAME/KEY: VARIANT
<222> LOCATION: (85)..(85)
<223> OTHER INFORMATION: The residue at this position may be Val or Asp
<220> FEATURE:
<221> NAME/KEY: VARIANT
<222> LOCATION: (87)..(87)
<223> OTHER INFORMATION: The residue at this position may be Tyr or Phe
<220> FEATURE:
<221> NAME/KEY: VARIANT
<222> LOCATION: (103)..(103)
<223> OTHER INFORMATION: The residue at this position may be Lys or Met

<400> SEQUENCE: 34

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
            20                  25                  30

```
Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Arg Leu Gln Pro
65                  70                  75                  80

Glu Asp Phe Ala Val Tyr Tyr Cys Gln Gln Tyr Asn Ser Tyr Pro Leu
                85                  90                  95

Thr Phe Gly Gln Gly Thr Lys Val Asp Ile Lys
                100                 105

<210> SEQ ID NO 35
<211> LENGTH: 142
<212> TYPE: PRT
<213> ORGANISM: Artificial Sequence
<220> FEATURE:
<223> OTHER INFORMATION: synthetic construct

<400> SEQUENCE: 35

Met Glu Leu Gly Leu Arg Trp Gly Phe Leu Val Ala Leu Leu Arg Gly
1               5                   10                  15

Val Gln Cys Gln Val Gln Leu Val Glu Ser Gly Gly Val Val Gln
                20                  25                  30

Pro Gly Arg Ser Leu Arg Leu Ser Cys Ala Ala Ser Gly Phe Ala Phe
            35                  40                  45

Ser Arg Tyr Gly Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Gln Tyr Leu Gln Met Asn Ser Leu Arg Ala Glu Asp Thr Ala Val
                100                 105                 110

Tyr Tyr Cys Ala Arg Gly Gly Asp Phe Leu Tyr Tyr Tyr Tyr Tyr Gly
            115                 120                 125

Met Asp Val Trp Gly Gln Gly Thr Thr Val Thr Val Ser Ser
        130                 135                 140

<210> SEQ ID NO 36
<211> LENGTH: 127
<212> TYPE: PRT
<213> ORGANISM: Artificial Sequence
<220> FEATURE:
<223> OTHER INFORMATION: synthetic construct

<400> SEQUENCE: 36

Met Arg Val Pro Ala Gln Leu Leu Gly Leu Leu Leu Leu Trp Leu Pro
1               5                   10                  15

Asp Thr Arg Cys Asp Ile Gln Met Thr Gln Ser Pro Ser Ser Leu Ser
                20                  25                  30

Ala Ser Val Gly Asp Arg Val Thr Ile Thr Cys Arg Ala Ser Gln Gly
            35                  40                  45

Ile Ser Asn Tyr Leu Ala Trp Tyr Gln Gln Lys Thr Gly Lys Val Pro
    50                  55                  60

Lys Phe Leu Ile Tyr Glu Ala Ser Thr Leu Gln Ser Gly Val Pro Ser
65                  70                  75                  80

Arg Phe Ser Gly Gly Gly Ser Gly Thr Asp Phe Thr Leu Thr Ile Ser
```

85                  90                  95

Ser Leu Gln Pro Glu Asp Val Ala Thr Tyr Tyr Cys Gln Asn Tyr Asn
                100                 105                 110

Ser Ala Pro Phe Thr Phe Gly Pro Gly Thr Lys Val Asp Ile Lys
            115                 120                 125

<210> SEQ ID NO 37
<211> LENGTH: 143
<212> TYPE: PRT
<213> ORGANISM: Artificial Sequence
<220> FEATURE:
<223> OTHER INFORMATION: synthetic construct

<400> SEQUENCE: 37

Met Glu Leu Gly Leu Arg Trp Val Leu Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Asn Tyr Val Met His Trp Val Arg Gln Ala Pro Gly Lys Gly Leu
    50                  55                  60

Glu Trp Val Ala Ile Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Gly Gly Tyr Asn Trp Asn Tyr Glu Tyr His Tyr Tyr
        115                 120                 125

Gly Met Asp Val Trp Gly Gln Gly Thr Thr Val Thr Val Ser Ser
    130                 135                 140

<210> SEQ ID NO 38
<211> LENGTH: 127
<212> TYPE: PRT
<213> ORGANISM: Artificial Sequence
<220> FEATURE:
<223> OTHER INFORMATION: synthetic construct

<400> SEQUENCE: 38

Met Arg Val Pro Ala Gln Leu Leu Gly Leu Leu Leu Cys Phe Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Thr Asn Tyr Leu Ala Trp Phe Gln Gln Lys Pro Gly Lys Ala Pro
    50                  55                  60

Lys Ser Leu Ile Tyr Ala Ala Ser Ser Leu Gln Ser Gly Val Pro Ser
65                  70                  75                  80

Lys Phe Ser Gly Ser Gly Ser Gly Thr Asp Phe Ser Leu Thr Ile Ser
                85                  90                  95

Ser Leu Gln Pro Glu Asp Phe Ala Thr Tyr Tyr Cys Gln Gln Tyr Asn
            100                 105                 110

Ser Tyr Pro Ile Thr Phe Gly Gln Gly Thr Arg Leu Glu Ile Lys
        115                 120                 125